(12) United States Patent
Fukuhara et al.

(10) Patent No.: US 12,023,837 B2
(45) Date of Patent: *Jul. 2, 2024

(54) MOLDING APPARATUS

(71) Applicant: YKK Corporation, Tokyo (JP)

(72) Inventors: Yoshiyuki Fukuhara, Toyama (JP); Yuji Takada, Toyama (JP)

(73) Assignee: YKK Corporation, Tokyo (JP)

( * ) Notice: Subject to any disclaimer, the term of this patent is extended or adjusted under 35 U.S.C. 154(b) by 254 days.

This patent is subject to a terminal disclaimer.

(21) Appl. No.: 17/465,044

(22) Filed: Sep. 2, 2021

(65) Prior Publication Data

US 2021/0393001 A1 Dec. 23, 2021

Related U.S. Application Data

(62) Division of application No. 16/062,038, filed as application No. PCT/JP2016/072654 on Aug. 2, 2016, now Pat. No. 11,219,285.

(30) Foreign Application Priority Data

Dec. 24, 2015 (WO) .................. PCT/JP2015/086076
Apr. 15, 2016 (WO) .................. PCT/JP2016/062281

(51) Int. Cl.
*B29C 48/00* (2019.01)
*A44B 18/00* (2006.01)
(Continued)

(52) U.S. Cl.
CPC ...... *B29C 48/0011* (2019.02); *A44B 18/0007* (2013.01); *A44B 18/0015* (2013.01);
(Continued)

(58) Field of Classification Search
CPC ... A41B 18/0049; B29C 43/222; B29C 43/46; B29C 2043/461; B29L 2031/727; B29L 2031/729

See application file for complete search history.

(56) References Cited

U.S. PATENT DOCUMENTS 4,083,667 A 4/1978 Livingston et al.
4,454,183 A 6/1984 Wollman
(Continued)

FOREIGN PATENT DOCUMENTS

CN 1232372 A 10/1999
CN 1307455 A 8/2001
(Continued)

OTHER PUBLICATIONS

U.S. Appl. No. 16/061,887, Final Office Action, Sep. 14, 2021, 12 pages.
(Continued)

*Primary Examiner* — Atul P. Khare
(74) *Attorney, Agent, or Firm* — Kilpatrick Townsend & Stockton LLP

(57) ABSTRACT

This manufacturing method of a molded surface fastener involves a primary molding step for forming a primary molded body and a secondary molding step for compressing a provisional element of the primary molded body while heating the same. A molding apparatus is provided with a mold member comprising multiple penetration holes and multiple concave portions, whereof each penetration hole communicates to at least one concave portion; in the primary molding step, the molding apparatus is used to form a primary molded body comprising a provisional element having a primary stem portion and a pawl portion is formed from the protruded portion by compressing the provisional element. By this means, it is possible to stably manufacture a molded surface fastener that has an engaging element comprising a pawl portion that projects from the outer peripheral edge of an engaging head portion.

4 Claims, 24 Drawing Sheets

(51) Int. Cl.
*A61F 13/62* (2006.01)
*B29C 39/14* (2006.01)
*B29C 43/22* (2006.01)
*B29C 43/46* (2006.01)
*B29C 69/02* (2006.01)
*B29C 43/52* (2006.01)
*B29L 31/00* (2006.01)

(52) U.S. Cl.
CPC ...... *A44B 18/0019* (2013.01); *A44B 18/0049* (2013.01); *A44B 18/0061* (2013.01); *A44B 18/0065* (2013.01); *A44B 18/0073* (2013.01); *A61F 13/625* (2013.01); *B29C 39/148* (2013.01); *B29C 43/222* (2013.01); *B29C 43/46* (2013.01); *B29C 69/02* (2013.01); *B29C 2043/461* (2013.01); *B29C 43/52* (2013.01); *B29L 2031/727* (2013.01)

(56) References Cited

U.S. PATENT DOCUMENTS

| | | | | |
|---|---|---|---|---|
| 5,057,259 | A * | 10/1991 | Parmelee | ............... B29C 33/36 |
| | | | | 425/576 |
| 5,785,784 | A | 7/1998 | Chesley et al. | |
| 5,879,604 | A | 3/1999 | Melbye et al. | |
| 5,913,482 | A | 6/1999 | Akeno et al. | |
| 5,951,931 | A | 9/1999 | Murasaki et al. | |
| 5,953,797 | A | 9/1999 | Provost et al. | |
| 6,054,091 | A | 4/2000 | Miller et al. | |
| 6,162,040 | A | 12/2000 | Minato et al. | |
| 6,287,665 | B1 * | 9/2001 | Hammer | ............ A44B 18/0061 |
| | | | | 264/210.2 |
| 6,627,133 | B1 | 9/2003 | Tuma | |
| 7,052,638 | B2 * | 5/2006 | Clarner | ................ B29C 43/46 |
| | | | | 264/296 |
| 7,350,276 | B2 | 4/2008 | Kirby et al. | |
| 7,516,524 | B2 | 4/2009 | Provost et al. | |
| 7,645,134 | B2 * | 1/2010 | Jackson | .............. B29C 33/424 |
| | | | | 425/363 |
| 7,807,081 | B2 * | 10/2010 | Tuma | ................ A44B 18/0065 |
| | | | | 264/166 |
| 8,784,722 | B2 | 7/2014 | Rocha | |
| 8,819,902 | B2 * | 9/2014 | Tuma | ................ A44B 18/0007 |
| | | | | 24/442 |
| 8,881,369 | B2 | 11/2014 | Kirby et al. | |
| 8,961,850 | B2 | 2/2015 | Wood et al. | |
| 9,210,970 | B2 | 12/2015 | Collins et al. | |
| 9,259,060 | B2 | 2/2016 | Cheng | |
| 11,034,063 | B2 * | 6/2021 | Bosser | ..................... B32B 3/20 |
| 2001/0022409 | A1 | 9/2001 | Parellada et al. | |
| 2002/0190418 | A1 | 12/2002 | Jens | |
| 2003/0085492 | A1 * | 5/2003 | Schulte | ............. B29C 67/0044 |
| | | | | 264/167 |
| 2003/0106188 | A1 | 6/2003 | Armela et al. | |
| 2003/0131453 | A1 | 7/2003 | Clarner et al. | |
| 2004/0031130 | A1 | 2/2004 | Clarner et al. | |
| 2004/0031553 | A1 | 2/2004 | Berger | |
| 2004/0074071 | A1 | 4/2004 | Golden et al. | |
| 2004/0229739 | A1 | 11/2004 | Gorman et al. | |
| 2005/0212170 | A1 | 9/2005 | Jahn et al. | |
| 2006/0096072 | A1 | 5/2006 | Minato et al. | |
| 2007/0063375 | A1 | 3/2007 | Tuma | |
| 2010/0306969 | A1 | 12/2010 | Seifert | |
| 2013/0067702 | A1 | 3/2013 | Tuma | |
| 2015/0010732 | A1 | 1/2015 | Tuma | |
| 2015/0275941 | A1 | 10/2015 | Nisogi | |
| 2017/0156451 | A1 | 6/2017 | Cheng | |
| 2018/0360170 | A1 | 12/2018 | Fukuhara et al. | |
| 2018/0368534 | A1 | 12/2018 | Fukuhara et al. | |
| 2019/0008239 | A1 | 1/2019 | Fukuhara et al. | |
| 2020/0390199 | A1 | 12/2020 | Michihata et al. | |

FOREIGN PATENT DOCUMENTS

| | | | |
|---|---|---|---|
| CN | 1336803 | A | 2/2002 |
| CN | 1644357 | A | 7/2005 |
| CN | 1798509 | A | 7/2006 |
| CN | 102984965 | A | 3/2013 |
| CN | 104812262 | A | 7/2015 |
| DE | 102007032622 | A1 * | 3/2008 ......... A44B 18/0049 |
| IN | 1374050 | A | 10/2002 |
| JP | 58-157404 | A | 9/1983 |
| JP | 2002-519078 | A | 7/2002 |
| JP | 2002-262908 | A | 9/2002 |
| JP | 2002-534194 | A | 10/2002 |
| JP | 2004-357894 | A | 12/2004 |
| JP | 2007-502229 | A | 2/2007 |
| JP | 2007-528765 | A | 10/2007 |
| JP | 2011-504776 | A | 2/2011 |
| JP | 2011-182910 | A | 9/2011 |
| JP | 2013-529974 | A | 7/2013 |
| JP | 2015-504736 | A | 2/2015 |
| WO | 1994/023610 | A1 | 10/1994 |
| WO | 1998/014086 | A1 | 4/1998 |
| WO | 2000/000053 | A1 | 1/2000 |
| WO | 2000/041479 | A2 | 7/2000 |
| WO | 2009/149909 | A2 | 12/2009 |
| WO | 2011/163193 | A1 | 12/2011 |
| WO | 2014/058717 | A1 | 4/2014 |
| WO | 2017/110106 | A1 | 6/2017 |

OTHER PUBLICATIONS

U.S. Appl. No. 16/062,038, Notice of Allowance, Sep. 24, 2021, 8 pages.
International Search Report, PCT Patent Application No. PCT/JP2016/072654, mailed Oct. 18, 2016.
Office Action, Korean Patent Application No. 10-2018-7015786, mailed Jan. 29, 2019.
Office Action, Korean Patent Application No. 10-2018-7015787, mailed Jan. 29, 2019.
Office Action, Korean Patent Application No. 10-2018-7015788, mailed Jan. 29, 2019.
European Extended Search Report, European Patent Application No. 15911340.6, Apr. 24, 2019, 8 pages.
European Extended Search Report, European Patent Application No. 16878030.2, Apr. 29, 2019, 8 pages.
European Extended Search Report, European Patent Application No. 16878714.1, Apr. 29, 2019, 9 pages.
Office Action, Japanese Patent Application No. 2017-558167, mailed Jun. 11, 2019, 6 pages.
Office Action, Japanese Patent Application No. 2017-557590, mailed Jun. 4, 2019, 8 pages.
Office Action, Japanese Patent Application No. 2017-557728, mailed Jun. 4, 2019, 10 pages.
U.S. Appl. No. 16/061,887, Restriction Requirement, Jan. 10, 2020, 9 pages.
U.S. Appl. No. 16/061,979, Restriction Requirement, Jan. 10, 2020, 10 pages.
PCT Patent Application No. PCT/JP2015/086076, International Search Report, Mar. 15, 2016, 17 pages.
PCT Patent Application No. PCT/JP2016/087982, International Search Report, Mar. 14, 2017, 14 pages.
Office Action, Chinese Patent Application No. 201580085530.3, Apr. 2, 2020, 14 pages.
U.S. Appl. No. 16/061,887, Non-Final Office Action, Mar. 18, 2020, 13 pages.
U.S. Appl. No. 16/061,979, Non-Final Office Action, Mar. 19, 2020, 10 pages.
Office Action, Chinese Patent Application No. 201680075920.7, Apr. 14, 2020, 16 pages.
Office Action, Chinese Patent Application No. 201680075917.5, May 28, 2020, 12 pages.
U.S. Appl. No. 16/061,887, Advisory Action, Nov. 30, 2020, 3 pages.

(56) References Cited

OTHER PUBLICATIONS

U.S. Appl. No. 16/061,887, Final Office Action, Sep. 18, 2020, 13 pages.
U.S. Appl. No. 16/061,979, Notice of Allowance, Sep. 14, 2020, 9 pages.
U.S. Appl. No. 16/061,979, Supplemental Notice of Allowance, Nov. 27, 2020, 2 pages.
Office Action, Chinese Patent Application No. 201680075917.5, Dec. 31, 2021, 12 pages.
Office Action, Chinese Patent Application No. 201680075920.7, Dec. 30, 2020, 16 pages.
U.S. Appl. No. 16/061,887, Notice of Allowance, Feb. 5, 2021, 8 pages.
Decision of Refusal, Japanese Patent Application No. 2017-557728, Nov. 28, 2019, 9 pages.
Office Action, Taiwanese Patent Application No. 105140797, Sep. 28, 2017, 10 pages.
Office Action, Taiwanese Patent Application No. 105142192, Aug. 14, 2017, 19 pages.
Office Action, Taiwanese Patent Application No. 105143110, Aug. 23, 2017, 9 pages.
U.S. Appl. No. 16/061,887 , Non-Final Office Action, Mar. 8, 2021, 13 pages.
U.S. Appl. No. 16/061,979 , Notice of Allowance, Mar. 10, 2021, 10 pages.
U.S. Appl. No. 16/807,251, Non-Final Office Action, Aug. 18, 2021, 9 pages.
U.S. Appl. No. 16/807,341, Non-Final Office Action, Aug. 20, 2021, 9 pages.
Chinese Patent Application No. 201680075917.5, Office Action, Jun. 23, 2021, 22 pages.
Chinese Patent Application No. 201680075920.7, Office Action, Jun. 28, 2021, 13 pages.
U.S. Appl. No. 16/062,038, Non-Final Office Action, Apr. 29, 2020, 16 pages.
U.S. Appl. No. 16/062,038, Final Office Action, Sep. 18, 2020, 13 pages.
U.S. Appl. No. 16/062,038, Advisory Action, Nov. 24, 2020, 3 pages.
U.S. Appl. No. 16/062,038, Non-Final Office Action, Mar. 10, 2021, 13 pages.
U.S. Appl. No. 16/062,038, Notice of Allowance, Jul. 22, 2021, 8 pages.
U.S. Appl. No. 17/129,115, Final Office Action, Feb. 23, 2024, 11 pages.
U.S. Appl. No. 17/129,115, Non-Final Office Action, Aug. 15, 2023, 12 pages.

* cited by examiner

Prior Art

Prior Art

MOLDING APPARATUS

This application is a divisional of U.S. patent application Ser. No. 16/062,038, which is incorporated by reference herein in its entirety.

TECHNICAL FIELD

The present invention relates to a manufacturing method of a molded surface fastener in which a plurality of male engaging elements stand on an upper surface of a flat plate-shaped base portion and a molding apparatus used for manufacturing the molded surface fastener.

BACKGROUND ART

Surface fastener products in which a pair of a female surface fastener having a plurality of loops and a male surface fastener which can be attached to and detached from the female surface fastener are combined and used are conventionally known. A male surface fastener manufactured by molding synthetic resin is generally formed such that a plurality of male engaging elements having a mushroom shape and the like stand on an upper surface of a flat plate-shaped base portion.

Surface fastener products having such a male surface fastener are used in a wide variety of goods nowadays, and they are often used for goods to wear such as disposable diapers, diaper covers for babies, supporters to protect limb joints, lumber corsets (belt for backache) and gloves.

Many kinds of molded surface fasteners used for disposable diapers have been developed, including JP2013-529974 A (Patent Document 1) for example.

The molded surface fastener described in Patent Document 1 is formed by standing a plurality of male engaging elements on a flat plate-shaped base portion. Each engaging element has a truncated stem portion and an engaging head portion integrally formed on the stem portion. The engaging head portion is formed to bulge from the stem portion in the same volume in all directions.

In at least some of the engaging elements of Patent Document 1, the bulging part of the engaging head portion extending in only one direction of x-direction or y-direction is directed downward to the base portion. According to Patent Document 1, the molded surface fastener having the engaging elements as mentioned above can have high peeling strength at the time of engaging with the surface fastener having loop-shaped female engaging elements.

Meanwhile, U.S. Patent Publication No. 2013/0067702 A specification (Patent Document 2) discloses a molded surface fastener in which engaging and separating properties are enhanced. Engaging elements provided on the molded surface fastener in Patent Document 2 has a stem portion standing on the base portion and an engaging head portion integrally formed on the stem portion. On an outer peripheral edge part of the engaging head portion, a plurality of teeth are provided to be rotation symmetry about a center point.

In Patent Document 2, as a method for manufacturing a molded surface fastener, a method of extruding molten synthetic resin material between a molding roller and a pressure roller is used. In this case, a plurality of molding cavities having a shape corresponding to the engaging elements of the molded surface fastener are formed on the outer peripheral surface of the molding roller.

Since the synthetic resin material is extruded between the molding roller and the pressure roller as above, a base portion is molded at a gap between the molding roller and the pressure roller, and engaging elements are integrally molded with the base portion by pushing the synthetic resin material into the molding cavities of the molding roller by the press roller. Then, after the synthetic resin material is cured while being rotated together with the molding roller, the cured synthetic resin is taken out from the molding cavities of the molding roller and peeled off from the molding roller, thereby the molded surface fastener of Patent Document 2 is manufactured.

WO 2000/000053 Publication (Patent Document 3, JP2002-519078 Publication corresponds thereto) discloses a method for manufacturing a surface fastener having a plurality of male engaging elements and a manufacturing apparatus therefor.

For example, in the manufacturing method described in Patent Document 3, a primary molding step for molding a primary molded body 80 having a flat plate-shaped base portion, a stem portion standing on the base portion and a primary head portion integrally formed on the stem portion is conducted, as shown in FIG. 42. Then, a secondary molding step for molding an engaging head portion by flattening the primary head portion in a diameter direction by passing the primary molded body 80 through a calender and pressing the primary head portion of the primary molded body 80.

In this case, the molding apparatus 81 for conducting the above primary molding has a molding cylindrical body 82 which rotates, a press cylinder 83 disposed facing to the molding cylinder 82 at a predetermined interval and an extruding head 84 which supplies molten thermoplastic resin between the molding cylinder 82 and the press cylinder 83. The molding cylinder body 82 of Patent Document 3 has an outer side screen 85 having a cylindrical shape and an inner side screen 86 having a cylindrical shape and contacting with an inner peripheral surface of the outer side screen 85 as shown in FIGS. 43 and 44.

On the outer side screen 85 of the molding cylinder 82, a plurality of cavities 87 which has a columnar shape and molding the stem portions. On the inner side screen 86, a plurality of cavities which has a columnar shape and molding the primary head portions. Each cavity 87 of the outer side screen 85 and each cavity 88 of the inner side screen 86 are disposed to be aligned at positions corresponding to each other.

Using the above molding apparatus 81 having such a molding cylinder 82, the molding cylinder 82 and the press cylinder 83 are rotated, and a thermoplastic resin material is supplied from the extruding head 84 between the molding cylinder 82 and the press cylinder 83. As a result, the primary molded body 80 in which a plurality of engaging elements having the stem portion and the primary head portion and having dents on the primary head portions stand on the base portion is molded.

Then, the obtained primary molded body 80 is passed through the calender to make each primary head portion thin, thereby the molded surface fastener according to Patent Document 3 in which a plurality of mushroom-shaped engaging elements stand on the base portion is manufactured. Further, the molded surface fastener manufactured in Patent Document 3 has a characteristics that a concave portion is formed at a center part of the upper surface of the engaging head portion of each engaging element.

PRIOR ART DOCUMENT

Patent Documents

Patent Document 1: JP 2013/529974 A
Patent Document 2: US 2013-0067702 A
Patent Document 3: WO2000/000053 A

SUMMARY OF INVENTION

Problems to be Solved by the Invention

Generally, for molded surface fasteners used for goods to be put on a body such as a disposable diaper or a diaper cover, it is demanded that attaching and detaching a male surface fastener and a female surface fastener is easy to be done, and an engaging strength (peeling strength) is enhanced so that a male surface fastener and a female surface fastener do not separate easily even in a case of moving one's body when both are engaged. Further, the molded surface fastener may be directly contacted with one's skin depending on the goods. Therefore, improving a texture on a top surface side of the molded surface fastener on which the male engaging elements are disposed has also been demanded in order to obtain soft touch feeling. Therefore, the molded surface fastener described in Patent Document 3 has room for further improvement in order to solve the above problems.

Accordingly, the specific objective of the present invention is to provide a manufacturing method of a molded surface fastener capable of manufacturing a molded surface fastener having a large engaging strength (peeling strength) with respect to a female surface fastener and from which excellent texture can be obtained stably, and a molding apparatus used for manufacturing the molded surface fastener.

Means for Solving the Problems

In order to achieve the above object, a method for manufacturing a molded surface fastener provided by the present invention is, as a most principal structure, a method for manufacturing a molded surface fastener made of synthetic resin in which a plurality of engaging elements stand on an upper surface of a flat plate-shaped base portion, and each engaging element has a stem portion standing on the base portion and an engaging head portion integrally formed on the stem portion, the method includes a primary molding step for molding a primary molded body having the base portion and a plurality of provisional elements standing on the base portion, and a secondary molding step for molding the molded surface fastener by heating the provisional elements of the primary molded body and compressing the provisional elements from above, in which the method includes, in the primary molding step, continuously molding the primary molded body in which at least a part of the provisional elements has a primary stem portion standing on the base portion and at least one protruded portion protruded from an outer peripheral side surface on an upper end part of the primary stem portion using a molding apparatus having a mold member provided with a plurality of penetration holes drilled to penetrate from an outer peripheral surface to an inner peripheral surface and a plurality of concave portions concaved on the inner peripheral surface and in which each penetration hole communicates to at least one of the concave portions, and a driving part rotating the mold member at a predetermined speed, and the method includes, in the secondary molding step, molding the stem portion and the engaging head portion as well as molding at least one pawl portion protruded on the outer peripheral edge part of the engaging head portion from the protruded portion by compressing an upper end part of the provisional elements from above.

The manufacturing method of the present invention preferably includes molding a rib portion bulging upward from the upper surface of the primary stem portion and an additional protruded portion protruded from the rib portion to an outside of the primary stem portion to the provisional element using the molding apparatus further having an auxiliary mold member disposed closely contacting with the inner peripheral surface of the mold member on an inside of the mold member and in which auxiliary concave portions communicating to the penetration holes of the mold member are concaved on an outer peripheral surface, and molding the pawl portion from the protruded portion and the additional protruded portion in the secondary molding step.

Another method for manufacturing a molded surface fastener according to the present invention is, as a most principal structure, a method for manufacturing molded surface fastener made of synthetic resin on which a plurality of engaging elements stand on an upper surface of a flat plate-shaped base portion, in which the method includes molding the molded surface fastener in which the engaging element has a stem portion standing on the base portion and at least one pawl portion protruded from the outer peripheral side surface on an upper end part of the stem portion using a molding apparatus having a mold member which has a plurality of penetration holes drilled to penetrate from the outer peripheral surface to the inner peripheral surface and a plurality of concave portions concaved on the inner peripheral surface and in which each penetration hole communicates with at least one of the concave portions and a driving part rotating the mold member at a predetermined speed.

In this case, it is preferable that the manufacturing method of the present invention includes deforming the pawl portion of at least a part of the engaging elements so as to protrude from the outer peripheral side surface of the stem portion parallel to the upper surface of the base portion or toward the base portion.

It is also preferable that the method includes molding a rib portion bulging upward from the upper surface of the stem portion and an additional pawl portion protruded to an outside of the stem portion from the rib portion to the engaging element using the molding apparatus further having an auxiliary mold member disposed closely contacting with the inner peripheral surface of the mold member on an inside of the mold member and in which auxiliary concave portions communicating to the penetration holes of the mold member are concaved on an outer peripheral surface.

Further, it is preferable that in the above manufacturing method of the present invention, a member having a cylindrical shape is used as the mold member.

Next, a molding apparatus provided by the present invention is a molding apparatus used for manufacturing a molded surface fastener made of synthetic resin on which a plurality of engaging elements stand on an upper surface of a base portion, the molding apparatus having, as a basic structure, a molding member, a driving part rotating the mold member at a predetermined speed and an extrusion nozzle extruding molten synthetic resin material toward the mold member, in which the mold member is provided with a plurality of penetration holes drilled to penetrate from an outer peripheral surface to an inner peripheral surface and a plurality of concave portions concaved on the inner peripheral surface, and each penetration hole of the mold member communicates with at least one of the concave portions.

In the molding apparatus of the present invention as above, it is preferable that the mold member has a cylindrical shape, and a die wheel is formed using the mold member and the driving part.

It is preferable that the molding apparatus of the present invention has an auxiliary mold member disposed closely contacting with the inner peripheral surface of the mold member on an inside of the mold member and in which auxiliary concave portions communicating to the penetration holes of the mold member are concaved on an outer peripheral surface, and the auxiliary mold member is rotated synchronously with the mold member.

Further, in the molding apparatus of the present invention, the concave portion is preferably a linear concave groove portion and a concave groove portion curved in a wavy shape.

In this case, it is preferable that a groove width of each concave groove portion is set at 0.005 mm or more and 0.1 mm or less, and a groove depth of each concave groove portion is set at 0.005 mm or more and 0.05 mm or less.

Effects of the Invention

In the method for manufacturing a molded surface fastener according to the first embodiment of the present invention, firstly, a primary molded body having a base portion and a plurality of provisional elements standing on the base portion is molded using a molding apparatus in a primary molding step.

The molding apparatus used at this time has a mold member and a driving part rotating the mold member at a predetermined speed. The mold member has a plurality of penetration holes drilled to penetrate from an outer peripheral surface to an inner peripheral surface and a plurality of concave portions concaved on the inner peripheral surface and allowing molten synthetic resin (molten resin) to flow in. Further, the mold member is formed such that each penetration hole communicates to at least one concave portion, and is capable of flowing molten resin filling the penetration hole from the outer peripheral surface side in the concave portion provided on the inner peripheral surface from the penetration hole.

The primary molding step is conducted using such a molding apparatus, thereby the primary molded body in which at least a part of the provisional elements has a primary stem portion standing on the base portion and at least one protruded portion protruded from the outer peripheral side surface in an upper end part of the primary stem portion is continuously molded.

Subsequently, a secondary molding step is conducted to heat the provisional elements of the primary molded body and to compress the provisional elements from the above. In the secondary molding step, a stem portion standing on the base portion and an engaging head portion integrally formed on the stem portion are molded from the primary stem portion and the protruded portion of the provisional element, and at the same time, at least one pawl portion protruded on an outer peripheral edge part of the engaging head portion is molded from the protruded portion of the provisional element. Thereby, a molded surface fastener having the engaging elements on which at least one micro pawl portion is protruded on the outer peripheral edge part of the engaging head portion can be manufactured efficiently and stably.

In the molded surface fastener thus manufactured, the pawl portion protruded on the outer peripheral edge part of the engaging head portion can have a pawl width dimension smaller than a width dimension of a boundary between the stem portion and the engaging head portion. The pawl width dimension here means a dimension of the pawl portion in a direction perpendicular to a protruding direction of the pawl portion or a bulging direction of the engaging head portion as well as a direction perpendicular to an upper and lower direction (standing direction of the stem portion) of the molded surface fastener.

The width dimension in the boundary means a dimension of imaginary straight line passing through a center of the boundary surface between the stem portion and the engaging head portion in one arbitrary direction among directions (or flat surfaces) perpendicular to an upper and lower direction (standing direction of the stem portion) of the molded surface fastener. In the present invention particularly, it means a dimension of a machine direction (MD: direction in which the molded surface fastener is conveyed) among the directions perpendicular to the standing direction of the stem portion in a molding step of the molded surface fastener. Further, in the engaging elements of the present invention, in a case that the boundary surface is a circular shape in a plan view, for example, a width dimension of the boundary is the same as a size of a diameter of a circular cross section of the boundary surface.

In the molded surface fastener manufactured by the present invention, the micro pawl portions are protruded on the outer peripheral edge part of the engaging head portion as mentioned above. Particularly, by conducting the above second molding step, the pawl portion can be formed to slope or curve downward toward the base portion from the engaging head portion. Therefore, an engaging strength with respect to loops is enhanced.

Although it is not limited to the case, when loops (engaging elements) of a female surface fastener are engaged with engaging elements of the molded surface fastener of the present invention, the loops of the female surface fastener can be hooked easily with the pawl portions of the engaging elements. As a result, the loops of the female surface fastener can be less dropped off from the engaging elements of the present invention (less removed), and the engaging strength is increased.

Therefore, according to the molded surface fastener manufactured by the present invention, the engaging strength (peeling strength) with respect to a female surface fastener can be effectively enhanced. Thus, in a case that the manufactured molded surface fastener is used for goods such as a disposable diaper, for example, even when various moves are conducted in a state that the molded surface fastener and a female surface fastener are combined, its combined state can be stably maintained.

Further, in the molded surface fastener manufactured by the present invention, the pawl portion provided on the outer peripheral edge part of the engaging head portion is minute. Therefore, when touching the molded surface fastener from the upper surface side which is the engaging surface, an influence on texture of the molded surface fastener by the pawl portion is reduced, and smooth touch feeling or soft and flexible touch feeling can be easily obtained. That is, according to the manufacturing method of the present invention, a male molded surface fastener having a high engaging strength and excellent texture of a surface can be stably provided.

In the manufacturing method according to the first embodiment of the present invention as above, a molding apparatus having the above mentioned mold member, an auxiliary mold member disposed closely contacting with the inner peripheral surface of the mold member on an inside of the mold member and in which auxiliary concave portions communicating to the penetration holes of the mold member are concaved on an outer peripheral surface, and a driving part rotating the mold member and the auxiliary mold member at a predetermined speed can be used in the primary molding step. Thereby, the primary molded body in which at least a part of the provisional elements has the primary stem portion and the protruded portion as mentioned above, a rib portion bulging upward from the upper surface of the primary stem portion and an additional protruded portion protruded from the rib portion to an outside of the primary stem portion can be molded continuously.

Subsequently, the second molding step heating the provisional engaging elements and compressing the provisional elements from the above is conducted to the obtained primary molded body. Thereby, the stem portion and the engaging head portion are molded, and at the same time, a pawl portion can be molded from the protruded portion and the additional protruded portion of the provisional element to an outer peripheral edge part of the engaging head portion. Thereby a plurality of pawl portions can be stably provided on the engaging head portion. Thus, the molded surface fastener having higher engaging strength can be stably provided.

Since the molding apparatus used for the primary molding step has the mold member forming the protruded portion on the provisional element and the auxiliary mold member forming the additional protruded portion on the provisional element, the pawl portion and the additional pawl portion can be provided as different protruded portions. Further, for example, the protruded portion and the additional protruded portion of the provisional element can be formed in different sizes from each other. Therefore, in the present invention, a molded surface fastener having an engaging element in which pawl portions having different sizes are protruded on one engaging head portion can also be manufactured.

In the manufacturing method of the molded surface fastener according to the second embodiment of the present invention, a molded surface fastener having a base portion and a plurality of engaging elements standing on the base portion is molded using a molding apparatus. The molding apparatus used therefor has a mold member and a driving part rotating the mold member at a predetermined speed. The mold member is provided with a plurality of penetration holes drilled to penetrate from the outer peripheral surface to the inner peripheral surface and a plurality of concave portions concaved on the inner peripheral surface and allowing molten synthetic resin (molten resin) to flow in. Further, the mold member is formed such that each penetration hole communicates with at least one concave portion, and molten resin filling the penetration hole from the outer peripheral surface side can be flowed into the concave portion provided on the inner peripheral surface from the penetration hole.

As the molding step is conducted using such a molding apparatus, a molded surface fastener in which at least a part of the engaging elements has a stem portion standing on the base portion and at least one pawl portion protruding from the outer peripheral side surface on the upper end part of the stem portion can be molded continuously and manufactured efficiently and stably.

In the molded surface fastener thus manufactured, the pawl portion protruded on the outer peripheral side surface of the stem portion can have the pawl width dimension smaller than a length of a line segment passing through the center on the upper surface of the stem portion and connecting two points on the upper end outer peripheral edge of the stem portion. Here, the line segment to be compared with the pawl width dimension of the pawl portion means an imaginary straight line passing the upper surface center of the stem portion and connecting two points on the upper end outer peripheral edge of the stem portion in the plan view of the engaging element. The imaginary straight line is perpendicular to the upper and lower direction (standing direction of the stem portion) of the molded surface fastener.

It is preferable that the line segment of the imaginary straight line as above is a line segment along a machine direction (MD: direction in which the molded surface fastener is conveyed) in the molding step of the molded surface fastener among directions perpendicular to the standing direction of the stem portion. Further in the present invention, in a case of the upper surface of the stem portion of the engaging element show a circular shape parallel to the upper surface of the base portion, a diameter of the circular upper surface of the stem portion corresponds to the line segment of the imaginary straight line.

In the molded surface fastener manufactured by the present invention, the micro pawl portions are protruded on the outer peripheral side surface of the upper end part of the stem portion, as mentioned above. The engaging element formed of such a stem portion and the micro pawl portions has a new shape different from conventional and generally known ones in a J-shape, a palm-tree shape or a mushroom shape.

In such an engaging element, the stem portion is easy to secure a large strength. Therefore, a shear strength of the manufactured molded surface fastener with respect to a female surface fastener can be effectively increased. Further, the stem portion has a large strength while the engaging element has no engaging head portion. Therefore, the engaging element of the manufactured molded surface fastener can be smoothly inserted between loops of the female surface fastener. In addition, the engaging element can be pushed deeply close to a root of the loops with respect to the female surface fastener. Thereby, the pawl portion of the engaging element can be hooked firmly to the loops and stably engaged.

Furthermore, in the molded surface fastener manufactured as above, the flat upper surface of the stem portion is exposed upward broadly, the engaging head portion is not provided, and only the micro pawl portions are formed to bulge to an outside from the stem portion. Therefore, when touching the molded surface fastener on the upper surface side which is to be an engaging surface, smooth touch feeling and soft and flexible touch feeling can be easy to be obtained. That is, according to the manufacturing method of the present invention, the characteristic male molded surface fastener in which the stem portion of the engaging element is hard to be bent, the pawl portion can hook a loop firmly to engage, and texture on the surface is excellent can be stably provided. The characteristic molded surface fasteners of the present invention are provided in addition to conventional molded surface fasteners, thereby the molded surface fasteners have a wide variety. As a result, they can easily correspond to various kinds of female surface fasteners (nonwoven fabric) more precisely.

In the manufacturing method according to the second embodiment of the present invention, after the molded surface fastener having the engaging elements are molded with the mold member of the molding apparatus, the molded surface fastener is held and pulled by an upper and lower pair of pickup rollers, thereby the molded surface fastener can be peeled off from the mold member. At this time, the engaging elements are pressed from above with the rotating pair of pickup rollers (upper side holding roller, particularly). Therefore, it is possible that the pawl portion formed on at least a part of the engaging elements is deformed to protrude parallel to the upper surface of the base portion or sloped or curved downward to the base portion from the outer peripheral side surface of the stem portion. Further, the pawl portion of the engaging element can be deformed to slope or curve downward further by conveying the molded surface fastener while heating, and blowing a hot air from above of the engaging elements after the molded surface fastener is peeled off from the mold member with the pickup rollers.

That is, in the manufacturing method according to the second embodiment, the pawl portion molded with the molding apparatus is formed by being pulled out forcibly from the mold member of the molding apparatus. Therefore, in some cases, it is protruded to extend upward above the upper surface of the stem portion from the outer peripheral side surface of the stem portion. On the other hand, the pawl portion of the engaging element can be deformed intentionally by pressing it with the pickup rollers from above as mentioned above, thereby the pawl portion can be protruded from the outer peripheral side surface of the stem portion to be parallel to the upper surface of the base portion or slope or curve downward to the base portion.

As the pawl portion is formed in such a protruding direction, when the loops of the female surface fastener are engaged with the molded surface fastener, the loops can be stably engaged with the pawl portions of the engaging elements, and the loops hooked by the pawl portions can be hard to be pulled out from the engaging elements. Therefore, the engaging strength (peeling strength) of the molded surface fastener with respect to the female surface fastener can be further increased.

Further, in the manufacturing method according to the second embodiment of the present invention, and in the molding step of the molded surface fastener, the molding apparatus having the mold member as above, the auxiliary mold member closely contacting with the inner peripheral surface of the mold member on an inside of the mold member and in which auxiliary concave portions communicating to the penetration holes of the mold member are concaved on an outer peripheral surface, and the driving part rotating the mold member and the auxiliary mold member at a predetermined speed. Thereby, the molded surface fastener in which at least a part of the engaging elements has the above-mentioned stem portion and pawl portion, a rib portion bulging upward from the upper surface of the stem portion and an additional pawl portion protruded from the rib portion toward an outside of the stem portion can be molded continuously.

Thereby, the pawl portion and the additional pawl portion can be provided to the engaging element as different protruded portions. Therefore, the molded surface fastener having higher engaging strength can be stably provided. Since the molding apparatus having the mold member and the auxiliary mold member is used, the pawl portion and the additional pawl portion in different sizes from each other can be easily formed on the engaging element, for example.

Further in the present invention, a member (die wheel) having a cylindrical shape can be used as a mold member of the molding apparatus in the manufacturing method according to the first and second embodiments as mentioned above. Thereby, the molding apparatus can be formed in a simple structure, and the primary molded body in the first embodiment or the molded surface fastener in the second embodiment can be stably molded using the molding apparatus.

Next, a molding apparatus of the present invention used for manufacturing a molded surface fastener has a mold member, a driving part rotating the mold member at a predetermined speed and an extrusion nozzle extruding molten synthetic resin material toward the mold member. The mold member has a plurality of penetration holes drilled to penetrate from the outer peripheral surface to the inner peripheral surface and a plurality of concave portions concaved on the inner peripheral surface. Further, each penetration hole of the mold member communicates with at least one concave portion.

The molding apparatus of the present invention as above can be formed in a simple structure. It can also mold the primary molded body in the first embodiment and the molded surface fastener in the second embodiment stably and efficiently as in the above. Particularly, the micro protruded portions provided on the primary molded body in the first embodiment and the micro pawl portions provided on the molded surface fastener in the second embodiment can be stably molded.

In the molding apparatus of the present invention, the mold member has a cylindrical shape, and a die wheel is formed using the mold member and the driving part. By using such a molding apparatus, the primary molded body in the first embodiment or the molded surface fastener in the second embodiment can be stably molded.

The molding apparatus of the present invention also has an auxiliary mold member disposed closely contacting with the inner peripheral surface of the mold member on an inside of the mold member and in which auxiliary concave portions communicating to the penetration holes of the mold member are concaved on an outer peripheral surface. Further, the auxiliary mold member rotates synchronously with the mold member. Using such a molding apparatus, the additional protruded portion as mentioned above can be stably formed on the provisional engaging element of the primary molded body in the first embodiment, and the additional pawl portion as mentioned above can be stably formed on the engaging element of the molded surface fastener in the second embodiment.

Further, in the molding apparatus of the present invention, concave groove portions in a linear shape or concave groove portions curved in a wavy shape are formed as the concave portion. Particularly in this case, a groove width of each concave groove portion is set at 0.005 mm or more and 0.1 mm or less, and a groove depth of each concave groove portion is set at 0.005 mm or more and 0.05 mm or less. Thereby, in the first embodiment, the protruded portion can be formed stably on the provisional element, and the primary molded body can be efficiently molded. In the second embodiment, the pawl portion can be molded on the engaging element stably, and the molded surface fastener can be efficiently molded.

MODES FOR CONDUCTING THE INVENTION

Hereinafter, modes for conducting the invention will be described in detail showing embodiments with reference to the drawings. It should be noted that the present invention is not limited to the embodiments explained as below, and various changes can be made as long as having a substantially same structure and similar functional effects to the present invention. In each following Embodiment, for example, the number, the disposed position and the forming density of the engaging elements disposed on the base portion of the molded surface fastener are not particularly limited, and can be changed arbitrarily.

Embodiment 1

Figure 1:
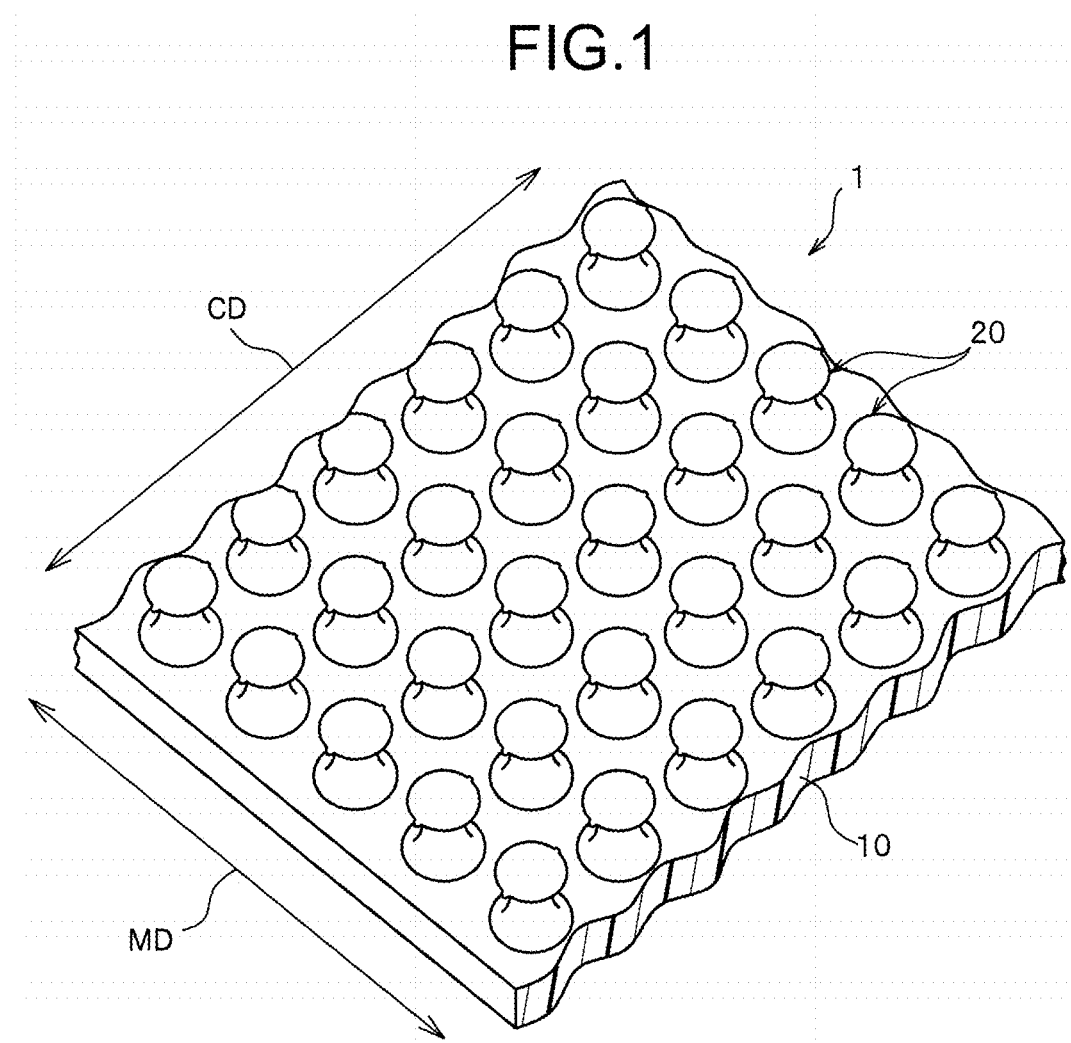
FIG. 1 is a perspective view illustrating a molded surface fastener to be manufactured according to Embodiment 1 of the present invention.
Figure 2:
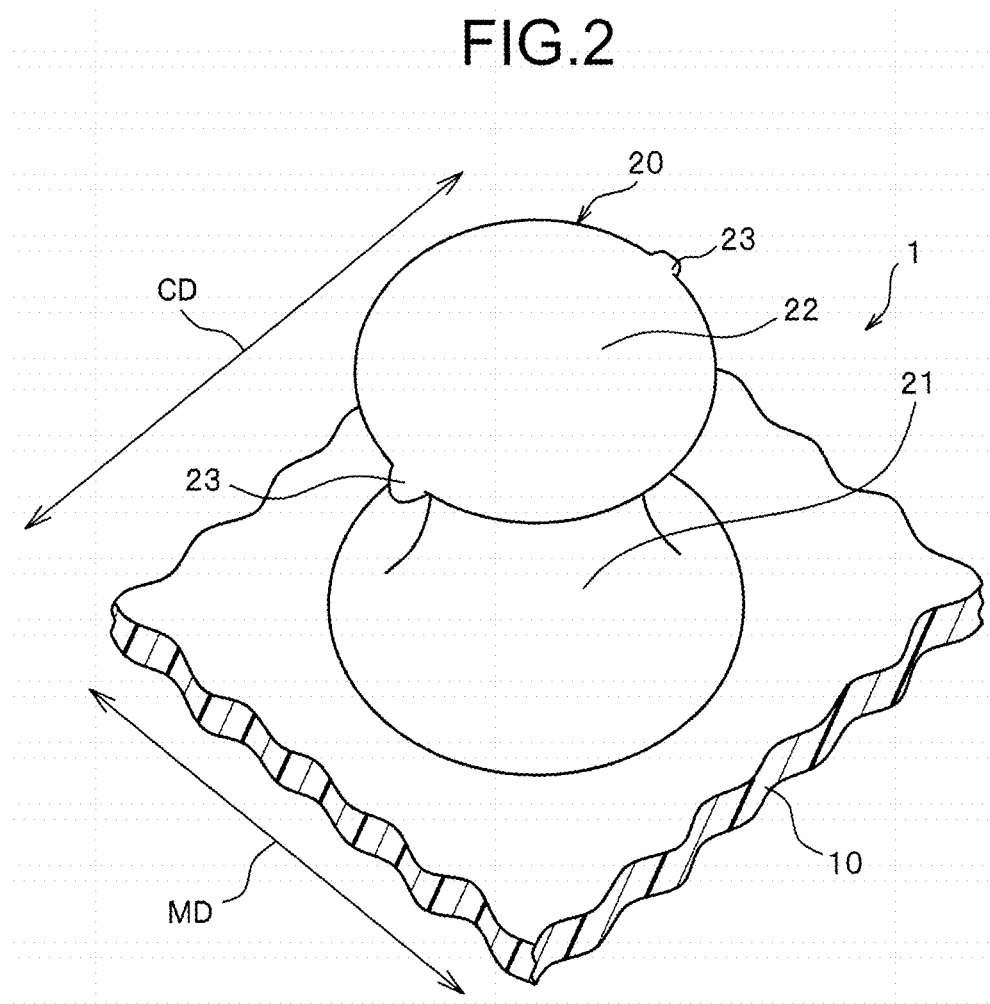
FIG. 2 is a perspective view illustrating an engaging element of the molded surface fastener.
Figure 3:
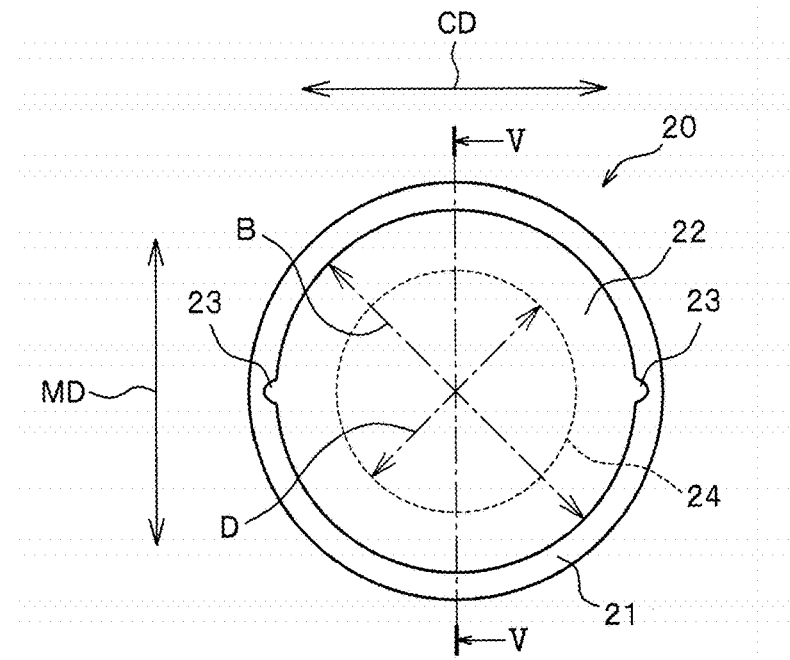
FIG. 3 is a plan view illustrating the engaging element only.
Figure 4:
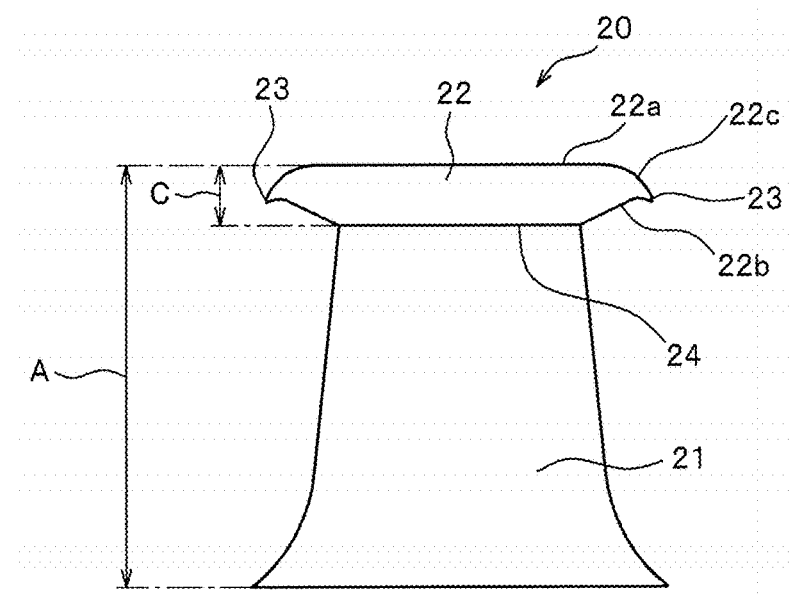
FIG. 4 is a front view of the engaging element only viewing from the front and rear direction (machine direction: MD) of the molded surface fastener.
Figure 5:
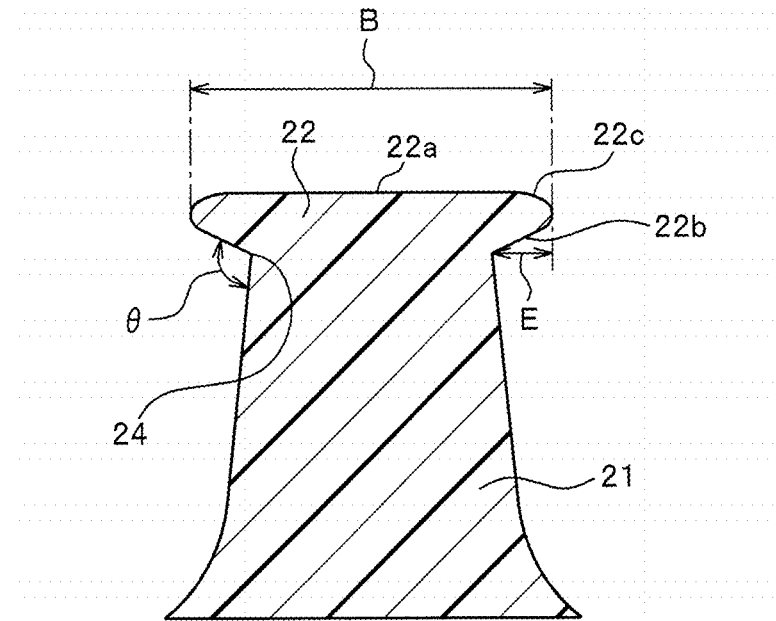
FIG. 5 is a cross-sectional view along the V-V line.
Figure 6:
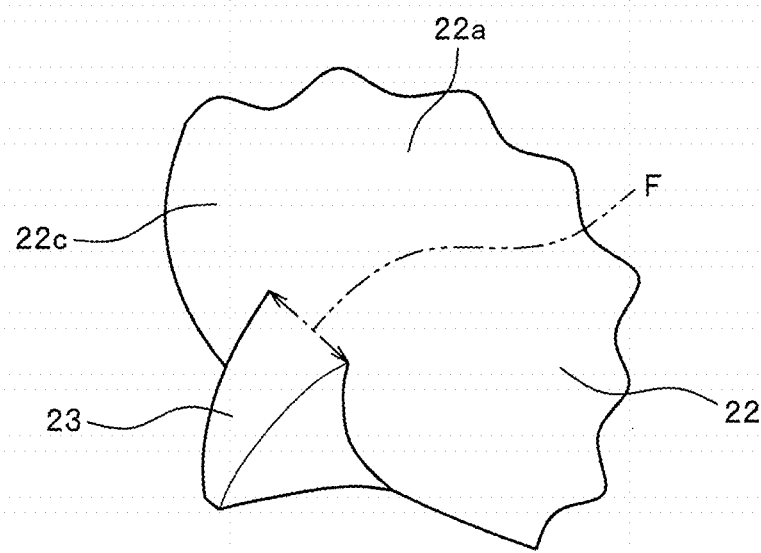
FIG. 6 is an enlarged perspective view illustrating a pawl portion disposed on the engaging element.

FIG. 1 is a perspective view illustrating a molded surface fastener to be manufactured according to Embodiment 1 of the present invention. FIG. 2, FIG. 3 and FIG. 4 are a perspective view, a plan view and a front view illustrating an engaging element of the molded surface fastener. FIG. 4 is a front view of the engaging element only viewing from the front and rear direction (machine direction: MD) of the molded surface fastener. FIG. 5 is a cross-sectional view of the engaging element. Further, FIG. 6 is an enlarged main part illustrating a pawl portion disposed on the engaging element.

In the following descriptions, a front and rear direction regarding a molded surface fastener and a primary molded body is a length direction of the molded surface fastener and the primary molded body molded in a long length, as mentioned later. A front and rear direction is a direction along a machine direction (M direction or MD) in which the molded surface fastener or the primary molded body is conveyed in the manufacturing step of the molded surface fastener.

A right and left direction is a width direction perpendicular to the length direction along an upper surface (or a lower surface) of the base portion of the molded surface fastener. In this case, the right and left direction and the width direction are crossing direction (C direction or CD) perpendicular to the machine direction (MD). An upper and lower direction (thickness direction) is a height direction perpendicular to the length direction, and perpendicular to the upper surface (or the lower surface) of the base portion of the molded surface fastener.

A molded surface fastener 1 of Embodiment 1 as shown in FIG. 1 is manufactured by molding thermoplastic resin using a manufacturing apparatus 30 having a molding apparatus 40 and a heat press apparatus 60, as described later. The molded surface fastener 1 is formed in a rectangular sheet shape which is long in the machine direction of the manufacturing apparatus 30 in a plan view. It should be noted that a length dimension and a width dimension of the molded surface fastener 1 of the present invention are not particularly limited, and can be changed arbitrarily by cutting the molded surface fastener 1. It is also possible that the molded surface fastener 1 has a shape other than the rectangular shape in a plan view.

Further, kinds of synthetic resin forming the molded surface fastener 1 is not particularly limited, either. However, as a material of the molded surface fastener 1, thermoplastic resin such as polypropylene, polyester, nylon, polybutylene terephthalate or copolymer thereof may be suitably used. In Embodiment 1, the molded surface fastener 1 is formed of polypropylene.

The molded surface fastener 1 of Embodiment 1 has a thin plate-shaped base portion 10 and a plurality of engaging elements 20 provided to stand on an upper surface of the base portion 10. The base portion 10 is formed to have a predetermined thickness, and the upper surface and a lower surface of the base portion 10 are formed to be flat and parallel to each other.

A plurality of engaging elements 20 are disposed to align along the machine direction (MD) and the crossing direction (CD). In the present invention, disposition of the engaging elements 20 is not limited, as mentioned above. For example, the plurality of engaging elements 20 may be aligned on the base portion 10 in a staggered shape or other patterns, or may be provided on the base portion 10 randomly.

Each engaging element 20 in Embodiment 1 has a stem portion 21 standing on the base portion 10, an engaging head portion 22 in a disc shape or a plate shape which is formed to bulge from the entire circumference of an upper end of the stem portion 21 to an outside and two micro pawl portions 23 protruded on an outer peripheral edge part of the engaging head portion 22.

The stem portion 21 of the engaging element 20 vertically stands on the base portion 10, and has a frustum shape such that a cross-sectional area perpendicular to the upper and lower direction gradually increases as approaching the base portion 10. Particularly, a lower end part of the stem portion 21 in Embodiment 1 is formed to curve such that the outer peripheral surface is spread downward. It should be noted that in the present invention, the shape of the stem portion 21 is not limited to the frustum shape, but may be a frustum of pyramid shape such as a frustum of square pyramid shape, a columnar shape or a prismatic columnar shape such as a square prismatic column shape.

The engaging head portion 22 of the engaging element 20 has a disc shape spreading in a direction perpendicular to the upper and lower direction. The engaging head portion 22 is integrally formed on the stem portion 21 via a boundary 24. Particularly, the engaging head portion 22 of Embodiment 1 has a circular shape in a plan view of the engaging element 20 viewed from an upper side. The circular shape of the engaging head portion 22 in the plan view has similarity to the circular shape in the lateral cross section perpendicular to the upper and lower direction on the boundary 24 of the engaging element 20.

In the similarity mentioned here, when a scale of one shape is overlapped with a scale of the other shape by increasing or decreasing its size for matching, not only a case of congruence in which the both shapes match completely but a case of overlapping at an area of 85% or higher, and preferably 90% of higher is included.

Particularly in this case, the engaging head portion 22 is formed to have a diameter more than 1.0 time and 3.0 times or less of a diameter D of a circular cross section in the boundary 24 of the engaging element 20, and preferably a diameter 1.3 times or more and 2.0 times or less. In a case that the engaging element 22 has a polygonal shape in a plan view, the engaging element 22 is formed to have a length of one side more than 1.0 time and 3.0 times or less of one arbitrary side of the polygonal cross section in the boundary 24 of the engaging element 20, and preferably 1.3 times or more and 2.0 times or less.

The engaging head portion 22 of Embodiment 1 has a flat head portion top end surface 22a disposed parallel to an upper surface of the base portion 10. On an opposite side of the head portion top end surface 22a, a doughnut-shaped head portion back surface 22b extending flat from the boundary 24 of the stem portion 21 to an outside so as to face the base portion 10. Further, from an outer periphery of the head portion top end surface 22a to the back surface of the head portion 22b, a curved surface-shaped outer peripheral side surface 22c is formed.

It should be noted that in the present invention, it is also possible that the shape of the engaging head portion 22 has a shape other than the circular shape corresponding to the lateral cross sectional shape of the stem portion 21. The engaging head portion 22 does not necessarily need to bulge from an entire periphery of the upper end of the stem portion 21. Further, in the plan view of the molded surface fastener 1, it is also possible that a central position of the engaging head portion 22 in one engaging element 20 is displaced to a central position of the cross section (cross section of the boundary 24) of the upper end of the stem portion 21 each other.

Each engaging element 20 of Embodiment 1 has two pawl portions 23 protruded to an outside from the outer peripheral side surface 22c of the engaging head portion 22. The two pawl portions 23 provided at the engaging element 20 protrude to the outside from the outer peripheral side surface 22c of the engaging head portion 22 along a diameter direction of the engaging head portion 22 showing a circular shape in a plan view to extend radically based on a center of the engaging head portion 22. Particularly, in a case of Embodiment 1, two pawl portions 23 are protruded in an opposite direction to each other from the outer peripheral side surface 22c of the engaging head portion 22 along a right and left direction (C direction) so as to be point symmetric each other in a plan view of the engaging element 20.

The pawl portion 23 of Embodiment 1 has a shape hanging down toward a tip end as a claw of a bird, as shown in the enlarged view in FIG. 6. The pawl portion 23 has a pawl upper surface sloping downward to the tip end, a pawl back surface (lower surface) disposed facing to the base portion 10 and a pair of side wall surfaces disposed on both sides of the pawl upper surface and the pawl back surface. It should be noted that in the present invention, a shape of the pawl portion 23 is not particularly limited as long as formed to protrude from the outer peripheral side surface 22c of the engaging head portion 22.

In this case, in a base end part of the pawl portion 23 jointing to the engaging head portion 22, a pawl width dimension F (see FIG. 6) between the pair of the side wall surfaces of the pawl portion 23 is set at one third of a dimension at the boundary 24 of the engaging element 20 in M direction (width dimension of the boundary 24) or smaller, preferably one fifth or smaller and more preferably one seventh or smaller. Since each pawl portion 23 is formed in a micro size having such a pawl width dimension F, a touch feeling of the molded surface fastener 1 can be less affected by the pawl portion 23 which contributes to improvement of the engaging strength of the molded surface fastener 1, as described later.

In a case of Embodiment 1, the cross-sectional shape (cross-sectional shape parallel to the upper surface of the base portion 10) at the boundary 24 of the engaging element 20 is a circular shape, and the dimension at the boundary 24 in M direction is equal to a dimension of the diameter at the boundary 24. Meanwhile, in a case that the cross-sectional shape of the engaging element at the boundary is a polygonal shape such as a square shape, the pawl width dimension F between the pair of side wall surfaces of the paw portion is set at one third of the dimension at the boundary of the engaging element or smaller, preferably one fifth or smaller, and more preferably one seventh or smaller.

The pawl portion 23 of Embodiment 1 has a shape such that the pawl width dimension between the pair of the side wall surfaces is gradually decreased from the base end part toward a pawl tip end of the pawl portion 23, and a pawl height dimension between the pawl upper surface and the pawl back surface is gradually decreased from the base end part toward the pawl tip end of the pawl portion 23. The tip end of the pawl portion 23 is formed to be at a position lower than the upper surface of the engaging head portion 22, and the pawl upper surface of the pawl portion 23 is formed in a curved surface shape sloping downward to the tip end. The pawl back surface of the pawl portion 23 is formed in a curved surface curving in a concave shape. Since the pawl portion 23 is formed in such a shape, an engaging strength of the molded surface fastener 1 can be effectively increased, and an excellent texture on the upper surface of the molded surface fastener 1 can be stably obtained.

In Embodiment 1, a specific size of the engaging element 20 is set as below.

For example, a height dimension A from the upper surface of the base portion 10 of the engaging element 20 in the upper and lower direction is set at 0.05 mm or more and 1.5 mm or less and preferably 0.2 mm or more and 1.0 mm or less. A diameter B of the engaging head portion 22 in a plan view of the engaging head portion 22 is set at 0.2 mm or more and 0.6 mm or less. In a case that the engaging head portion 22 has a polygonal shape in a plan view, a dimension of the engaging head portion 22 in M direction in a plan view of the engaging head portion 22 is set at 0.2 mm or more and 0.6 mm or less.

A height dimension C of the engaging head portion 22 in the engaging element 20 (i.e. a height dimension from the boundary 24 to the upper end of the engaging head portion 22 of the engaging element 20) is set at 0.01 mm or more and 0.1 mm or less. A diameter D of the engaging element 20 at the boundary 24 is set at 0.1 mm or more and 0.5 mm or less. In a case that the boundary 24 shows a polygonal shape in a plan view, a dimension of the boundary 24 in M direction is set at 0.1 mm or more and 0.5 mm or less.

A bulging dimension (bulging length) E from a position at the boundary 24 of the engaging element 20 at the engaging head portion 22 to the outermost edge position of the engaging head portion 22 in a direction parallel to the upper surface of the base portion 10 is set at 0.01 mm or more and 0.2 mm or less and preferably 0.02 mm or more and 0.1 mm or less. A bulging angle Θ formed by the outer peripheral side surface of the stem portion 21 and the back surface of the head portion 22b of the engaging head portion 22 in the engaging element 20 is set at 90° or larger and 140° or smaller.

A pawl width dimension F between the pair of the side wall surfaces in the base end part of the pawl portion 23 is set at 0.01 mm or more and 0.10 mm or less and preferably 0.03 mm or more and 0.08 mm or less. A pawl length dimension from a boundary position between the back surface of the head portion 22b of the engaging head portion 22 and the pawl back surface of the pawl portion 23 to a tip end position of the pawl portion 23 is set at 0.01 mm or more and 0.04 mm or less.

Figure 7:
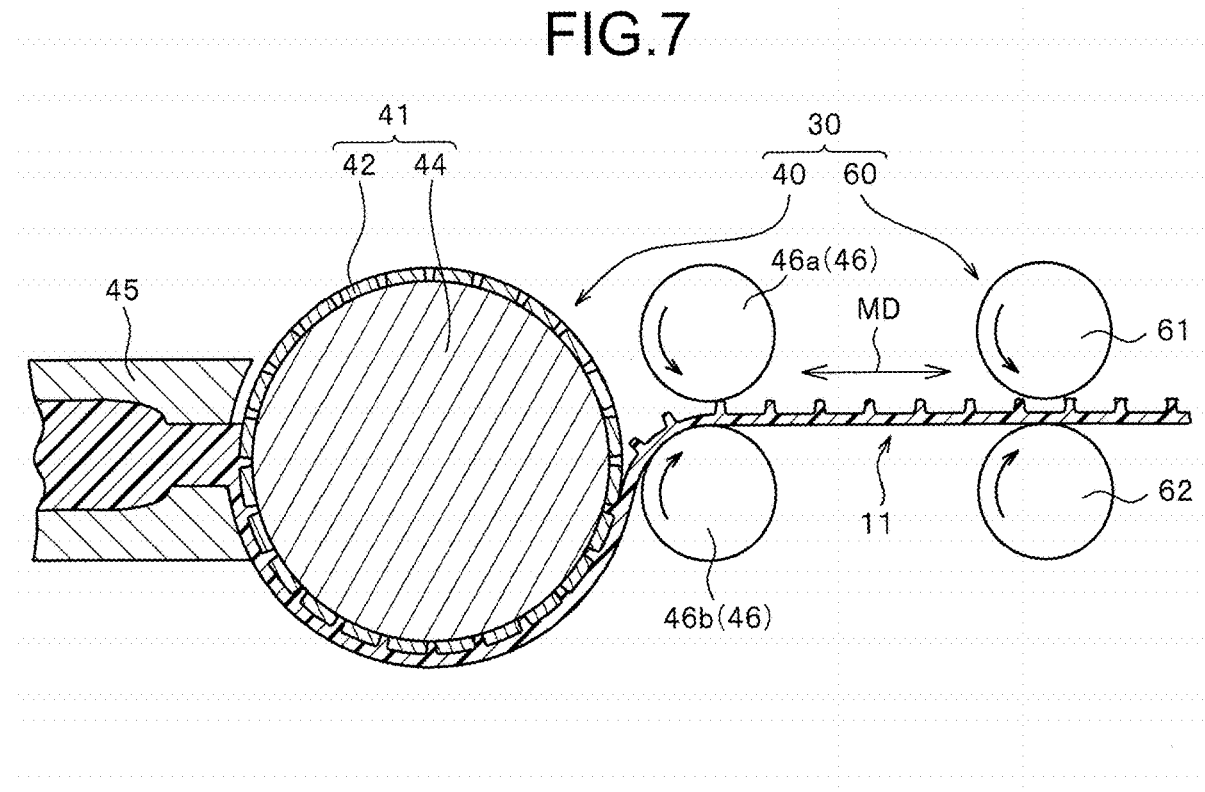
FIG. 7 is a schematic view illustrating schematically a manufacturing apparatus of the molded surface fastener.

The molded surface fastener 1 of Embodiment 1 having the above-mentioned structure is manufactured using a manufacturing apparatus as shown in FIG. 7.

The manufacturing apparatus 30 has a molding apparatus 40 conducting a primary molding step and a heat press apparatus 60 which heats and presses a primary molded body 11 molded in the primary molding step.

The molding apparatus 40 of Embodiment 1 has a die wheel 41 drive rotating in one direction (anticlockwise direction in the drawings), an extrusion nozzle 45 disposed facing to a circumferential surface of the die wheel 41 and extruding molten synthetic resin material continuously and a pickup roller 46 disposed on a downstream side of the extrusion nozzle 45 in the rotation direction of the die wheel 41.

The die wheel 41 has a cylindrical body 42 which serves as a mold member and a rotation driving roller 44 disposed as a driving part to rotate the cylindrical body 42 in one direction. Such a cylindrical body 42 is also called as a sleeve or cylindrical mold. In the rotation driving roller 44, a cooling jacket (not shown in the drawings) to distribute cooling liquid is provided, and can cool the primary molded body 11 molded on the circumferential surface of the die wheel 41 efficiently.

Figure 8:
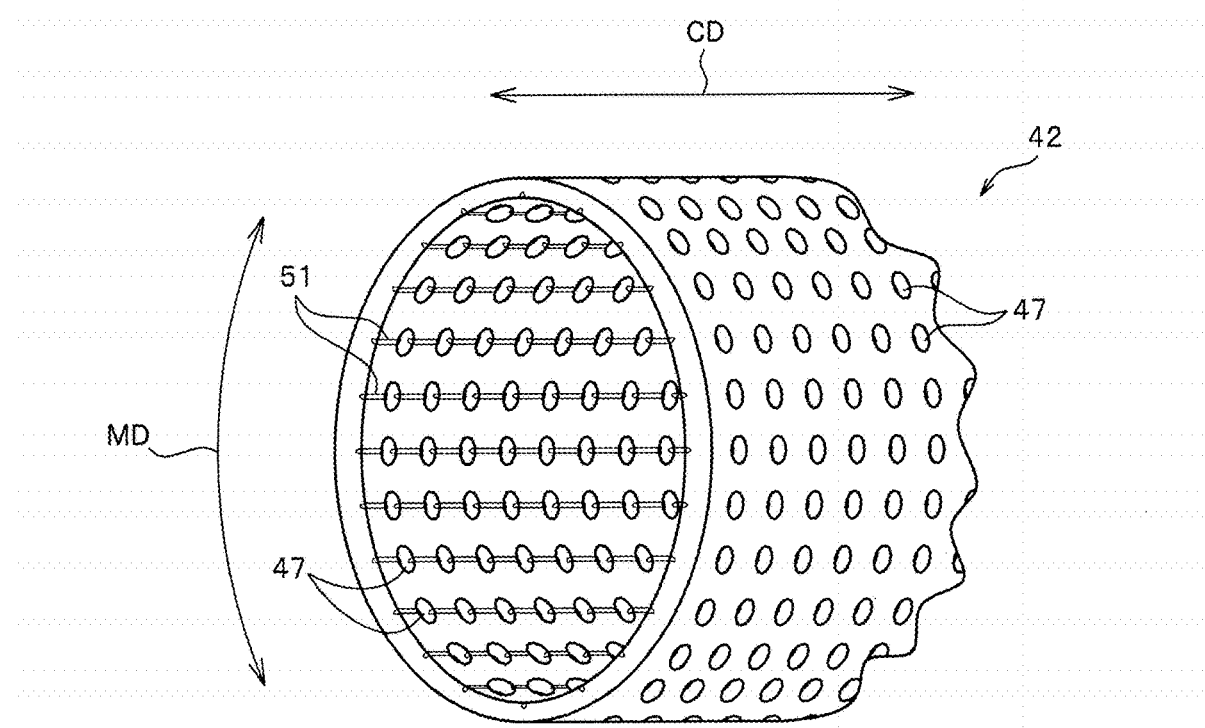
FIG. 8 is a perspective view illustrating schematically a cylindrical body disposed on the molding apparatus.
Figure 9:
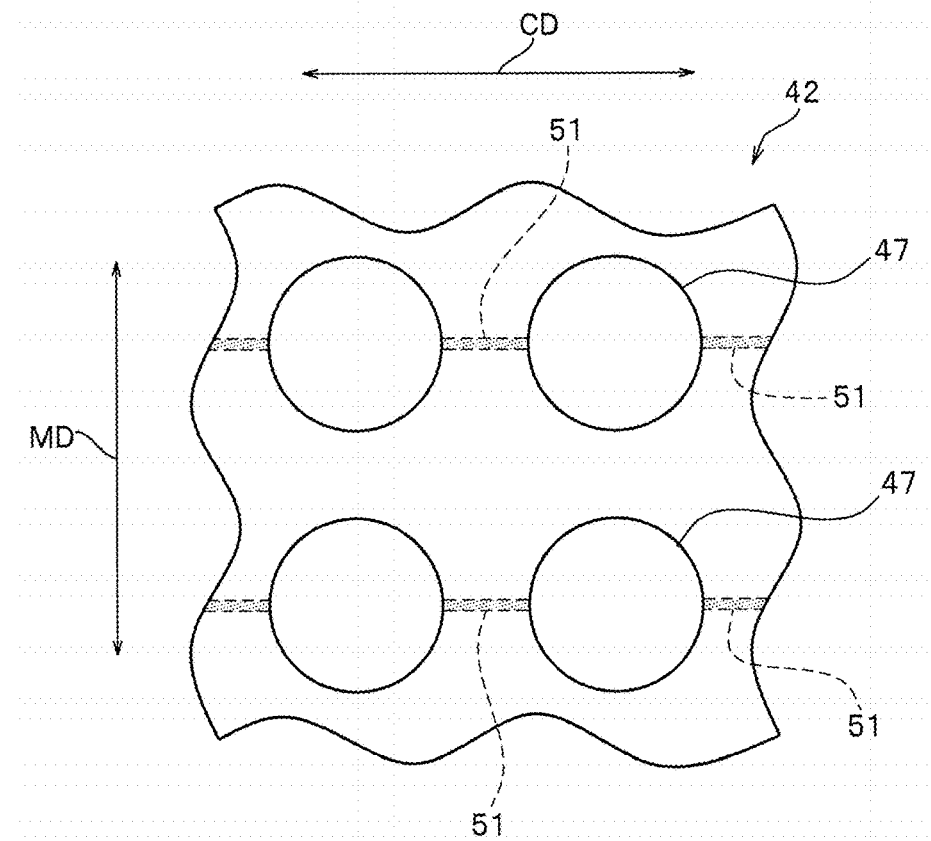
FIG. 9 is a main part schematic view illustrating a position relation between a penetration hole and a concave groove portion formed on the cylindrical body.
Figure 10:
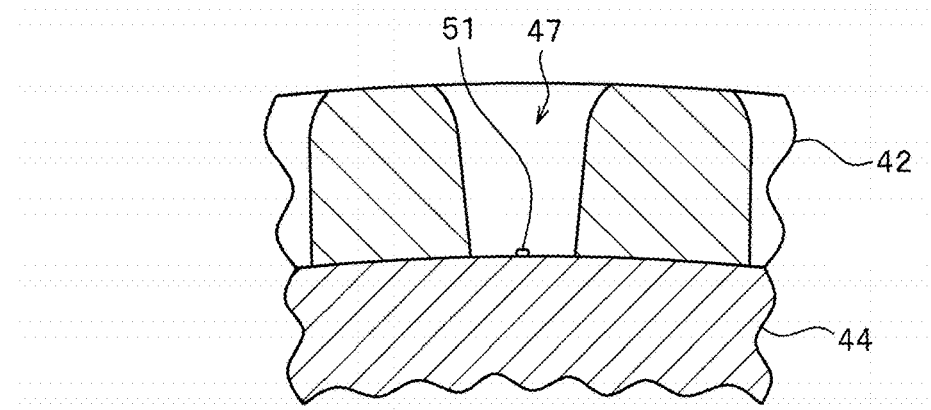
FIG. 10 is an enlarged cross-sectional view illustrating a main part of a die wheel in the molding apparatus.
Figure 11:
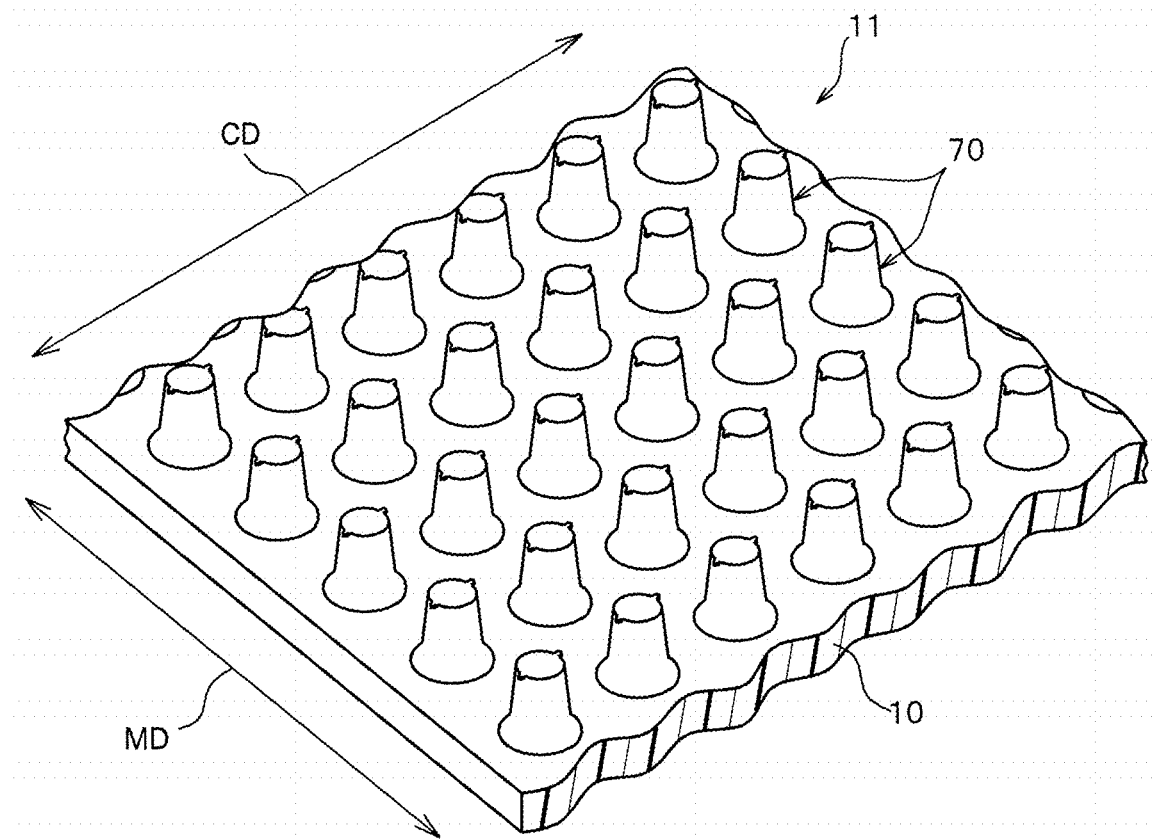
FIG. 11 is a schematic view illustrating a primary molded body molded with the molding apparatus.
Figure 12:
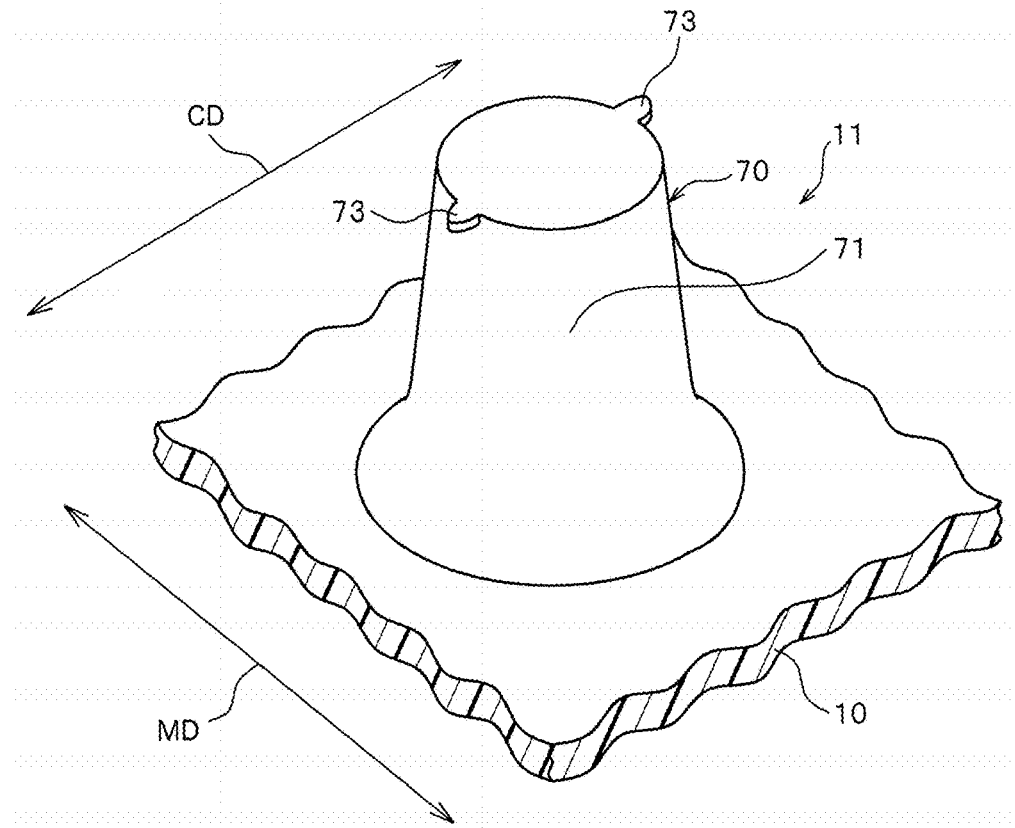
FIG. 12 is a perspective view illustrating a provisional element of the primary molded body.
Figure 13:
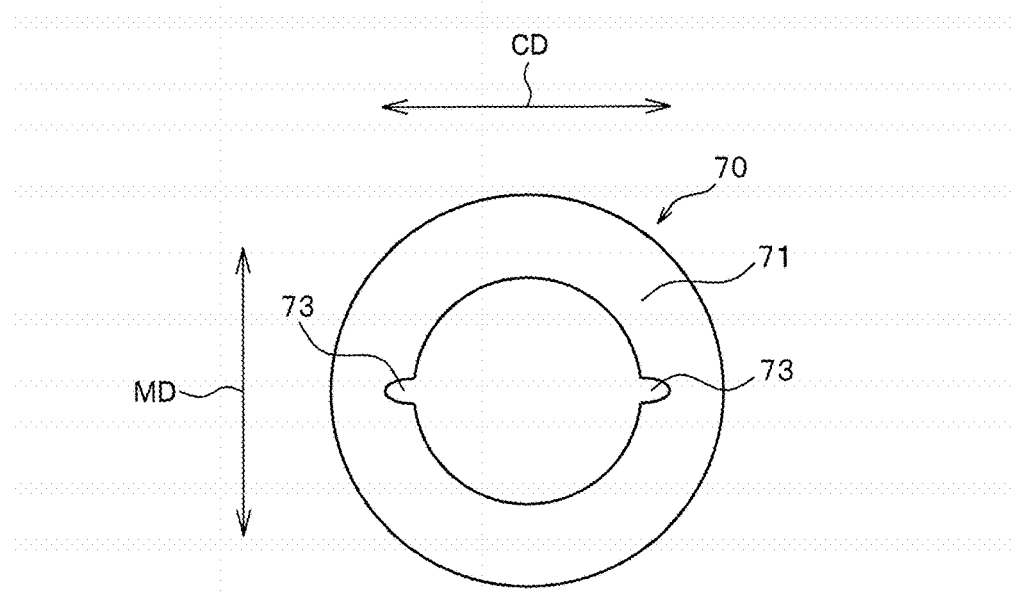
FIG. 13 is a plan view illustrating the provisional element only.
Figure 14:
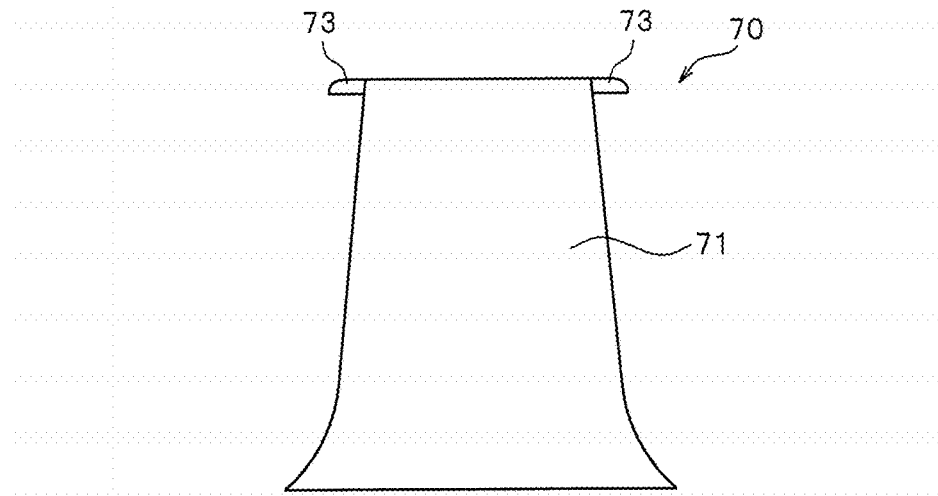
FIG. 14 is a front view illustrating the provisional element only viewing from the front and rear direction (MD) of the primary molded body.

In the cylindrical body 42 of the die wheel 41, a plurality of penetration holes 47 penetrating from an outer peripheral surface to an inner peripheral surface along a diameter direction of the cylindrical body 42 and a plurality of concave groove portions 51 which serve as concave portions concaved linearly in the inner peripheral surface of the cylindrical body 42 parallel to a central axis direction of the cylindrical body 42 are provided as shown in FIGS. 8 to 10. In the cylindrical body 42, the plurality of penetration holes 47 are provided as cavities forming primary stem portions 71 of the primary molded body 11, as described later, and the plurality of concave groove portions (concave portions) 51 are provided as cavities forming protruded portions 73 of the primary molded body 11, as described later.

The cylindrical body 42 of Embodiment 1 is produced by forming the primary cylindrical body 42 in a cylindrical shape, and thereafter forming the plurality of penetration holes 47 and the plurality of concave groove portions 51 at predetermined positions of the primary cylindrical body 42.

In this case, the primary cylindrical body 42 is produced from known metal such as nickel and stainless steel. For example, a seamless primary cylindrical body 42 is produced by forming a metal plate having a predetermined thickness and length by extending by applying pressure, rolling the metal plate in a cylindrical shape and welding it.

As a method for processing the plurality of the penetration holes 47 and the plurality of concave groove portions 51 to the produced primary cylindrical body 42, a known general technique can be used.

For example, laser processing, electron beam processing, machine processing including holing processing and etching processing can be used. It is also possible that the cylindrical body 42 of Embodiment 1 is produced by forming the plurality of penetration holes 47 and the plurality of concave groove portions 51 at predetermined positions of the metal plate having a flat plate shape, and thereafter rolling and welding the metal plate in a circular cylindrical shape. In the present invention, a method of producing the cylindrical body 42, a size and a thickness of the cylindrical body 42, and a shape and disposition of the penetration holes 47 and the concave groove portions 51 provided on the cylindrical body 42 are not particularly limited.

In the cylindrical body 42 of Embodiment 1, the plurality of penetration holes 47 are formed corresponding to a disposition of the engaging elements 20 of the molded surface fastener 1 which is to be manufactured. For example, the penetration holes 47 of Embodiment 1 are formed at regular intervals at predetermined pitches in a circumferential direction which is M direction (MD) of the cylindrical body 42, and are formed at regular intervals at predetermined pitches in C direction (CD) parallel to the central axis of the cylindrical body 42.

The plurality of concave groove portions 51 are concaved linearly in the inner peripheral surface of the cylindrical body 42 along C direction (CD) parallel to the central axis of the cylindrical body 42. The concave groove portion 51 has a size in which synthetic resin forming the molded surface fastener 1 can flow in a molten state. Particularly in the case of Embodiment 1, a position relation of the penetration holes 47 and the concave groove portions 51 provided on the cylindrical body 42 is such that the concave groove portion 51 crosses the circular outer peripheral edge of the penetration hole 47 formed on the cylindrical body 42 and communicates to the penetration hole 47, as shown in FIG. 9.

The concave groove portions 51 are formed at a position overlapped with a straight line along C direction connecting diameters of the plurality of penetration holes 47 aligned in C direction to have predetermined intervals in a circumferential direction which is M direction. FIG. 9 is a schematic view viewing a part of the cylindrical body 42 from the outer peripheral surface side, and the concave groove portions 51 are represented with a dashed line, and groove bottom surfaces of the concave groove portions 51 are shown in a gray color (the same applies to FIGS. 15, 18 and 23).

As shown in FIG. 9, the relative position of the concave groove portions 51 with respect to the penetration holes 47 can be precisely adjusted by providing the penetration holes 47 and the concave groove portions 51 in one cylindrical body 42. Therefore, when the primary molded body 11 is molded as described later, a provisional element 70 having a predetermined shape can be molded stably, and as a result, the molded surface fastener 1 having a plurality of engaging elements 20 having a predetermined shape as shown in FIG. 2 can be stably manufactured.

It should be noted that in Embodiment 1, the forming pitches of the penetration holes 47 which are provided on the cylindrical body 42 in a circumferential direction and the forming pitches of the concave groove portions 51 concaved on the inner peripheral surface in the circumferential direction are set so that the positions of the penetration holes 47 and the concave groove portions 51 correspond to each other, as mentioned above. However, it is also possible in the present invention that the forming pitches of the penetration holes 47 and the forming pitches of the concave groove portions 51 are set not to correspond to each other.

For example, by providing a plurality of concave groove portions 51 at smaller forming pitches than the forming pitches of the penetration holes 47, two or more pawl portions can be stably formed on the engaging head portion of each engaging element. On the other hand, by providing a plurality of concave groove portions 51 at larger forming pitches than the forming pitches of the penetration holes 47, a molded surface fastener having both of the engaging element on which the pawl portion is protruded on the engaging head portion and the engaging element on which the pawl portion is not provided on the engaging head portion can be manufactured.

Each concave groove portion 51 provided in Embodiment 1 has a flat groove bottom surface and a pair of groove side wall surfaces disposed to face parallel to each other so that a cross section in a direction perpendicular to the central axis is square-shaped. In this case, a groove width of each concave groove portion 51 is set at 0.005 mm or more and 0.10 mm or less, and preferably 0.01 mm or more and 0.08 mm or less. A groove depth of each concave groove portion 51 is set at 0.005 mm or more and 0.05 mm or less, preferably 0.005 mm or more and 0.03 mm or less, and more preferably 0.01 mm or more and 0.025 mm or less.

By setting the groove width of the concave groove portion 51 at 0.005 mm or larger and the groove depth at 0.005 mm or larger, when molding the primary molded body 11, molten synthetic resin can flow in the concave groove portion 51 from each penetration hole 47 of the cylindrical body 42 smoothly. Further, the pawl portions 23 of the solidified primary molded body 11 can be demolded from the concave groove portion 51 stably.

Meanwhile, by setting the groove width of the concave groove portion 51 at 0.10 mm or smaller and the groove depth at 0.05 mm or smaller, the micro pawl portions 23 can be formed stably as mentioned above on each engaging element 20 of the molded surface fastener 1. In this case particularly, the groove width of the concave groove portion 51 is set at a size of one third of a dimension of the penetration hole 47 in M direction provided on the cylindrical body 42 (a diameter dimension of the penetration hole 47 in a case of Embodiment 1) or smaller, preferably one fifth or smaller, and more preferably one seventh or smaller. It is also possible that the concave groove portion 51 formed on the inner peripheral surface of the cylindrical body 42 is formed to have a cross section in a substantially U-shape.

The pickup rollers 46 of Embodiment 1 has a pair of an upper side holding roller 46a and a lower side holding roller 46b which hold the primary molded body 11 formed on the outer peripheral surface of the die wheel 41 from upper and lower sides. A surface layer made of elastomer such as polyurethane elastomer which is not shown in the drawings is provided on the outer peripheral surface part of the upper side holding roller 46a on which the primary molded body 11 is contacted and on the outer peripheral surface part of the lower side holding roller 46b on which the primary molded body 11 is contacted.

The upper side holding roller 46a and the lower side holding roller 46b are disposed facing to each other at a predetermined interval. The upper side holding roller 46a and the lower side holding roller 46b rotate in a predetermined direction and a predetermined speed respectively, thereby the primary molded body 11 can be conveyed toward the heat press apparatus 60 smoothly while peeling off the primary molded body 11 continuously from the die wheel 41.

At the pickup rollers 46, just after the primary molded body 11 is peeled off from the die wheel 41, the primary molded body 11 is held with the upper side holding roller 46a and the lower side holding roller 46b, thereby the protruded portions (provisional pawl portions) 73 of the provisional elements 70 molded on the die wheel 41 can be deformed so as to protrude to be parallel to the upper surface of the base portion 10 or to decline or curve downward to the base portion 10.

A heat press apparatus 60 of Embodiment 1 has an upper and lower pair of press rollers (calender rollers) 61, 62 disposed on a downstream side of the pickup rollers 46, and the upper side press roller and the lower side press roller are disposed to face each other at a predetermined interval. In this case, the interval between the upper side press roller 61 and the lower side press roller 62 can be adjusted with a height adjusting means which is not shown in the drawings, and is adjusted corresponding to a height dimension from the lower surface (back surface) of the base portion 10 to the head portion top end surface 22a of the engaging head portion 22 in the engaging element 20 of the molding surface fastener 1 to be manufactured. In Embodiment 1, particularly, the interval between the upper side press roller 61 and the lower side press roller 62 is adjusted a little smaller than the interval between the upper side holding roller 46a and the lower side holding roller 46b of the pickup rollers 46.

The upper side press roller 61 has a heat source inside which is not shown in the drawings, and can heat and maintain the surface of the upper side press roller 61 at a predetermined temperature. In this case, the temperature of the surface of the upper side press roller 61 to be heated and maintained is not limited in particular, and set at the temperature capable of softening synthetic resin forming the molded surface fastener 1, for example. Specifically, it is set at the temperature at the melting point of the synthetic resin forming the primary molded body 11 minus 40° C. or higher and the temperature at the melting point minus 10° C. or lower. The upper side press roller 61 is disposed to rotate anticlockwise in FIG. 7. The outer peripheral surface of the upper side press roller 61 serves as a part pressing the heated provisional elements 70 of the primary molded body 11 molded in the primary molding step from above.

The lower side press roller 62 is disposed to rotate clockwise in FIG. 7 to be a supporting surface supporting the conveyed primary molded body 11 from the lower side. Instead of the upper side press roller 61 and/or the lower side press roller 62, it is possible in the present invention to use an upper side belt mechanism and/or a lower side belt mechanism which are not shown in the drawings. In this case, each of the upper side and the lower side belt mechanisms has an endless belt and a right and left pair of rotation rollers which the endless belt is wound around and rotate the endless belt in one direction.

In manufacturing the molded surface fastener 1 using the manufacturing apparatus 30 having the molding apparatus 40 and the heat press apparatus 60 as mentioned above, the primary molding step is conducted first to mold the primary molded body 11 using the molding apparatus 40. In the primary molding step, molten synthetic resin material is continuously extruded from an extrusion nozzle 45 toward a circumferential surface of the die wheel 41.

At this time, the die wheel is drive-rotating in one direction, and the base portion 10 of the molded surface fastener 1 is continuously molded between the extrusion nozzle 45 and the die wheel 41 by extruding the synthetic resin material on the circumferential surface. In this case, an interval between the extrusion nozzle 45 and the die wheel 41 is adjusted to a size corresponding to a thickness dimension of the base portion 10 of the molded surface fastener 1 to be manufactured.

At the same time of molding the base portion 10, a plurality of provisional elements 70 as shown in FIGS. 11 to 14 are molded integrally on the base portion 10 by the above-mentioned cylindrical body 42 disposed on the die wheel 41 as above. Thereby, the primary molded body 11 is produced.

Here, the primary molded body 11 (also referred to as a preliminary molded body) molded with the molding apparatus 40 of Embodiment 1 has a thin plate-shaped base portion 10 and the plurality of provisional elements 70 standing on the upper surface of the base portion 10. The base portion 10 of the primary molded body 11 serves as the base portion 10 of the molded surface fastener 1 without change.

The provisional element 70 formed at the primary molded body 11 is a part to be the engaging element 20 of the molded surface fastener 1 by press molding in the secondary molding step. In this case, each provisional element 70 has a primary stem portion 71 standing on the base portion 10 and having a frustum shape, and two protruded portions (provisional pawl portions) 73 protruded in a tongue shape to bulge outward from the outer peripheral side surface of an upper end part of the primary stem portion 71.

The primary stem portion 71 is molded by filling the penetration hole 47 drilled on the cylindrical body 42 with synthetic resin, and has a frustum shape such that a cross-sectional area perpendicular to the upper and lower direction is gradually increased as approaching to the base portion 10. An upper end surface of the primary stem portion 71 is formed to be a flat surface. The upper end surface of the primary stem portion 71 and the upper surface of two right and left protruded portions form a single flat surface.

The primary stem portion 71 of Embodiment 1 becomes the stem portion 21 and the engaging head portion 22 of the molded surface fastener 1 by pressing the provisional elements 70 from above and deforming the upper end part of the primary stem portion 71 in the secondary molding step.

The lower end part of the primary stem portion 71 has a similar shape to the lower end part of the stem portion 21. It is also possible that the primary stem portion 71 is formed in a frustum of pyramid shape such as a frustum of square pyramid shape, a columnar shape or a prismatic columnar shape such as a square prismatic column, depending on the shape of the stem portion 21 of the molded surface fastener 1 to be manufactured.

The protruded portion (provisional pawl portion) 73 is molded such that the synthetic resin flows in the concave groove portion 51 provided on the inner peripheral surface of the cylindrical body 42 from the penetration hole 47 of the cylindrical body 42 in the primary molding step. In this case, the two protruded portions 73 are protruded from the outer peripheral side surface of the primary stem portion 71 along C direction. The molded protruded portion 73 has a pole shape showing a rounded cross section due to contraction, etc.

In this case, molding of the protruded portion 73 is conducted not by filling the entire concave groove portion 51 provided on the inner peripheral surface of the cylindrical body 42 with the synthetic resin, but such that the synthetic resin flowing into the concave groove portion 51 from the penetration hole 47 of the cylindrical body 42 intrudes to a part of the concave groove portion 51 (a distance from the penetration hole 47 at a degree from 0.01 mm to 0.04 mm, for example) along the concave groove portion 51 so as to overflow a little from a forming region of the penetration hole 47. That is, the synthetic resin becomes easier to be cooled by flowing into the concave groove portion 51 from the penetration hole 47 of the cylindrical body 42, thereby it is solidified when it enters at a predetermined distance in the concave groove portion 51 from the penetration hole 47 to form the protruded portion 73. The protruded portion 73 molded in the primary molding step is a part serving as the pawl portion 23 of the molded surface fastener 1 by pressing the provisional element 70 from above in the secondary molding step.

The primary molded body 11 molded in the primary molding step is produced such that molten synthetic resin is extruded from the extrusion nozzle 45, fills the penetration hole 47 of the cylindrical body 42 and flows in the concave groove portion 51, and further the synthetic resin is cooled and solidified while being supported on the outer peripheral surface of the die wheel 41 and half-turning.

Thereafter, the primary molded body 11 is continuously peeled off from the outer peripheral surface of the die wheel 41 by the pickup rollers 46. At this time, the protruded portion 73 of the primary molded body 11 is formed by being pulled out from the concave groove portion 51 of the cylindrical body 42 through the penetration hole 47 smoothly while being deformed.

For example, when the protruded portion 73 of the primary molded body 11 is pulled out of the concave groove portion 51 of the cylindrical body 42, it deforms to a shape curved or inclined upward so as to incline upward to a protruded tip end from the outer peripheral side surface of the primary stem portion 71 by exiting while sliding contacting with the inner peripheral surface of the penetration hole 47 of the cylindrical body 42, in some cases. However, just after being peeled off from the die wheel 41, the primary molded body 11 is held by the upper side holding roller 46a and the lower side holding roller 46b of the pickup rollers 46 disposed apart at a predetermined interval each other. At this time, the protruded portion 73 of the provisional element 70 which is curved or sloped upward is bent and deformed partially (plastically deformed) by being pressed from above by the upper side holding roller 46a. As a result, the protruded portion 73 of the provisional element 70 can be protruded parallel to the upper surface of the base portion 10 or to be sloped or curved downward to the base portion 10.

Therefore, in the primary molded body 11 obtained by passing the pickup rollers 46, the protruded portion 73 of each provisional element 70 is formed, in a front view viewing the provisional element 70 from M direction and with respect to the upper and lower direction, to be protruded from the outer peripheral side surface of the primary stem portion 71 in a horizontal direction substantially parallel to the upper surface of the base portion 10, or to be protruded downward rather than the horizontal direction.

The primary molded body 11 peeled off from the die wheel 41 is thereafter conveyed to the heat press apparatus 60 conducting the secondary molding step, and introduced between the upper side press roller 61 and the lower side press roller 62 of the heat press apparatus 60.

In the secondary molding step, when the primary molded body 11 passes between the upper side press roller 61 and the lower side press roller 62, at least an upper end part of each provisional element 70 of the primary molded body 11 is heated and softened by the upper side press roller 61. At this time, a temperature of the roller circumferential surface in the upper side press roller 61 is, as mentioned above, set at the predetermined temperature of the melting point of the synthetic resin of the primary molded body 11 minus 40° C. or higher and the melting point minus 10° C. or lower. At the same time, the base portion 10 of the primary molded body 11 is supported from the lower side by the lower side press roller 62, and each provisional element 70 of the primary molded body 11 is pressed from above by the upper side press roller 61, thereby the upper end part of the provisional element 70 is compressed.

Thereby, the upper end part of the primary stem portion 71 and the right and left protruded portions 73 in the provisional element 70 are thermally deformed, and the engaging head portion 22 having a head portion top end surface 22a flattened by the outer peripheral surface of the upper side press roller 61 and the stem portion 21 are molded. At the same time, two pawl portions 23 protruded on the outer peripheral side surface 22c of the engaging head portion 22 is formed from the protruded portion 73 of the provisional element 70.

At this time, the protruded portion 73 formed on the provisional element 70 of the primary molded body 11 is, regarding the upper and lower direction, protruded in the horizontal direction or the lower direction rather than the horizontal direction from the outer peripheral side surface of the primary stem portion 71, as mentioned above. The provisional element 70 is pressed from above by the upper side press roller 61 in the secondary molding step, thereby the pawl portion 23 which is provided by deforming the protruded portion 73 is formed to protrude from the outer peripheral side surface 22c of the engaging head portion 22 to curve (or slope) downward to the base portion 10. Thus, the molded surface fastener 1 of Embodiment 1 shown in FIG. 1 is stably, smoothly and efficiently manufactured.

Thereafter, the manufactured molded surface fastener 1 which is long in the machine direction is conveyed to a cutting part which is not shown in the drawings, and cut at predetermined length at the cutting part and collected, or the long molded surface fastener 1 is wound around a collecting roller and the like in a roll shape and collected in the long length state.

In the molded surface fastener 1 of Embodiment 1 manufactured as above, two micro pawl portions 23 protruded along C direction are provided on the engaging head portion 22 of each engaging element 20. Particularly, the pawl portion 23 of Embodiment 1 has a concave-shaped pawl back surface curving downward to be lower than the back surface of the head portion 22b of the engaging head portion 22. In other words, the most tip end part of the pawl portion 23 of Embodiment 1 exists at a position lower than the head portion top end surface 22a of the engaging head portion 22. Thereby, when a loop which is to be the engaging element 20 of a female surface fastener is engaged with the molded surface fastener 1 of Embodiment 1, the loop of the female surface fastener is easy to be hooked by the pawl portion 23 of each engaging element 20, and the loop is less likely to be drop off from each engaging element.

Accordingly, the molded surface fastener 1 of Embodiment 1 has a higher engaging strength (peeling strength) than conventional general molded surface fasteners without the pawl portions 23, and the engaging state with respect to the female surface fastener can be stably maintained.

In addition, in the molded surface fastener 1 of Embodiment 1, the head portion top end surface 22a and the outer peripheral side surface 22c of the engaging head portion 22 in each engaging element 20 are formed to be a smooth continuous surface. The pawl portion 23 provided to enhance the engaging strength is formed in a smaller size with respect to the engaging head portion 22, and the upper surface of the pawl portion 23 is formed in a curved surface sloping downward to the pawl tip end.

Thereby, a touch feeling of the molded surface fastener 1 can be less affected by the pawl portions 23. As a result, the molded surface fastener 1 of Embodiment 1 can have an excellent texture from which smooth touch feeling and a soft and supple touch feeling can be obtained when the molded surface fastener 1 is touched on the upper surface side on which the engaging elements 20 stand.

The molded surface fastener 1 of Embodiment 1 having high engaging strength and excellent texture as mentioned above is suitably used for goods to be put on a body such as disposable diapers, diaper covers for babies, supporters to protect limb joints, corsets for backache and gloves.

In the above Embodiment 1, the concave groove portions 51 concaved on the inner peripheral surface of the cylindrical body 42 of the molding apparatus 40 are disposed at a position relation as shown in FIG. 9 with respect to the penetration holes 47 drilled on the cylindrical body 42. That is, each concave groove portion 51 is formed continuously along C direction on an entire length between the penetration holes 47 adjacent in C direction so as to connect diameters along C direction of the penetration holes 47 which are lined in C direction. However, in manufacturing the molded surface fastener 1 of Embodiment 1, it is also possible to use a molding apparatus having a cylindrical body 42a on which the penetration holes 47 and the concave groove portions 51a to be concave portions are formed at a position relation as shown in FIG. 15, instead of the cylindrical body 42 as shown in FIG. 9.

Figure 15:
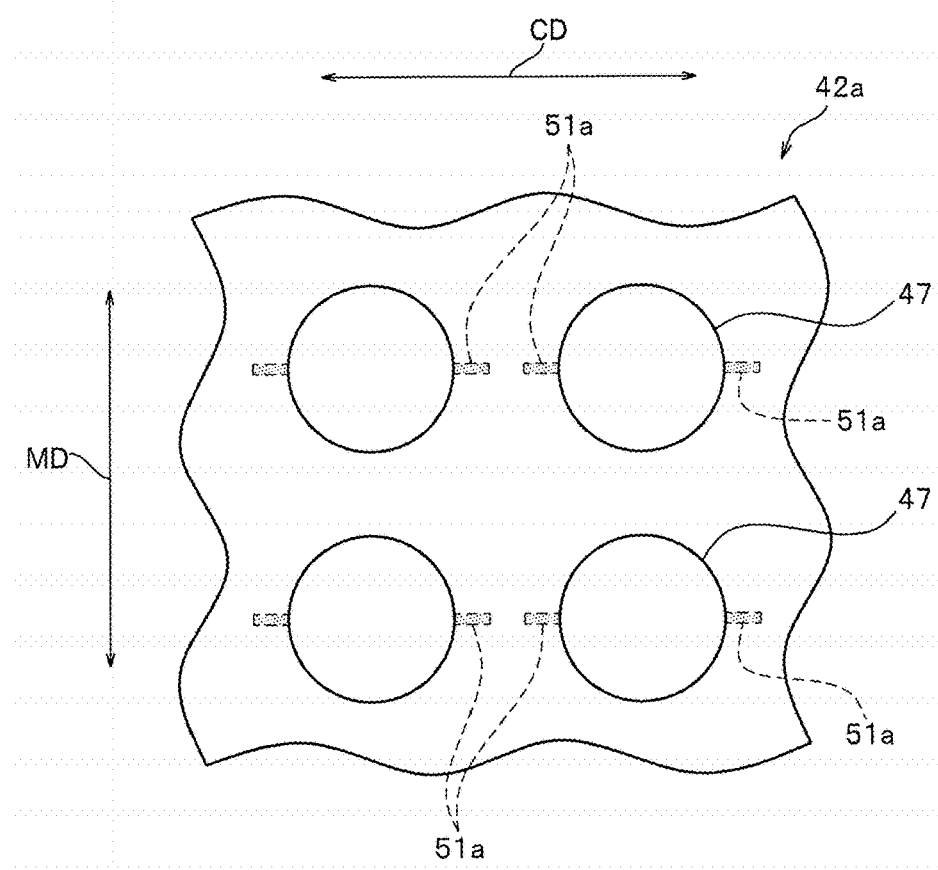
FIG. 15 is a main part schematic view illustrating a position relation between the penetration hole and the concave groove portion of the cylindrical body according to a modification example.

The penetration holes 47 of the cylindrical body 42a shown in FIG. 15 are drilled similarly to the penetration holes 47 provided on the cylindrical body 42 shown in FIG. 9. A plurality of concave groove portions (concave portions) 51a shown in FIG. 15 are concaved on the inner peripheral surface of the cylindrical body 42 along C direction. The concave groove portions 51 have a size capable of allowing synthetic resin in a molten state forming the molded surface fastener 1 to flow in. In this case, a shape and dimension of a cross section of the concave groove portion 51a in FIG. 15 is the same as those of the concave groove portion 51 concaved on the cylindrical body 42 shown in FIG. 9.

The concave groove portions 51a of FIG. 15 are formed along C direction so as to cross circular-shaped outer peripheral edges of the penetration holes 47 and continue to the diameters of the penetration holes 47, and at predetermined pitches in a circumferential direction which is M direction. Further, the concave groove portions 51a of FIG. 15 are formed from the circular-shaped outer peripheral edge of each penetration hole 47 along C direction at a predetermined length to right and left, and between the concave groove portions 51a adjacent in C direction, a flat surface (flat curved surface) on which the concave groove portion 51a is not formed is provided as a no-concave-groove-formed portion.

In this case, a length of the concave groove portion 51a from the circular-shaped outer peripheral edge of the penetration hole 47 is preferably corresponded to the protruded length of the protruded portion 73 provided on the provisional element 70 of the primary molded body 11. It should be noted that the cylindrical body 42a having the penetration holes 47 and the concave groove portions 51a as shown in FIG. 15 can be produced using the same method and means as those of the cylindrical body 42 of Embodiment 1 as shown in FIG. 9.

Molding of the primary molded body 11 is conducted in the primary molded process using the cylindrical body 42a on which the penetration holes 47 and the concave groove portions 51a are formed at a position relation as shown in FIG. 15, thereby a size (particularly, protruded length) of the protruded portion 73 formed on the provisional element 70 of the primary molded body 11 can be stabilized, compared with a case of using the cylindrical body 42 as shown in FIG. 9.

Therefore, the primary molded body 11 having a plurality of provisional elements 70 on which the protruded portions 73 having a uniform protruded length from the primary stem portions 71 are formed can be stably produced. Further, the secondary molding step as above is conducted to the obtained primary molded body 11, thereby the molded surface fastener 1 having the engaging elements 20 on which the pawl portions 23 having the relatively uniform protruded amount from the engaging head portion 22 are provided can be stably manufactured.

In the above Embodiment 1, the primary molded body 11 on which a plurality of provisional elements 70 stand on the base portion 10 as shown in FIGS. 11 to 14 is molded, and thereafter, the secondary molding step is conducted to the primary molded body 11, thereby the molded surface fastener 1 as shown in FIG. 1 is manufactured. However, in the present invention, it is also possible to manufacture a molded surface fastener having the plurality of provisional elements 70 as the engaging elements as they are such that the primary molded body 11 on which the plurality of provisional elements 70 stand on the base portion 10 as shown in FIGS. 11 to 14 are directly cooled, for example. That is, the primary molded body 11 molded by the molding apparatus 40 in the primary molding step as above can be provided as the molded surface fastener without change.

In this case, each engaging element of the manufactured molded surface fastener has a different shape from the engaging element 20 shown in FIG. 2, and has the primary stem portion 71 of the provisional element 70 having a frustum shape as a stem portion as shown in FIGS. 11 to 14, and two protruded portions 73 of the provisional element 70 are provided as micro pawl portions (i.e. the engaging element 70 in this case has the stem portion 71 and two pawl portions 73). In each engaging element, the engaging head portion 22 as in the engaging element 20 as shown in FIG. 2 is not provided.

Therefore, the pawl portion (i.e. the protruded portion 73 of Embodiment 1) of the engaging element is, in a plan view of the engaging element, protruded from the upper end outer peripheral edge of the stem portion (i.e. primary stem portion 71 of Embodiment 1) in a frustum shape to an outside in a horizontal direction parallel to the upper surface of the base portion 10 or downward on the lower side rather than the horizontal direction.

In this case, when the molded surface fastener (i.e. the primary molded body 11 of Embodiment 1) is peeled off from the outer peripheral surface of the die wheel 41 by the pickup rollers 46 continuously, the right and left pawl portions (i.e. protruded portions 73 of Embodiment 1) of the engaging element can be pressed from above to be partially plastically deformed by the upper side holding roller 46a of the pickup rollers 46. As a result, the protruded direction of the right and left pawl portions can be stably directed to the horizontal direction or on the lower side rather than the horizontal direction.

Further, it is also possible that after the molded surface fastener (i.e. the primary molded body 11 of Embodiment 1) is peeled off by the pickup rollers 46, the molded surface fastener is cooled while being conveyed horizontally with a conveying apparatus which is not shown in the drawings, for example. Thereby, the right and left pawl portions (i.e. the protruded portions 73 of Embodiment 1) are partially further bent and deformed so as to hang downward by its own weight, and the protruded direction of the pawl portions can be directed on the lower side rather than the horizontal direction parallel to the upper surface of the base portion 10.

Further, the pawl portions of the engaging element can be curved and deformed downward further intentionally by providing a heating part on an upper part of the conveying apparatus or blowing hot air from above of the molded surface fastener conveyed by the conveying apparatus. Thereby, the molded surface fastener in which the pawl portions are protruded to be bent or curved downward rather than the horizontal direction toward the base portion 10 can be more stably manufactured.

In the case of the molded surface fastener manufactured as above, the upper end surface of the stem portion (i.e. the primary stem portion 71 of Embodiment 1) is formed to be a circular shape. The pawl width dimension of the micro pawl portion (i.e. the protruded portion 73 of Embodiment 1) is set at half or smaller of the diameter of the circular-shaped upper end surface of the stem portion, preferably one third or smaller, and more preferably one fourth or smaller.

The specific size of the engaging element in this case is set as below. A height dimension A of the engaging element is set at 0.05 mm or more and 1.5 mm or less, and preferably 0.2 mm or more and 1.0 mm or less. The diameter of the circular-shaped upper end surface of the stem portion is set at 0.1 mm or more and 0.5 mm or less. The pawl width dimension F of the pawl portion is set at 0.01 mm or more and 0.10 mm or less, and preferably 0.03 mm or more and 0.08 mm or less. The pawl length dimension of the pawl portion is set at 0.01 mm or more and 0.04 mm or less.

The molded surface fastener having the provisional elements 70 of Embodiment 1 as above as the engaging elements can have a high peeling strength due to the micro pawl portions with respect to a female surface fastener. Further, excellent texture and touch feeling as same as those of Embodiment 1 can be stably obtained. In the present invention, each primary molded body molded in the primary molding step can be used as it is as the molded surface fastener in not only Embodiment 1 but also Embodiments 2 to 4, as described later.

Embodiment 2

Figure 16:
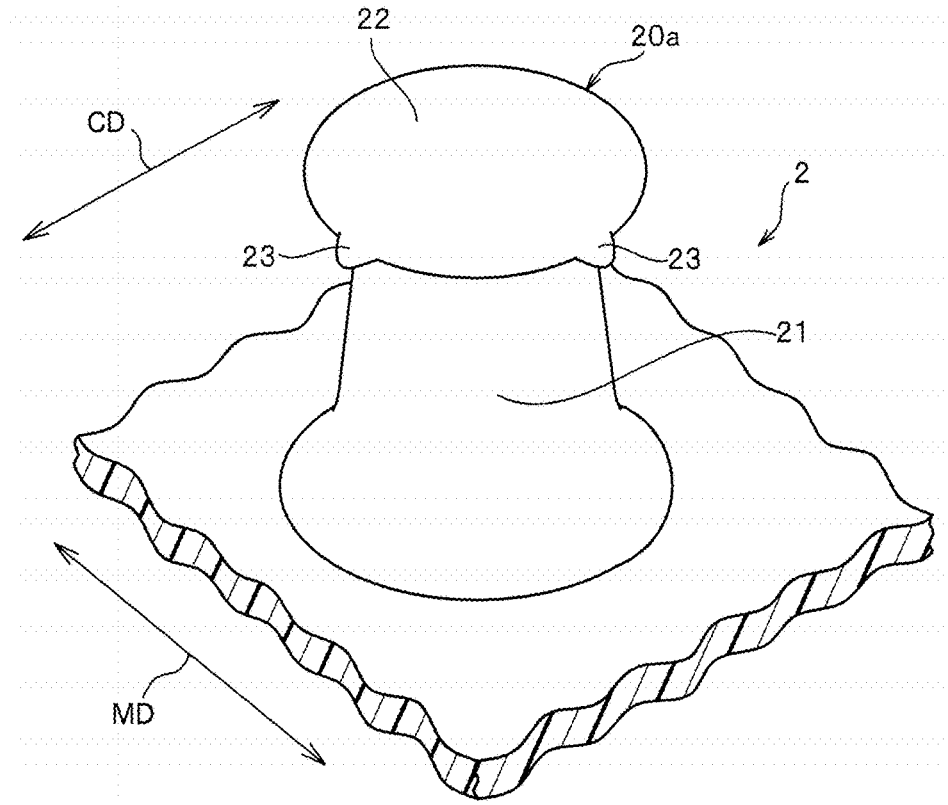
FIG. 16 is a perspective view illustrating an engaging element of a molded surface fastener manufactured in Embodiment 2 of the present invention.
Figure 17:
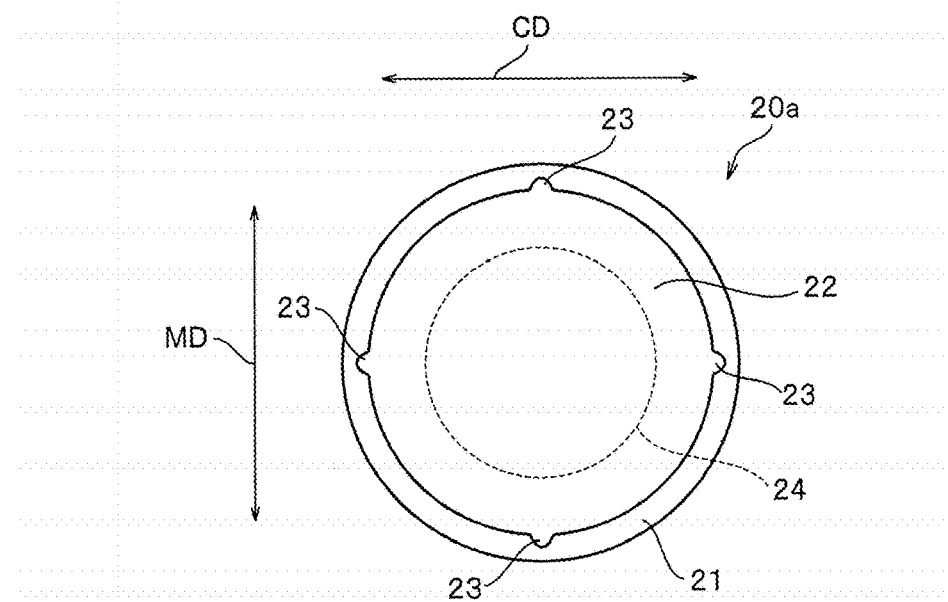
FIG. 17 is a plan view illustrating the engaging element only.

FIG. 16 is a perspective view illustrating an engaging element of a molded surface fastener manufactured in Embodiment 2. FIG. 17 is a plan view illustrating the engaging element only.

In the molded surface fastener 2 of Embodiment 2, the number of the pawl portions 23 provided on the engaging head portion 22 of each engaging element 20a is four which is different from the case of Embodiment 1 as above. However, except changing the forming number of the pawl portions 23, the molded surface fastener 2 of Embodiment 2 is formed substantially same as the molded surface fastener 1 explained in the above-mentioned Embodiment 1.

Therefore, in Embodiment 2, Embodiments 3 and 4 as well as each modification example which are described later, structures which are different from the molded surface fastener 1 of the above-mentioned Embodiment 1 are mainly explained, and parts and members having substantially same structures as the above-mentioned molded surface fastener 1 of Embodiment 1 are not explained but represented with the same reference signs.

The molded surface fastener 2 of Embodiment 2 has a plurality of engaging elements 20a standing vertically on an upper surface of a thin plate-shaped base portion 10. The plurality of engaging elements 20a are disposed to align along M direction (MD) and C direction (CD). Each engaging element 20a has a stem portion 21 standing on the base portion 10, an engaging head portion 22 integrally formed on the stem portion 21 and having a disc shape and four pawl portions 23 protruded on an outer peripheral edge part of the engaging element 22. In this case, the stem portion 21 and the engaging head portion 22 of Embodiment 2 are formed substantially same as the stem portion 21 and the engaging head portion 22 of the engaging element 20 of Embodiment 1 as above.

In the engaging element 20a of Embodiment 2, the four pawl portions 23 are protruded along the diameter direction of the engaging element 22 from the outer peripheral side surface 22c of the engaging head portion 22 in M direction and C direction. These four pawl portions 23 are disposed regularly at positions of 0°, 90°, 180° and 270° based on a center of the engaging head portion 22 showing a circular shape in a plan view of the engaging element 20a as shown in FIG. 17. It should be noted that a shape and a size of each pawl portion 23 formed in Embodiment 2 are the same as those of the pawl portion 23 provided on the molded surface fastener 1 of Embodiment 1 as mentioned above.

In Embodiment 2, the molded surface fastener 2 having the engaging element 20a on which the four pawl portions 23 are disposed as above is manufactured using the manufacturing apparatus 30 having the molding apparatus 40 and the heat press apparatus 60 as shown in FIG. 7, as in the case of Embodiment 1 as above. In the case of Embodiment 2, a cylindrical body 42a disposed on the die wheel 41 of the molding apparatus 40 has a different structure from the cylindrical body 42 used in the above-mentioned Embodiment 1 in order to provide four pawl portions 23 on each engaging element 20a.

Figure 18:
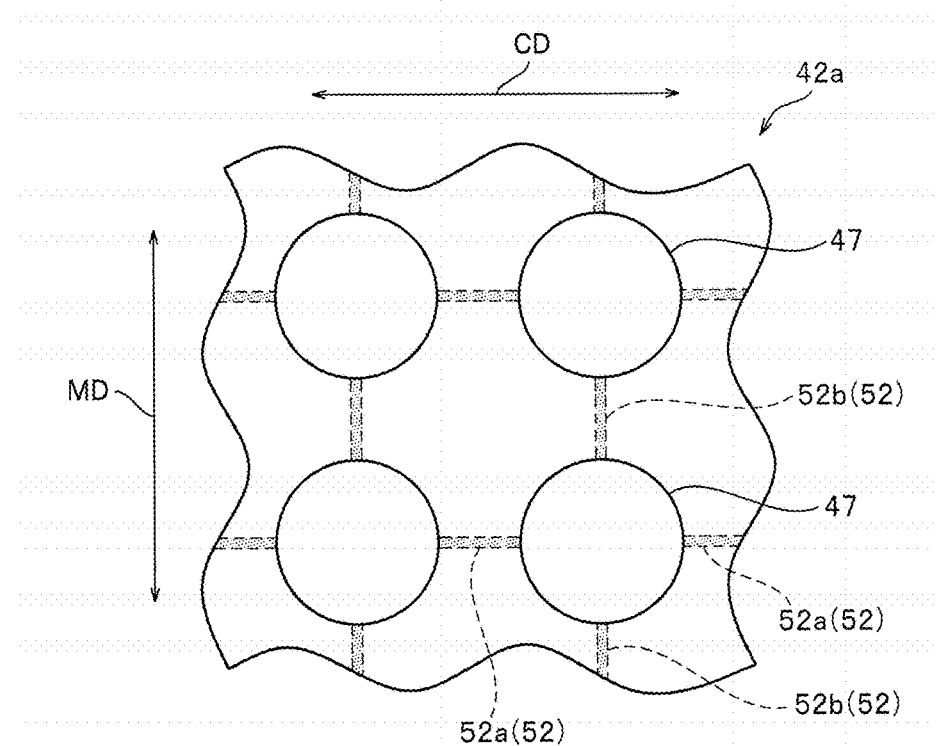
FIG. 18 is a main part schematic view illustrating a position relation between a penetration hole and a concave groove portion of a cylindrical body according to Embodiment 2.

The cylindrical body (sleeve) 42a used in Embodiment 2 has, as shown in FIG. 18, a plurality of penetration holes 47 penetrating along the diameter direction of the cylindrical body 42a from the outer peripheral surface to the inner peripheral surface, and a plurality of concave groove portions 52 concaved on the inner peripheral surface of the cylindrical body 42a to be a concave portion. The penetration holes 47 formed on the cylindrical body 42a of Embodiment 2 are formed as same as the penetration holes 47 formed on the cylindrical body 42 of Embodiment 1 as above. That is, the penetration holes 47 of Embodiment 2 are formed to penetrate from the outer peripheral surface to the inner peripheral surface of the cylindrical body 42a, and are formed at predetermined pitches in M direction (circumferential direction) and C direction of the cylindrical body 42a.

The concave groove portion (concave portion) 52 formed on the inner peripheral surface of the cylindrical body 42a of Embodiment 2 has a plurality of first concave groove portions 52a formed along C direction and a plurality of second concave groove portions 52b formed along M direction (circumferential direction) in order to provide the four pawl portions 23 on each engaging element 20a of the molded surface fastener 2.

The first concave groove portions 52a in C direction and the second concave groove portions 52b in M direction communicate to the penetration holes 47 formed on the cylindrical body 42a. The first concave groove portions 52a and the second concave groove portions 52b are formed to have predetermined pitches on a straight line along C direction and M direction, respectively so as to connect diameters of the plurality of penetration holes 47 lined in C direction and M direction. Therefore, an imaginary extension line obtained by extending the first concave groove portions 52a into the penetration holes 47 and an imaginary extension line obtained by extending the second concave groove portions 52b into the penetration holes 47 have a relation to be perpendicular to each other at a central position of each penetration hole 47.

It should be noted that in Embodiment 2, forming pitches of the penetration holes 47 provided on the cylindrical body 42a and forming pitches of the concave groove portions 52 in a circumferential direction correspond to each other, but the cylindrical body can be formed such that forming pitches of the penetration holes 47 and the forming pitches of the first concave groove portions 52a and the second concave groove portions 52b do not correspond to each other.

The first concave groove portions 52a and the second concave groove portions 52b of Embodiment 2 are continuously formed on an entirely length between the adjacent penetration holes 47 along C direction and M direction. It should be noted that the first concave groove portions 52a and the second concave groove portions 52b of Embodiment 2 may be formed to extend from the circular-shaped outer peripheral edge of each penetration hole 47 at a predetermined length only along C direction and M direction, as explained in Embodiment 1 as above referring to FIG. 15. In this case, between the adjacent first concave groove portions 52a in C direction and the adjacent second concave groove portions 52b in M direction, a flat surface on which the first concave groove portions 52a and the second concave groove portions 52b are not formed as a no-concave-groove-formed portion.

Figure 19:
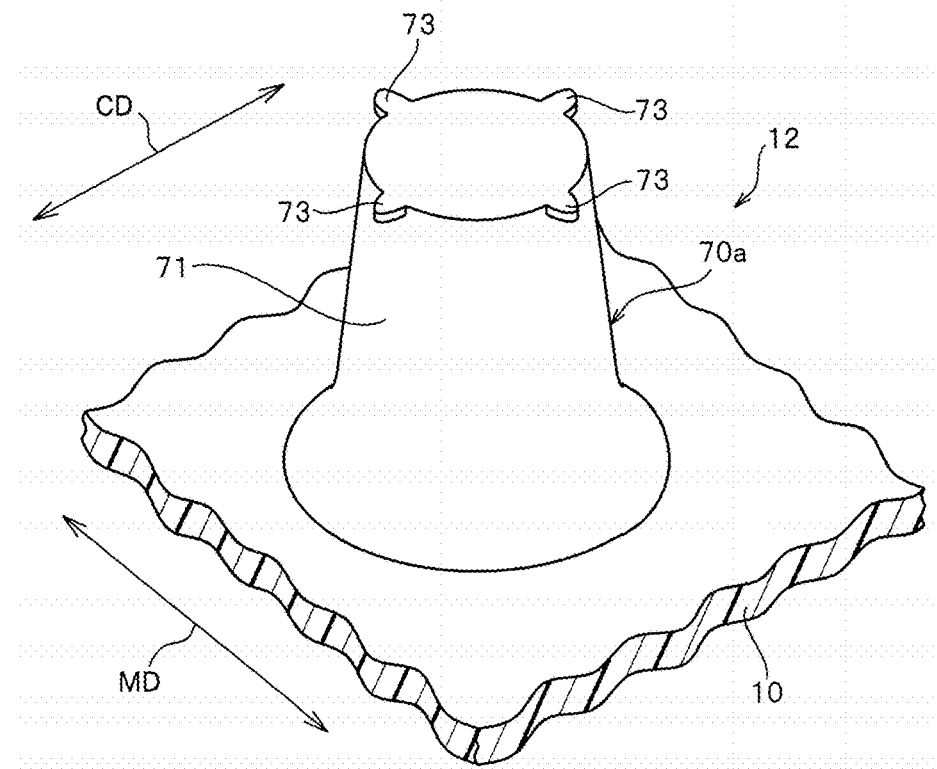
FIG. 19 is a perspective view illustrating a provisional element of the primary molded body molded in Embodiment 2.
Figure 20:
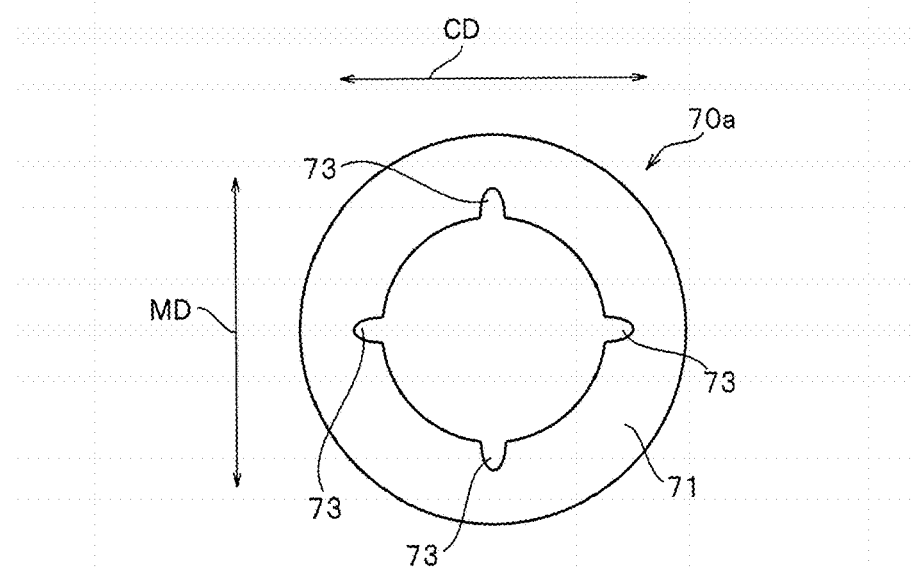
FIG. 20 is a plan view illustrating the provisional element only.

In Embodiment 2, a primary molded body 12 on which a plurality of provisional elements 70a stand on the base portion 10 as shown in FIGS. 19 and 20 is molded by conducting the primary molding step using the molding apparatus 40 having the cylindrical body 42a on which the penetration holes 47, the first concave groove portions 52a and the second concave groove portions 52b are formed as shown in FIG. 18. In this case, each provisional element 70a has a primary stem portion 71 standing on the base portion 10 and having a frustum shape and four protruded portions 73 extending to bulge to an outside from the outer peripheral side surface of the upper end part of the primary stem portion 71.

The four protruded portions 73 disposed on one provisional element 70a are molded such that synthetic resin flows in the first concave groove portions 52a and the second concave groove portions 52b concaved on the inner peripheral surface of the cylindrical body 42a from the penetration holes 47 of the cylindrical body 42a in the primary molding step. Therefore, the four protruded portions 73 are formed to protrude from the outer peripheral side surface of the primary stem portion 71 along the diameter direction of the circular-shaped upper surface of the primary stem portion 71 in C direction and M direction.

And, the primary molded body 12 in Embodiment 2 having the provisional elements 70a as shown in FIGS. 19 and 20 is then conveyed to the heat press apparatus 60 in which the secondary molding step is conducted, and each provisional element 70a is heated and pressed from above by the upper side press roller 61 as in the case of Embodiment 1 as above.

Thereby, the molded surface fastener 2 having the plurality of engaging elements 20a shown in FIGS. 16 and 17 is stably, smoothly and efficiently manufactured. In this case, the four micro pawl portions 23 disposed on each engaging element 20a are formed from the four protruded portions 73 provided on each provisional element 70a of the primary molded body 12.

As mentioned above, in the molded surface fastener 2 manufactured in Embodiment 2, the number of the pawl portions 23 provided on each engaging element 20a is four, more than the case of Embodiment 1 as above. Therefore, in the molded surface fastener 2 of Embodiment 2, higher engaging force than that of the molded surface fastener 1 manufactured in the above Embodiment 1 can be easily obtained. A shape and a size of each pawl portion 23 itself is the same as those of Embodiment 1. Therefore, texture on the top surface (upper surface) of the molded surface fastener 2 can be improved.

It should be noted that as mentioned above, also in Embodiment 2, it is also possible that the primary molded body 12 molded in the primary molding step is provided as it is as the molded surface fastener. That is, the molded surface fastener provided in this case is formed such that the plurality of provisional elements 70a as shown in FIGS. 19 and 20 stand on the base portion 10 as an engaging element (i.e. the engaging element 70a in this case has a stem portion 71 and four pawl portions 73). Therefore, the molded surface fastener is provided with high peeling strength with respect to a female surface fastener by the micro pawl portions, and excellent texture and a touch feeling can be stably obtained.

Embodiment 3

Figure 21:
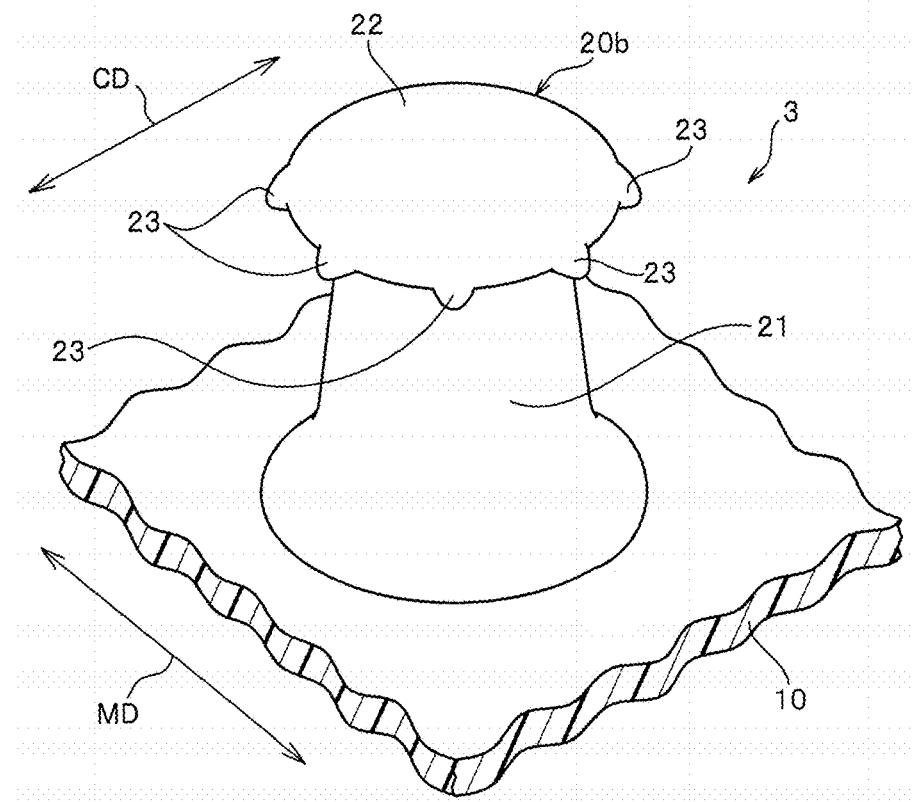
FIG. 21 is a perspective view illustrating an engaging element of a molded surface fastener manufactured in Embodiment 3 of the present invention.
Figure 22:
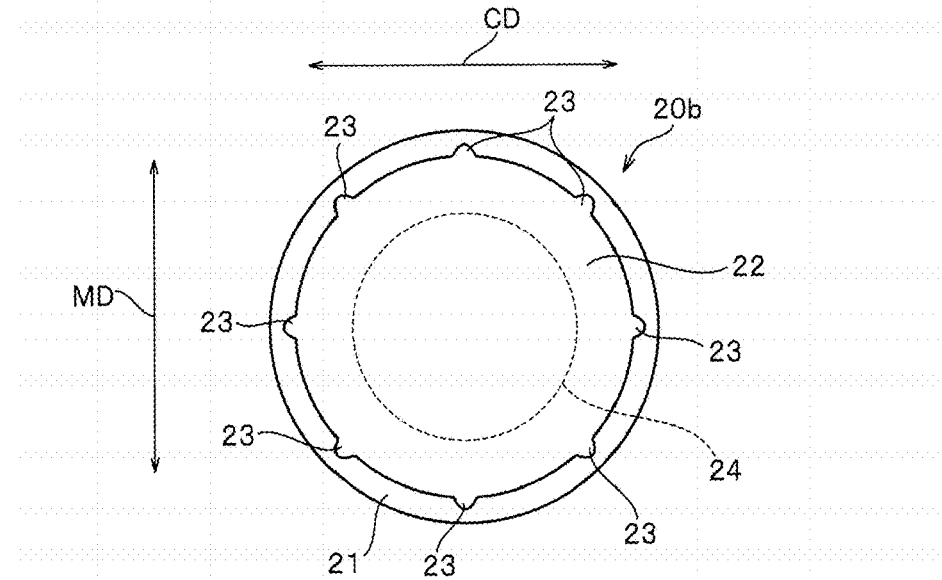
FIG. 22 is a plan view illustrating an engaging element only.

FIG. 21 is a perspective view illustrating an engaging element of the molded surface fastener manufactured in Embodiment 3. FIG. 22 is a plan view illustrating the engaging element only.

The molded surface fastener 3 of Embodiment 3 has a thin plate-shaped base portion 10 and a plurality of engaging elements 20b standing vertically on the upper surface of the base portion 10. The each engaging element 20b has a stem portion 21 standing on the base portion 10, an engaging head portion 22 integrally formed on the stem portion 21 and having a disc shape and eight pawl portions 23 protruded on the outer peripheral edge part of the engaging head portion 22. A shape and a size of each pawl portion 23 in Embodiment 3 are substantially the same as those of each pawl portion 23 formed on the molded surface fastener 1 of Embodiment 1 as above.

In the engaging element 20b of Embodiment 3, the eight pawl portions 23 are protruded along the diameter direction of the engaging head portion 22 from the outer peripheral side surface 22c of the engaging head portion 22 to an outside. The eight pawl portions 23 are, in a plan view of the engaging element 20b shown in FIG. 22, disposed with predetermined intervals to have an angle of 45° with respect to the adjacent pawl portion 23 based on the center of the engaging head portion 22 showing a circular shape.

In Embodiment 3, the molded surface fastener 3 having the engaging elements 20b on which eight pawl portions 23 are disposed as above is manufactured using the manufacturing apparatus 30 having the molding apparatus 40 and the heat press apparatus 60 as shown in FIG. 7, similar to the case of Embodiment 1 as above.

Figure 23:
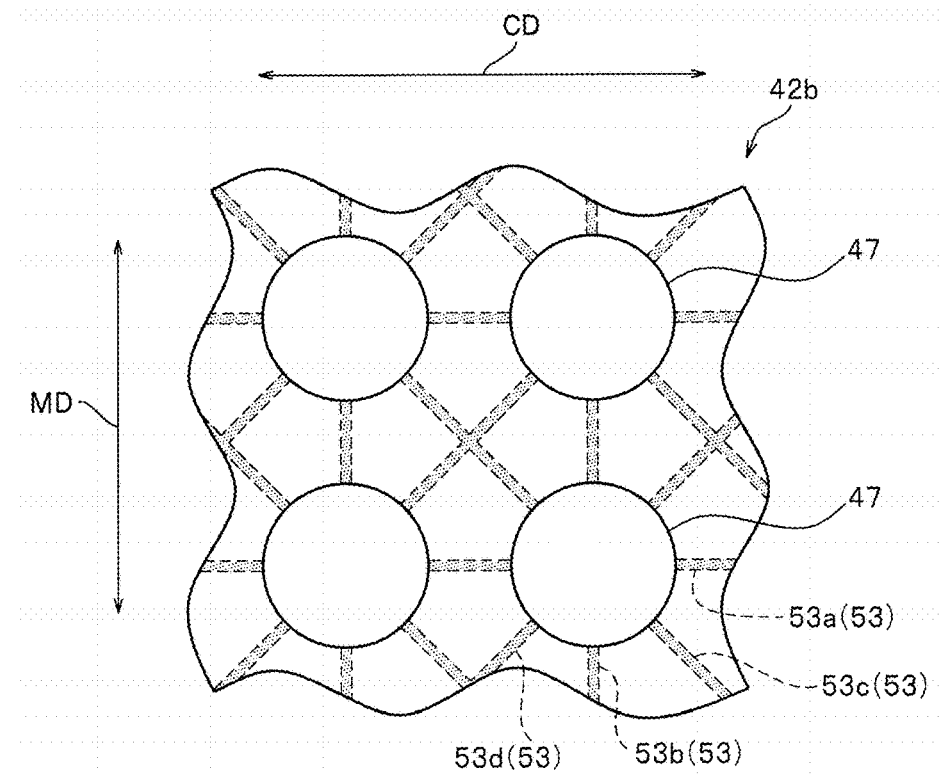
FIG. 23 is a main part schematic view illustrating a position relation between a penetration hole and a concave groove portion of the cylindrical body according to Embodiment 3.

In the case of Embodiment 3, a cylindrical body 42b disposed on the die wheel 41 of the molding apparatus 40 has a plurality of penetration holes 47 penetrating from the outer peripheral surface to the inner peripheral surface along the diameter direction of the cylindrical body 42b and a plurality of concave groove portions (concave portions) 53 concaved on the inner peripheral surface of the cylindrical body 42b as shown in FIG. 23. The penetration holes 47 formed on the cylindrical body 42b of Embodiment 3 are formed as same as the penetration holes 47 formed on the cylindrical bodies 42 and 42a of Embodiments 1 and 2, as above.

A concave groove portion 53 formed on the inner peripheral surface of the cylindrical body 42b of Embodiment 3 is to provide eight pawl portions 23 on each engaging element 20b of the molded surface fastener 3. The concave groove portion 53 has a plurality of first concave groove portions 53a formed along C direction, a plurality of second concave groove portions 53b formed along M direction (circumferential direction), as well as a plurality of third concave groove portions 53c and a plurality of fourth concave groove portions 53d formed to have an inclination angle of 45° with respect to the first concave groove portions 53a and the second concave groove portions 53b.

The first concave groove portions 53a in C direction, the second concave groove portions 53b in M direction as well as the third concave groove portions 53c and the plurality of fourth concave groove portions 53d having an inclination angle of 45° with respect to C direction and M direction are formed at predetermined pitches respectively to cross the circular-shaped outer peripheral edges of the penetration holes 47 and continue to the diameter of the penetration holes 47. Therefore, the imaginary extension lines extending the first concave groove portions 53a to the fourth concave groove portions 53d respectively into the penetration holes 47 are disposed to cross each other at the central position of each penetration hole 47. It is also possible in Embodiment 3 that the first concave groove portions 53a to the fourth concave groove portions 53d are formed to extend at a predetermined length only from the circular-shaped outer peripheral edge of each penetration hole 47, as explained referring to FIG. 15 in Embodiment 1 as above.

Figure 24:
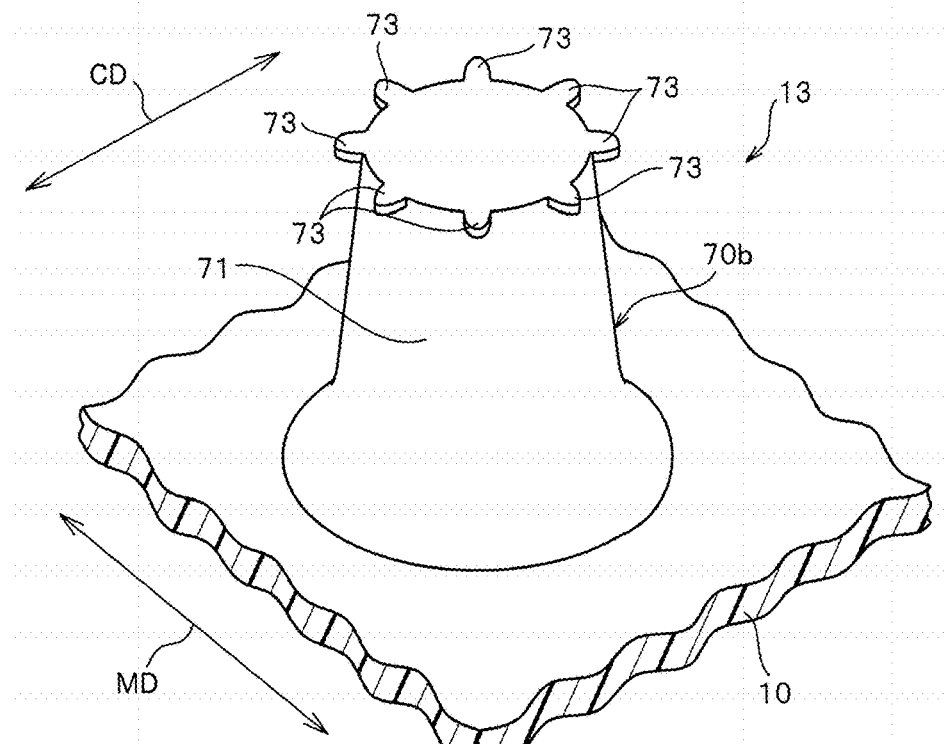
FIG. 24 is a perspective view illustrating the provisional element of the primary molded body molded in Embodiment 3.
Figure 25:
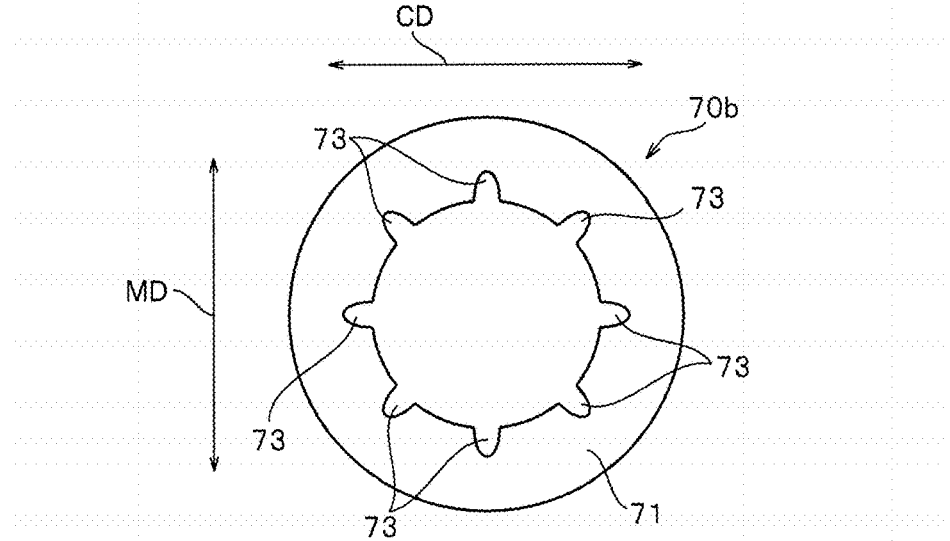
FIG. 25 is a plan view illustrating the provisional element only.

In Embodiment 3, the primary molding step is conducted using the molding apparatus 40 having the cylindrical body 42b on which the penetration holes 47 and the first concave groove portions 53a to the fourth concave groove portions 53d are provided as shown in FIG. 23, thereby the primary molded body 13 on which a plurality of provisional elements 70b stand on the base portion 10 is molded as shown in FIGS. 24 and 25. In this case, each provisional element 70b has a primary stem portion 71 in a frustum shape standing on the base portion 10 and eight protruded portions 73 extending from the outer peripheral side surface of the upper end part of the primary stem portion 71 to bulge outward.

The eight protruded portions 73 disposed on one provisional element 70b are molded such that synthetic resin flows into the first concave groove portions 53a to the fourth concave groove portions 53d concaved on the inner peripheral surface of the cylindrical body 42b from the penetration holes 47 of the cylindrical body 42b in the primary molding step. Therefore, the eight protruded portions 73 are formed to protrude from the outer peripheral side surface of the primary stem portion 71 along the diameter direction of the circular-shaped upper surface of the primary stem portion 71 in C direction, M direction and directions crossed thereto at an inclination angle at 45°.

The primary molded body 13 of Embodiment 3 having the provisional elements 70b shown in FIGS. 24 and 25 are thereafter conveyed to the heat press apparatus 60 in which the secondary molding step is conducted, and each provisional elements 70b is heated and pressed from above by the upper side press roller 61, as same as in the case of the above-mentioned Embodiment 1.

Thereby, the molded surface fastener 3 having the plurality of engaging elements 20b shown in FIGS. 21 and 22 are stably, smoothly and efficiently manufactured. In this case, eight micro pawl portions 23 disposed on each engaging element 20b are formed from the eight protruded portions 73 provided on each provisional element 70b of the primary molded body 13.

Since the number of the pawl portions 23 provided on each engaging element 20b is eight in the molded surface fastener 3 manufactured in Embodiment 3 as above, higher engaging force than the cases of Embodiment 1 and Embodiment 2 as above can be easily obtained. Further, the size and the shape of each pawl portion 23 is the same as those of Embodiment 1 as above, therefore texture of the molded surface fastener 3 on the top surface (upper surface) can be improved.

It should be noted that in Embodiment 3, the primary molded body 13 molded in the primary molding step can be provided as a molded surface fastener as it is (i.e., the engaging element 70b of the molded surface fastener in this case has a stem portion 71 and eight pawl portions 73).

Further in the present invention, forms such as the number, shape, size and disposition of the pawl portion provided on each engaging element of the molded surface fastener are not limited to Embodiment 1 to Embodiment 3 as above and can be arbitrarily changed depending on the use of the molded surface fastener.

For example, in the die wheel 41 of the molding apparatus 40 conducting the primary molding step as mentioned above in the present invention, forming pitches of the concave groove portions 51, 52, 53 provided on the inner peripheral surface of the cylindrical bodies 42, 42a, 42b can be arbitrarily changed not to correspond to the forming pitches of the penetration holes 47 provided on the cylindrical bodies 42, 42a, 42b.

For example, it is possible to set the forming pitches of the concave groove portions 51, 52, 53 provided on the inner peripheral surface of the cylindrical bodies 42, 42a, 42b smaller than the forming pitches of the penetration holes 47 so that the number of the pawl portions 23 provided on the engaging head portion 22 is different between each engaging element.

On the other hand, it is also possible to set the forming pitches of the concave groove portions 51, 52, 53 larger than the forming pitches of the penetration holes 47. Thereby, it can be possible to manufacture the molded surface fastener in which not only the number of the pawl portions provided on the engaging head portion is different between each engaging element, but also an engaging element on which the pawl portion is provided on the engaging head portion and an engaging element on which the pawl portion is not formed on the engaging element stand.

In Embodiment 1 to Embodiment 3 as mentioned above, the plurality of concave groove portions 51, 52, 53 are formed to have the same groove width and groove depth each other on one cylindrical body 42, 42a, 42b. In the present invention, however, it is also possible that a plurality of concave groove portions 51, 52, 53 having different groove width from each other and different groove depth from each other are provided on one cylindrical body 42, 42a, 42b. Thereby, it is possible to make a protruded angle and a size of the pawl portion provided on the engaging head portion change between each engaging element. Further, in the case of providing a plurality of the pawl portions with respect to one engaging head portion, it is possible to provide a plurality of pawl portions having different protruded angles from each other and a plurality of pawl portions having different sizes from each other with respect to one engaging head portion.

Further, in the present invention, the form of the pawl portion can be easily changed by changing the forming pattern of the concave groove portion or the concave portion provided on the cylindrical body of the molding apparatus 40 conducting the primary molding step. Here, the forming patterns of the concave groove portion or the concave portion provided on the inner side cylindrical body will be explained illustrating several modification examples using the drawings.

FIGS. 26 to 33 are main part schematic views explaining schematically a position relation of the penetration holes 47 formed to penetrate from the outer peripheral surface to the inner peripheral surface of the cylindrical body 42b and the concave groove portions 53 or the concave portions provided on the inner peripheral surface of the cylindrical body 42b. In the drawings, two circles show the outer peripheral edges of the penetration holes 47 drilled on the cylindrical body. The concave groove portions or the concave portions formed on the inner peripheral surface of the cylindrical body are shown as a dashed line, and groove bottom surfaces of the concave groove portions or bottom surfaces of the concave portions are shown in a gray color.

Figure 26:
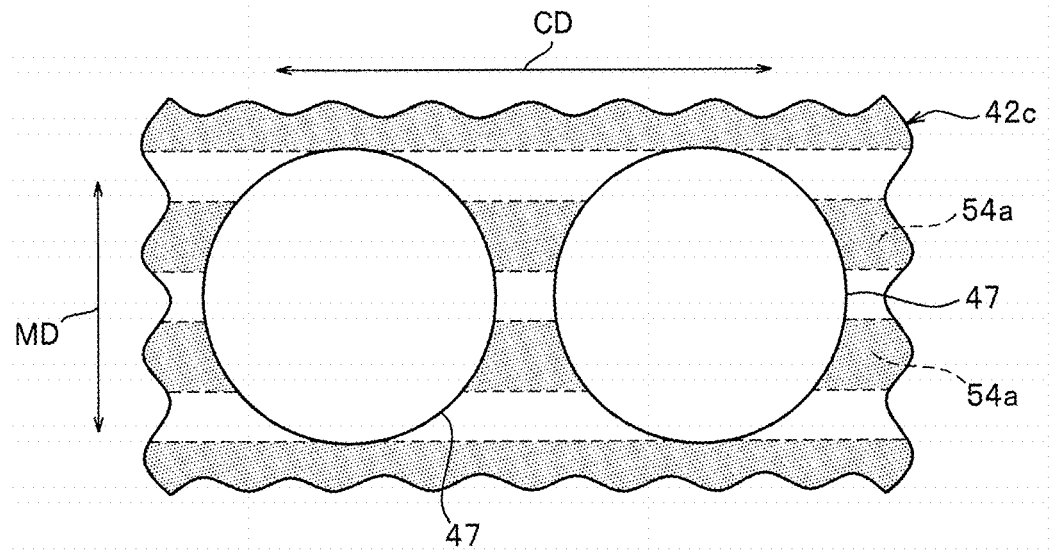
FIG. 26 is a main part schematic view illustrating a position relation between a penetration hole and a concave groove portion of the cylindrical body according to the modification example 1.
Figure 27:
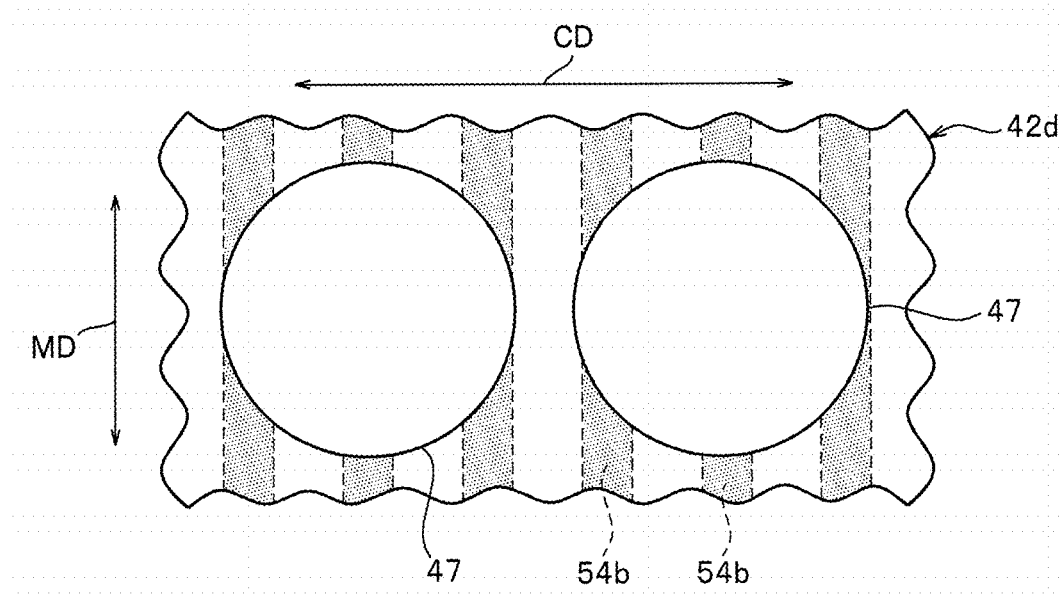
FIG. 27 is a main part schematic view illustrating a position relation between a penetration hole and a concave groove portion of the cylindrical body according to the modification example 2.
Figure 28:
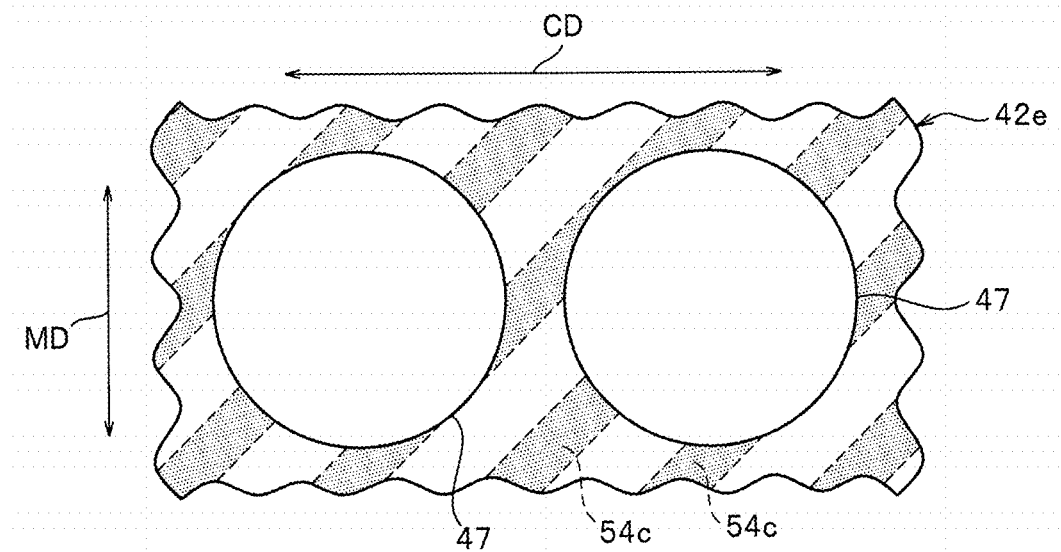
FIG. 28 is a main part schematic view illustrating a position relation between a penetration hole and a concave groove portion of the cylindrical body according to the modification example 3.

In the modification example 1 shown in FIG. 26, a plurality of concave groove portions 54a disposed linearly along C direction are concaved on the inner peripheral surface of the cylindrical body 42c as a concave portion to have a large groove width and to form a stripe pattern.

For example, in Embodiment 1 as mentioned above, only one concave groove portion 51 which is disposed on the inner peripheral surface of the cylindrical body 42 along C direction is formed with respect to one circular-shaped penetration hole 47 at a position overlapping with the diameter of the penetration hole 47 as shown in FIG. 9. On the other hand, in the modification example 1, a plurality of concave groove portions 54a are disposed to cross with respect to one circular-shaped penetration hole 47 by setting the groove width of each concave groove portion (concave portion) 54a larger and setting the intervals (forming pitches) between the adjacent concave groove portions 54a smaller than the case of Embodiment 1.

In this case, the number of concave groove portions 54a formed with respect to one circular-shaped penetration hole 47 in C direction can be easily changed by changing appropriately the size of the penetration holes 47 drilled on the cylindrical body 42c or the groove width dimension and the forming interval of the concave groove portions 54a formed on the inner peripheral surface of the cylindrical body 42c.

As in the modification example 1, the primary molded body is molded using the cylindrical body 42c on which a plurality of concave groove portions 54a in C direction are formed on one circular-shaped penetration hole 47. Further, the secondary molding step is conducted to the primary molded body. Thereby, the molded surface fastener having the engaging elements on which three or more pawl portions are regularly or irregularly protruded on the outer peripheral edge part of the engaging head portion can be stably manufactured.

In Embodiment 1 and the modification example 1, one or a plurality of concave groove portions 51, 54a having a constant groove width dimension in C direction are provided at constant forming pitches on the inner peripheral surface of the cylindrical body 42, 42c with respect to one circular-shaped penetration hole 47. In the present invention, however, it is also possible to provide a plurality of concave groove portions in C direction having different groove width dimensions from each other or a plurality of concave groove portions in C direction having different forming pitches on the inner peripheral surface of the cylindrical body 42, 42c.

In Embodiment 1 and the modification example 1, only concave groove portions in C direction are formed on the inner peripheral surface of the cylindrical body. In the present invention, however, only a plurality of concave groove portions 54b along M direction (circumferential direction) may be provided on the inner peripheral surface of the cylindrical body 42d as a concave portion, as in the modification example 2 shown in FIG. 27. It is also possible, as shown in the modification example 3 in FIG. 28, to manufacture the molded surface fastener by providing only a plurality of concave groove portions 54c inclined at a predetermined angle with respect to C direction or M direction on the inner peripheral surface of the cylindrical body 42e as a concave portion.

In the case of Embodiment 2 as above (FIG. 18) and the case of Embodiment 3 as above (FIG. 23), not only the first concave groove portions 52a, 53a along C direction, but also the second concave groove portions 52b, 53b along M direction and the third concave groove portions 53c and the fourth concave groove portions 53d having an inclination angle at 45° with respect to C direction or M direction are concaved at predetermined pitches on the inner peripheral surface of the cylindrical body 42b, 42c with respect to the penetration hole 47 having a predetermined size.

In the present invention, however, it is also possible in Embodiment 2 (FIG. 18), Embodiment 3 (FIG. 23), the modification example 2 (FIG. 27) and the modification example 3 (FIG. 28) that the size of the penetration hole 47 drilled on the cylindrical body 42a, 42b, 42d, 42e. Further, by making the forming pitches of the concave groove portions 52, 53, 54b, 54c concaved on the inner peripheral surface of the cylindrical body 42a, 42b, 42d, 42e small, the number of concave groove portions communicating to one circular-shaped penetration hole can be changed arbitrarily. In addition, a plurality of concave groove portions 52, 53, 54b, 54c having different groove width dimensions from each other can be provided, or the concave groove portions 52, 53, 54b, 54c can be provided at irregular forming pitches. Thereby, the molded surface fastener having the engaging elements on which a plurality of pawl portions are protruded regularly or irregularly on the outer peripheral edge part of the engaging head portion can be stably manufactured.

Figure 29:
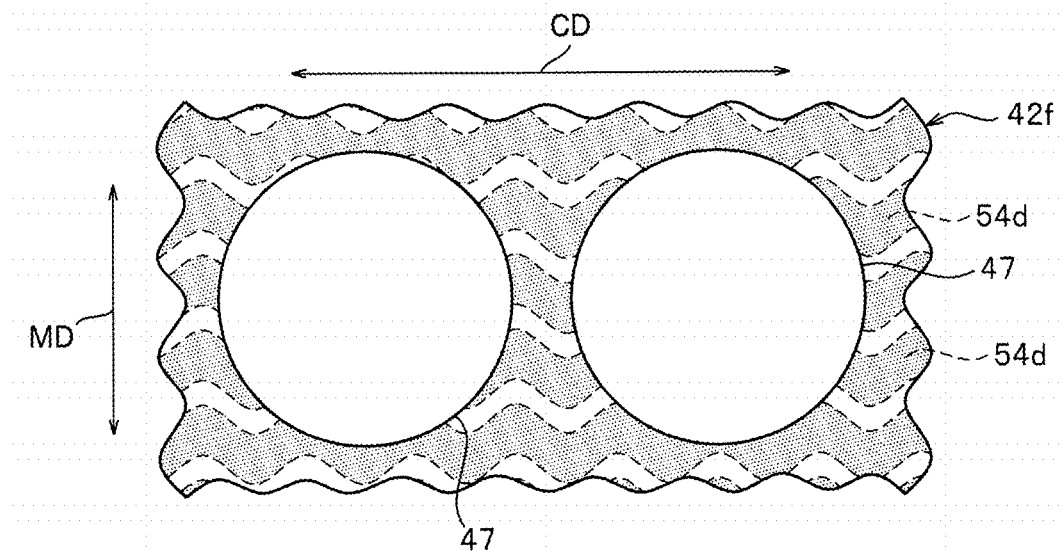
FIG. 29 is a main part schematic view illustrating a position relation between a penetration hole and a concave groove portion of the cylindrical body according to the modification example 4.

Next, in the modification example 4 as shown in FIG. 29, a plurality of concave groove portions 54*d* winding in a wavy shape along C direction are concaved at predetermined forming pitches as a concave portion on the inner peripheral surface of the cylindrical body 42*f*. In this modification example 4, one or a plurality of concave groove portions 54*d* communicating to one circular-shaped penetration hole 47 can be formed by changing the size of the penetration hole 47 drilled on the cylindrical body 42*f* or the groove width dimension and the forming pitches of the concave groove portions 54*f*.

Further, in the modification example 4, the plurality of concave groove portions 54*d* winding in a wavy shape are concaved along C direction. However, in the present invention, it is also possible to concave the plurality of concave groove portions winding in a wavy shape in the circumferential direction of the cylindrical body 42*f* which is M direction or along a direction inclined at a predetermined angle with respect to C direction or M direction.

As in the modification example 4, the molded surface fastener may be manufactured using the cylindrical body 42*f* on which the plurality of penetration holes 47 are drilled and the plurality of concave groove portions 54*d* winding in a wavy shape are concaved on the inner peripheral surface. As a result, the molded surface fastener having the engaging elements on which a plurality of pawl portions are protruded regularly or irregularly on the outer circumferential edge part of the engaging head portion can be stably obtained.

Figure 30:
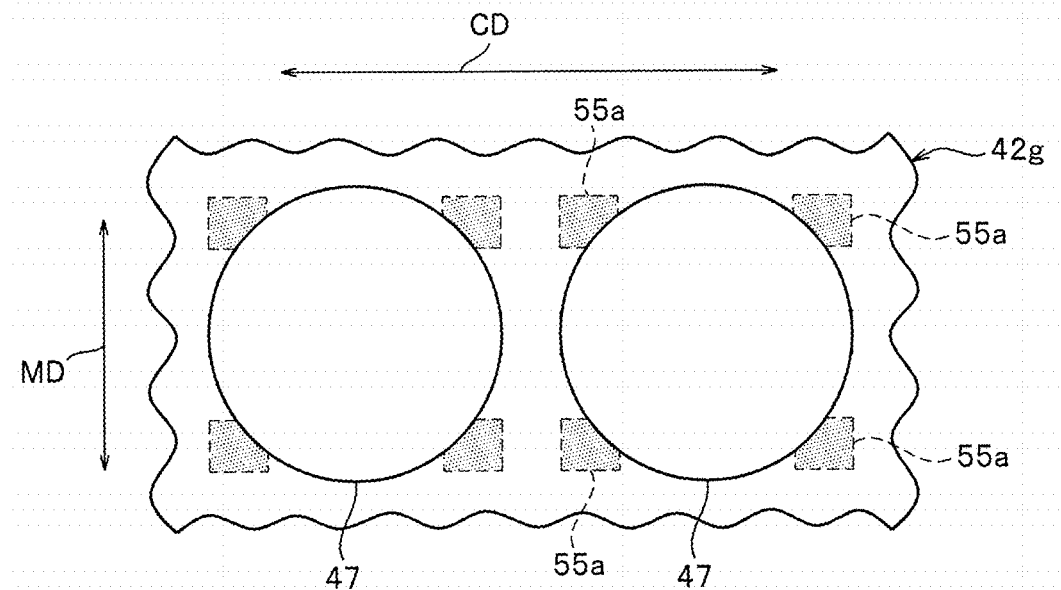
FIG. 30 is a main part schematic view illustrating a position relation between a penetration hole and a concave groove portion of the cylindrical body according to the modification example 5.

In the modification example 5 as shown in FIG. 30, contrary to the case of the cylindrical body 42*a* in Embodiment 2 as above on which the concave groove portions 52 are formed along C direction and M direction, a plurality of rectangular-shaped concave portions (recesses) 55*a* are formed at predetermined intervals in C direction and M direction so that the inner peripheral surface of the cylindrical body 42*g* are left along C direction and M direction.

In the peripheral surface of the cylindrical body 42*g* of the modification example 5, the plurality of rectangular-shaped concave portions 55*a* are concaved so that the inner peripheral surface of the cylindrical body 42*g* are left in a grid shape along C direction and M direction. In the present invention, however, it is also possible to concave the plurality of rectangular-shaped concave portions so that the grid shape on the inner peripheral surface of the cylindrical body is formed in a direction inclined at a predetermined angle with respect to C direction and M direction.

Figure 31:
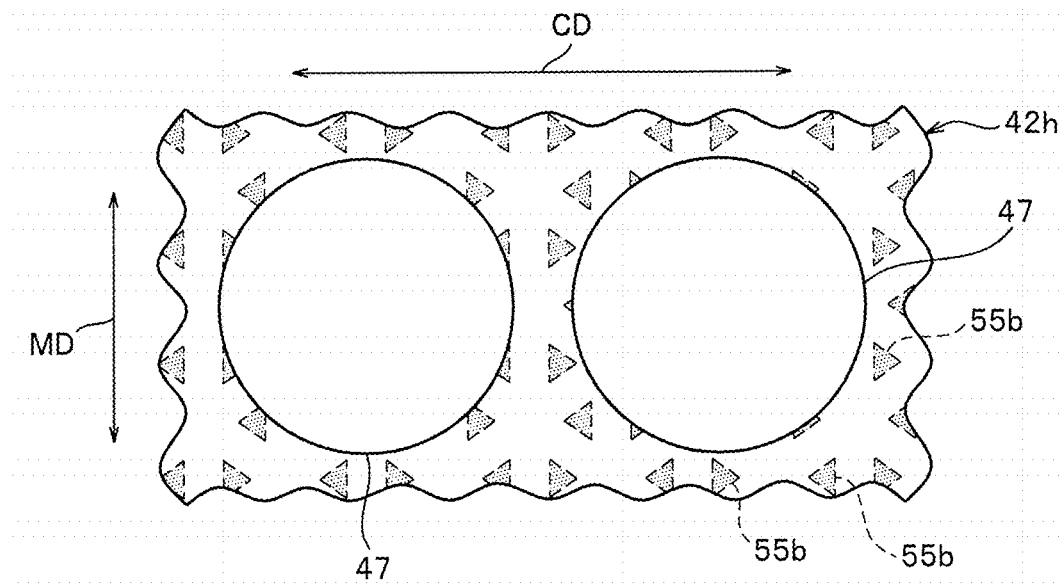
FIG. 31 is a main part schematic view illustrating a position relation between a penetration hole and a concave groove portion of the cylindrical body according to the modification example 6.

In the modification example 6 as shown in FIG. 31, a plurality of triangle-shaped concave portions (recesses) 55*b* are concaved so that the inner peripheral surface of the cylindrical body 42*h* extend linearly in various directions (to be left as a radical pattern, for example). It is also possible in the modification example 6 to change appropriately the size of the penetration holes 47 drilled on the cylindrical body 42*h* and the dimensions and the forming pitches of the concave portions 55*b*.

Figure 32:
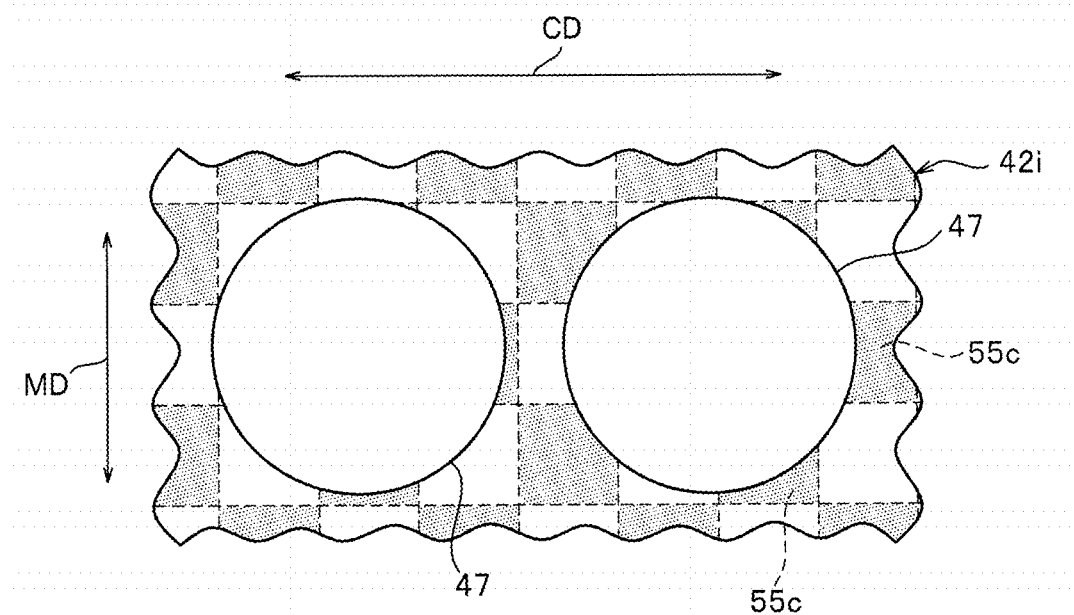
FIG. 32 a main part schematic view illustrating a position relation between a penetration hole and a concave groove portion of the cylindrical body according to the modification example 7.

In the modification example 7 as shown in FIG. 32, a plurality of square-shaped concave portions (recesses) 55*c* are concaved on the inner peripheral surface of the cylindrical body 42*i* so that the inner peripheral surface of the cylindrical body 42*c* and the square concave portions form a check pattern. It is also possible in the modification example 7 to change the size of the penetration holes 47 drilled on the cylindrical body 42*c* or the dimensions and forming pitches of the concave portions 55*c* appropriately. Further in the modification example 7, the check pattern of concave portions 55*c* are formed along C direction and M direction, but in the present invention, it is also possible to form the check pattern of the concave portions 55*c* along a direction inclined at a predetermined angle with respect to C direction or M direction.

Figure 33:
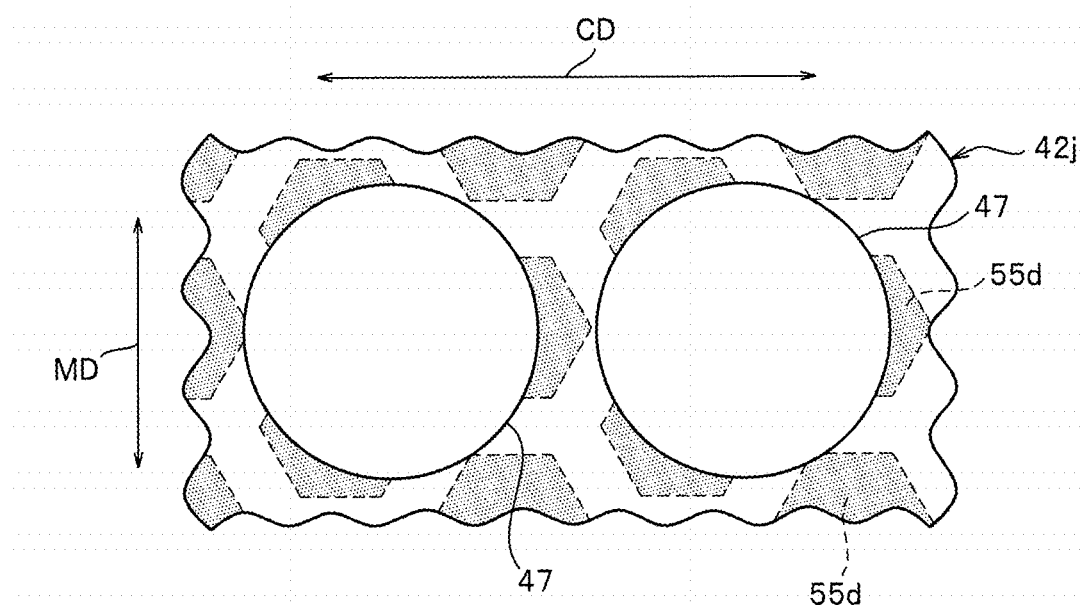
FIG. 33 a main part schematic view illustrating a position relation between a penetration hole and a concave groove portion of the cylindrical body according to the modification example 8.

In the modification example 8 as shown in FIG. 33, a plurality of concave portions (recesses) 55*d* in a regular hexagonal shape are formed at predetermined intervals on the inner peripheral surface of the cylindrical body 42*j* so that the inner peripheral surface of the cylindrical body 42*j* is left as a tortoise shell pattern. In the modification example 7, it is also possible to appropriately change the size of the penetration holes 47 drilled on the cylindrical body 42*j* or the size and forming pitches of the concave portions 55*d* in the regular hexagonal shape.

The molded surface fastener having the engaging elements on which a plurality of pawl portions are regularly or irregularly protruded on the outer peripheral edge part of the engaging head portion can be stably obtained also by manufacturing the molded surface fastener using each cylindrical body 42*f* to 42*j* as shown in the modification example 5 to the modification example 8.

For the concave groove portion or the concave portion of the present invention as above, it is sufficient to have a gap allowing molten synthetic resin to enter. Further, it is also possible in the present invention that a boundary surface between the concave groove portion or the concave portion and a non-formed portion in which the concave groove portion or the concave portion is not formed is sloped or curved, thereby formed vaguely. A shape of the concave groove portion or the concave portion having a vague boundary includes emboss processing or satin finishing conducted on the inner peripheral surface of the cylindrical body.

And each molded surface fastener using each cylindrical body 42*c* to 42*j* shown in the above-mentioned modification example 1 to modification example 8 has high engaging force stably with respect to a female surface fastener having loops because a plurality of pawl portions are regularly or irregularly protruded on the engaging head portion of each engaging element. Further, texture on the top surface (upper surface) of the molded surface fastener can be improved.

Embodiment 4

Figure 34:
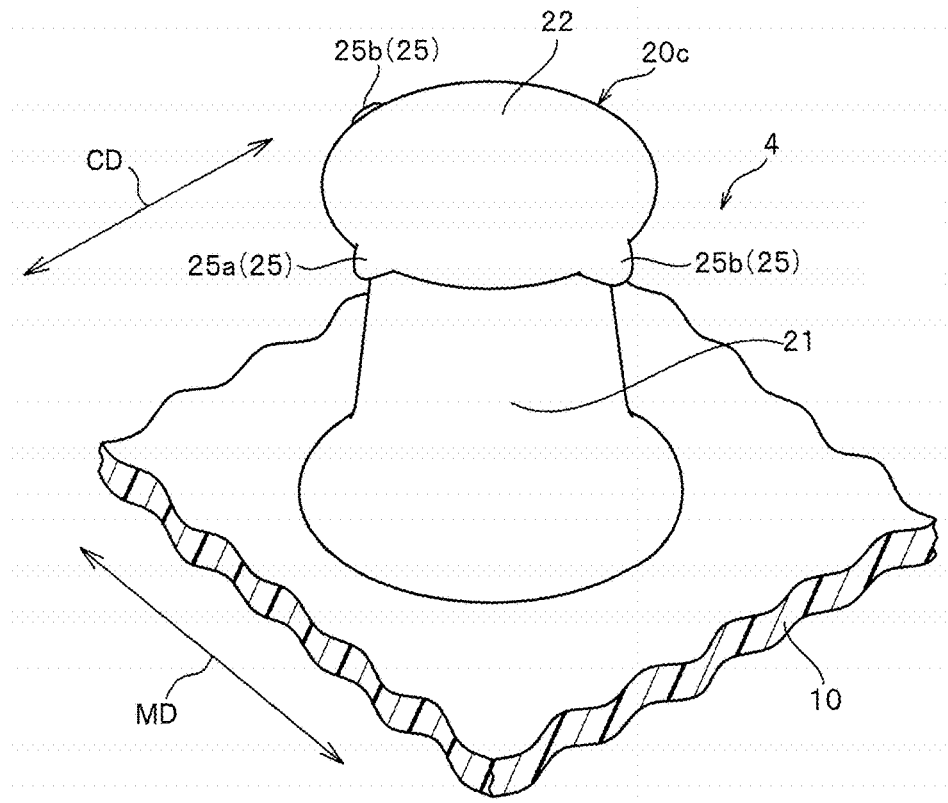
FIG. 34 is a perspective view illustrating an engaging element of a molded surface fastener manufactured in Embodiment 4 of the present invention.
Figure 35:
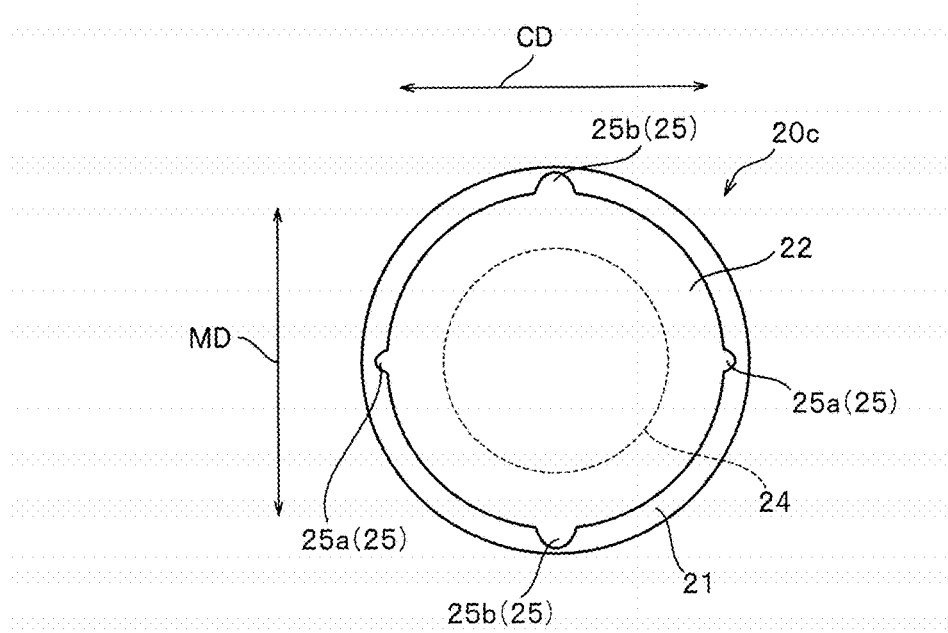
FIG. 35 is a plan view illustrating the engaging element only.

FIG. 34 is a perspective view illustrating an engaging element of a molded surface fastener manufactured in Embodiment 4 of the present invention. FIG. 35 is a plan view illustrating the engaging element only.

The molded surface fastener 4 of Embodiment 4 has a thin plate-shaped base portion 10 and a plurality of engaging elements 20*c* standing vertically on the upper surface of the base portion 10. Each engaging element 20*c* has a stem portion 21 standing on the base portion 10, a disc-shaped engaging head portion 22 integrally formed on the stem portion 21 and four pawl portions 25 protruded on the outer peripheral edge part of the engaging head portion 22. In this case, the stem portion 21 and the engaging head portion 22 of Embodiment 4 are formed substantially same as the stem portion 21 and the engaging head portion 22 in the engaging element 20 of Embodiment 1 as above.

In the engaging element 20*c* of Embodiment 4, four pawl portions 25 are protruded from the outer peripheral side surface 22*c* of the engaging head portion 22 in C direction and M direction along the diameter direction of the engaging head portion 22. These four pawl portions 25 are, in a plan view of the engaging element 20c shown in FIG. 35, regularly arranged at positions of 0°, 90°, 180° and 270° based on the center of the engaging head portion 22 showing a circular shape.

Particularly the pawl portion 25 of Embodiment 4 has right and left pair of first pawl portions 25a protruded from the engaging head portion 22 in C direction and a front and rear pair of second pawl portions 25b protruded from the engaging head portion 22 in M direction. In this case, in the plan view of the engaging element 20c, two first pawl portions 25a are protruded at a position relation to be point symmetric each other based on the center of the engaging head portion 22. Two second pawl portions 25b are protruded at a position relation to be point symmetric each other based on the center of the engaging head portion 22. Further, the first pawl portions 25a and the second pawl portions 25b of Embodiment 4 has a shape hanging down toward a tip end as a claw of a bird, as the pawl portion 23 of Embodiment 1 as above.

The first pawl portion 25a of Embodiment 4 is protruded on the outer peripheral side surface 22c of the engaging head portion 22 at a size slightly smaller than the second pawl portion 25b. Here, the meaning of that the first pawl portion 25a is smaller than the second pawl portion 25b is that at least either dimension (preferably both dimensions) of the pawl width dimension and the pawl length dimension (a dimension from the outer peripheral side surface 22c of the engaging head portion 22 to the pawl tip end position) of the first pawl portion 25a is smaller than the second pawl portion 25b.

Further, the first pawl portion 25a and the second pawl portion 25b of Embodiment 4 are formed at a micro size such that each pawl width dimension is one third or smaller of a dimension of the engaging element 20c at the boundary 24 in M direction (width dimension), preferably one fifth or smaller and more preferably one seventh or smaller. The pawl width dimension of the first pawl portion 25a and the second pawl portion 25b is specifically set at 0.01 mm or more and 0.10 mm or less, and preferably 0.03 mm or more and 0.08 mm or less. The pawl length dimension of the first pawl portion 25a and the second pawl portion 25b is set at 0.01 mm or more and 0.04 mm or less.

Figure 36:
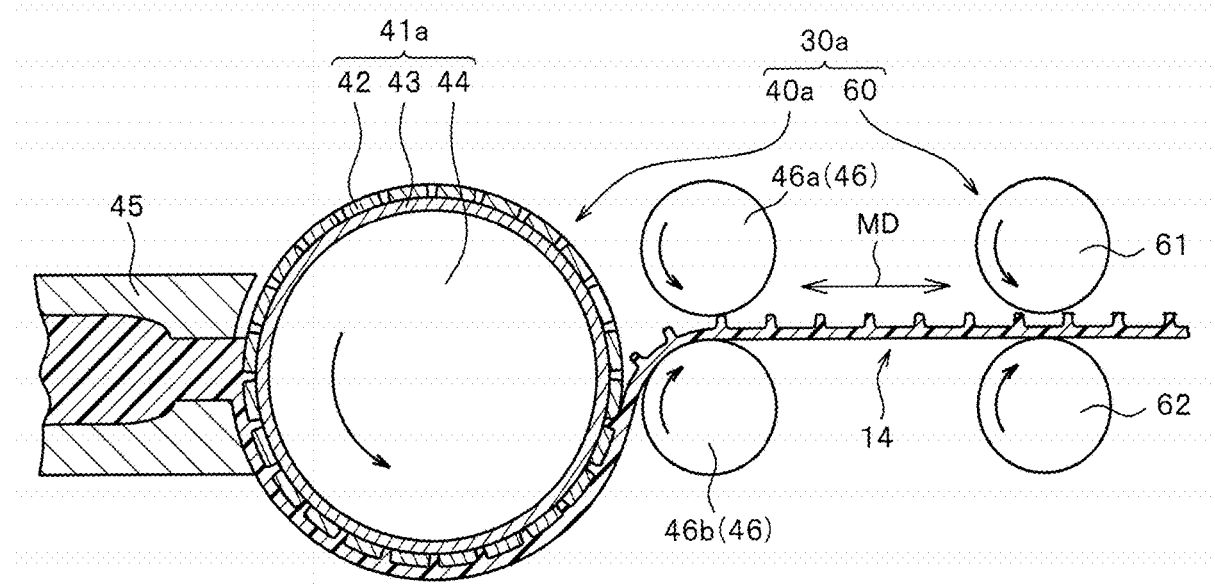
FIG. 36 is a schematic view schematically illustrating a manufacturing apparatus of the molded surface fastener according to Embodiment 4.

The molded surface fastener 4 of Embodiment 4 having the above structure is manufactured using a manufacturing apparatus 30a as shown in FIG. 36.

The manufacturing apparatus 30a has a molding apparatus 40a conducting the primary molding step and the heat press apparatus 60 heating and pressing the primary molded body 14 molded in the primary molding step. In this case, the heat press apparatus 60 of Embodiment 4 is formed as same as the heat press apparatus 60 of Embodiment 1 shown in FIG. 7 as above.

The molding apparatus 40a of Embodiment 4 has a die wheel 41a drive rotating in one direction (anticlockwise direction in the drawings), an extrusion nozzle 45 disposed facing to a circumferential surface of the die wheel 41a and extruding molten synthetic resin material continuously, and pickup rollers 46 disposed on a downstream side of the extrusion nozzle 45 in the rotation direction of the die wheel 41a.

In this case, the extrusion nozzle 45 and the pickup rollers 46 of Embodiment 4 are formed as same as the extrusion nozzle 45 and the pickup rollers 46 used for the molding apparatus 40 of the above-mentioned Embodiment 1 shown in FIG. 7. That is, the pickup rollers 46 have a pair of an upper side holding roller 46a and a lower side holding roller 46b which hold the primary molded body 14 molded at the die wheel 41a, as described later, from upper and lower sides.

The die wheel 41a has an outer side cylindrical body (main sleeve) 42 which becomes the mold member, an auxiliary cylindrical body (sub sleeve) 43 in a cylindrical shape and disposed closely contacting with an inside of the cylindrical body 42, and a rotation driving roller 44 which rotates the cylindrical body 42 and the auxiliary cylindrical body 43 in one direction simultaneously. In this case, the die wheel 41a has bicylindrical structure in which the outer side cylindrical body 42 and the inner side auxiliary cylindrical body 43 are concentrically and rotatably disposed. Hereinafter, the outer side cylindrical body 42 is referred to as a first cylindrical body 42, and the inner side auxiliary cylindrical body 43 is referred to as a second cylindrical body 43. In the rotation driving roller 44, a cooling jacket distributing a coolant which is not shown in the drawings is provided.

The first cylindrical body 42 on the outer side in Embodiment 4 is formed as same as the cylindrical body 42 used for the molding apparatus 40 of Embodiment 1 as above. That is, in the first cylindrical body 42 of Embodiment 4, a plurality of penetration holes 47 penetrating from the outer peripheral surface to the inner peripheral surface of the first cylindrical body 42, and a plurality of concave groove portions 51 concaved on the inner peripheral surface of the first cylindrical body 42 parallel to the central axis direction of the first cylindrical body 42 are provided.

Figure 37:
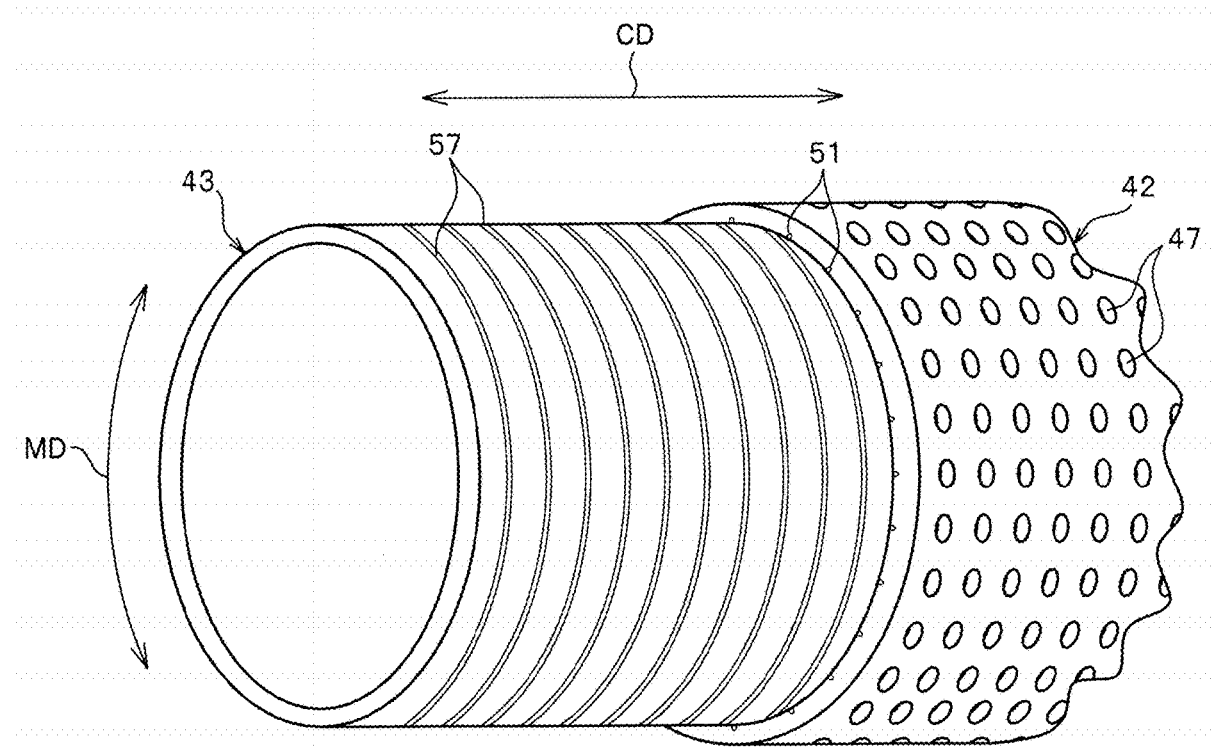
FIG. 37 is a perspective view schematically illustrating a cylindrical body and an auxiliary cylindrical body of the molding apparatus.

The inner side second cylindrical body 43 has, as shown in FIG. 37, a plurality of auxiliary concave groove portions 57 concaved on the outer peripheral surface of the second cylindrical body 43 along the circumferential direction (M direction) of the second cylindrical body 43. The second cylindrical body 43 of Embodiment 4 can be produced using the same method as the case of producing the cylindrical body 42 of Embodiment 1 as above.

In Embodiment 4, the auxiliary concave groove portions 57 of the second cylindrical body 43 are formed along the circumferential direction of the inner side cylindrical body 42 at predetermined pitches in the axis direction of the inner side cylindrical body 42 as shown in FIG. 37 so as to have a position relation overlapping with the diameter of the penetration holes 47 drilled on the first cylindrical body 42 and perpendicular to the concave groove portions 51 of the first cylindrical body 42.

In this case, the auxiliary concave groove portions 57 of the second cylindrical body 43 are concaved continuously along the circumferential direction so as to cross the penetration holes 47 of the first cylindrical body 42. The auxiliary concave groove portion 57 has a flat groove bottom surface and a pair of groove side wall surfaces facing to each other and disposed parallel to each other so as to have a square cross section. It should be noted that the auxiliary concave groove portion 57 may be formed in any shape, and may be formed to have a cross section in a polygonal shape or substantially U-shape.

The auxiliary concave groove portion 57 of Embodiment 4 has a groove width and a groove depth allowing synthetic resin in a molten state forming the molded surface fastener 4 to flow in. For example, the groove width (interval between the pair of the groove side wall surfaces) of the auxiliary concave groove portion 57 is set at from 0.01 mm to 0.10 mm and preferably from 0.03 mm to 0.08 mm. Particularly in this case, the groove width of the auxiliary concave groove portion 57 is set at one third or smaller of the dimension of the penetration hole 47 in M direction provided on the first cylindrical body 42, preferably one fifth or smaller, and more preferably one seventh or smaller. The groove depth (dimension from the outer peripheral surface of the inner side cylindrical body 42 to the groove bottom surface of the concave groove portion 51) is set at 0.005 mm or more and 0.05 mm or less, preferably 0.005 mm or more and 0.03 mm or less, and more preferably 0.01 mm or more and 0.025 mm or less.

Figure 39:
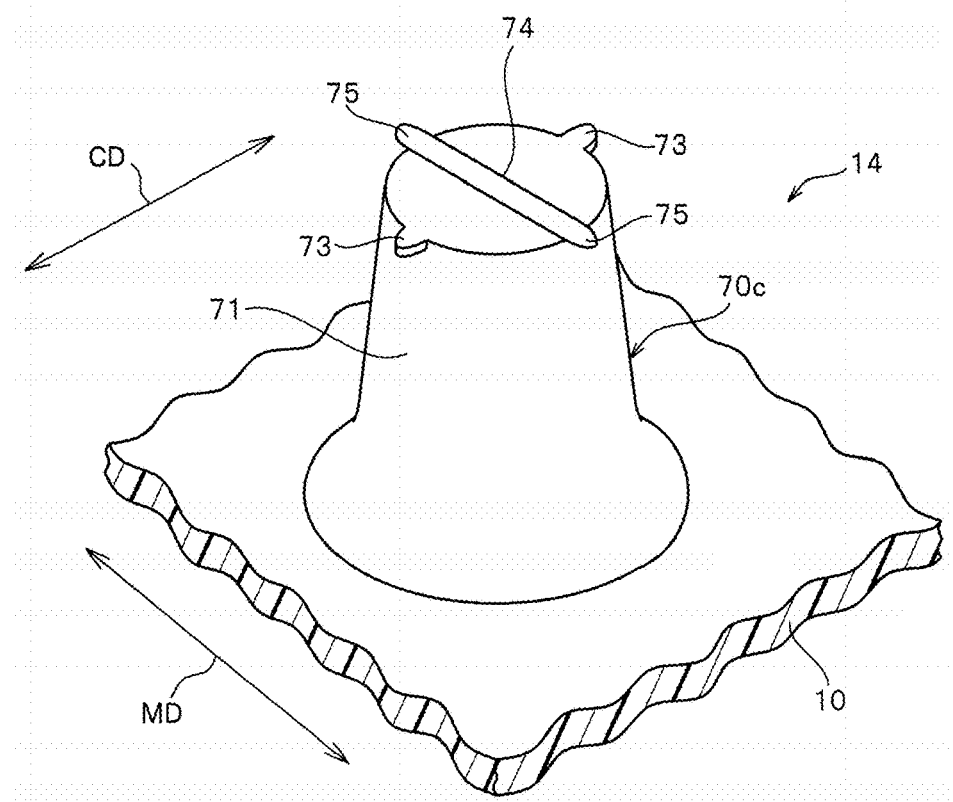
FIG. 39 is a perspective view illustrating a provisional element of the primary molded body molded with the molding apparatus.
Figure 40:
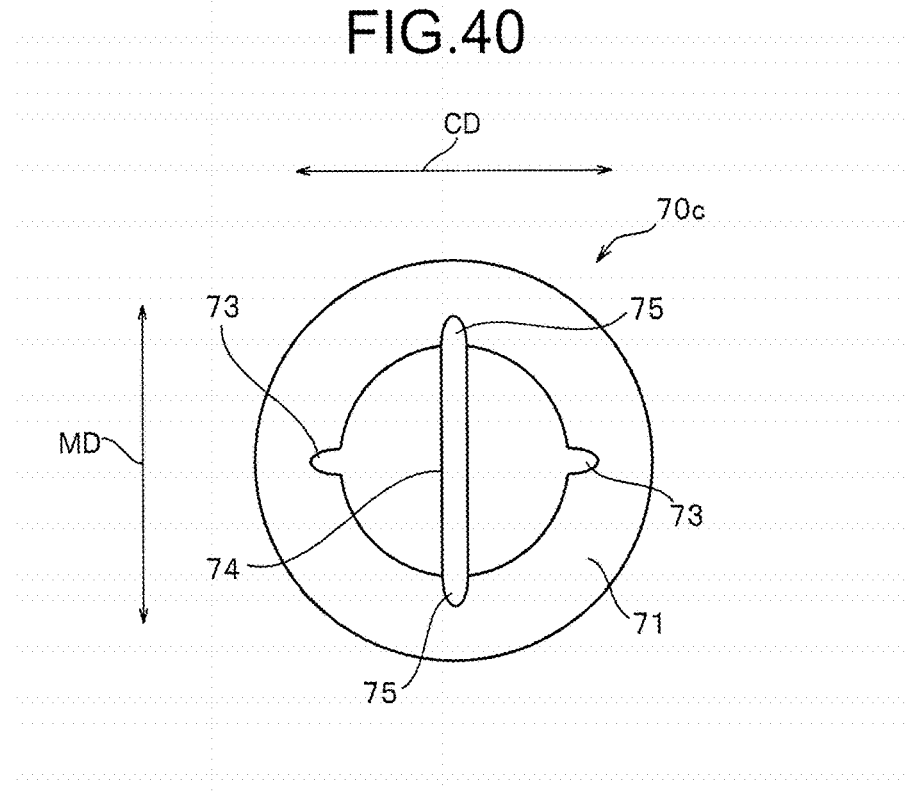
FIG. 40 is a plan view illustrating the provisional element only.

In manufacturing the molded surface fastener 4 using the molding apparatus 30*a* as above shown in FIG. 36, first the primary molding step for molding the primary molded body 14 is conducted using the molding apparatus 40*a*. Thereby, the primary molded body 14 on which a plurality of provisional elements 70*c* are integrally molded on the base portion 10 as shown in FIGS. 39 and 40 is produced.

The provisional element 70*c* of Embodiment 4 has a primary stem portion 71 in a frustum shape standing on the base portion 10, two protruded portions 73 (hereinafter, referred to as first protruded portions 73) which protrude to bulge to an outside from the outer peripheral side surface of the upper end part of the primary stem portion 71, a rib portion 74 bulging from the upper surface of the primary stem portion 71, and two additional protruded portions 75 (hereinafter, referred to as second protruded portions 75) protruded continuously from the both end edges of the rib portion 74 so as to bulge to an outside of the primary stem portion 71.

The two first protruded portions 73 disposed on the provisional element 70*c* are molded in the primary molding step by allowing synthetic resin to flow in from the penetration hole 47 of the first cylindrical body 42 to the concave groove portion 51 concaved on the inner peripheral surface of the first cylindrical body 42. Therefore, the two first protruded portions 73 are protruded to bulge to an outside from the outer peripheral side surface of the primary stem portion 71 along C direction.

The rib portion 74 and two second protruded portions 75 disposed on the provisional element 70*c* are molded by allowing synthetic resin to flow in from the penetration hole 47 of the first cylindrical body 42 to the auxiliary concave groove portion 57 concaved on the outer peripheral surface of the second cylindrical body 43. Therefore, the rib portion 74 and two protruded portions 75 are continuously formed at a height position upper than the upper surface of the primary stem portion 71 along M direction.

The primary molded body 14 molded at the die wheel 41*a* of the molding apparatus 40*a* is peeled off continuously from the outer peripheral surface of the die wheel 41*a* by the pickup rollers 46 of the molding apparatus 40*a*. At this time, the two first protruded portions 73 and the two second protruded portions 75 disposed on the provisional element 70*c* are pressed by the upper side holding roller 46*a* from above and partially bent and deformed. As a result, as in the case of Embodiment 1 as above, the first protruded portions 73 and the second protruded portions 75 can be protruded parallel or substantially parallel to the upper surface of the base portion 10, or sloped or curved downward to the base portion 10.

Thereafter, the primary molded body 14 is conveyed to the heat press apparatus 60 to conduct the secondary molding step. In the secondary molding step, as in the case of Embodiment 1 as above, the primary molded body 14 passes between the upper side press roller 61 and the lower side press roller 62, thereby an upper end part of each provisional element 70*c* of the primary molded body 14 is heated and pressed from above by the upper side press roller 61, and the upper end part of the provisional element 70*c* is compressed.

Thereby, the molded surface fastener 4 having the plurality of engaging elements 20*c* as shown in FIG. 34 and FIG. 35 is stably, smoothly and efficiently manufactured. In this case, two first pawl portions 25*a* protruded from the engaging head portion 22 of each engaging element 20*c* in C direction and two second pawl portions 25*b* protruded from the engaging head portion 22 in M direction are respectively formed from the two first protruded portions 73 and the two second protruded portions 75 (additional protruded portions 75) provided on each provisional element 70*c* of the primary molded body 14. Therefore, four pawl portions 25 in total are formed on the engaging head portion 22 of each engaging element 20*c*.

In Embodiment 4, in order to provide four pawl portions 25 with respect to the engaging head portion 22 of one engaging element 20*c* respectively, the die wheel 41*a* of the molding apparatus 40*a* has the outer side first cylindrical body 42 for molding the first protruded portions 73 and the inner side second cylindrical body 43 (auxiliary cylindrical body 43) for molding the second protruded portions 75 (additional protruded portions 75). Therefore, a forming pattern of the concave groove portions 51 concaved on the inner peripheral surface of the first cylindrical body 42 and a forming pattern of the auxiliary concave groove portions 57 concaved on the outer peripheral surface of the second cylindrical body 43 can be formed in a simple shape (pattern) respectively.

Figure 38:
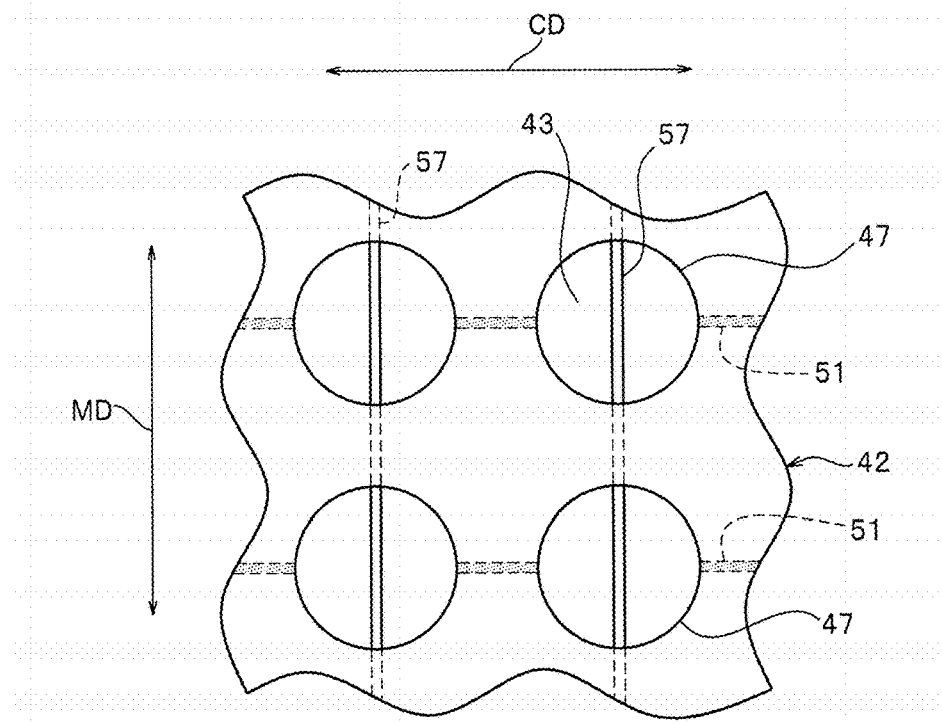
FIG. 38 is a main part schematic view illustrating a position relation between a penetration hole, a concave groove portion formed on the cylindrical body and a concave portion formed on the auxiliary cylindrical body.

In the case of Embodiment 2 as above in which four pawl portions 23 are provided on the engaging head portion 22 of one engaging element 20*a*, for example, two kinds of concave groove portions 52 which are the first concave groove portion 52*a* in C direction and the second concave groove portion 52*b* in M direction needs to be provided at predetermined patterns on the inner peripheral surface of one cylindrical body 42*a*, as shown in FIG. 18. On the other hand, in Embodiment 4, the concave groove portion 51 is concaved only in C direction on the inner peripheral surface of the first cylindrical body 42 on an outer side, and the auxiliary concave groove portion 57 is concaved only in M direction on the outer peripheral surface of the second cylindrical body 43 on an inner side, as shown in FIG. 38.

In Embodiment 4 as above, the concave groove portions required to provide the pawl portion 25 on the engaging head portion 22 can be provided separately on the outer side first cylindrical body 42 and on the inner side second cylindrical body 43. Therefore, in the case of Embodiment 4, the first cylindrical body 42 and the second cylindrical body 43 can be relatively easily produced compared with a case of forming a plurality of concave groove portions 52 in different directions with respect to one cylindrical body 42*a* as in Embodiment 2 as above.

And in the molded surface fastener 4 of Embodiment 4 thus manufactured, four pawl portions 25 are provided on each engaging element 20*c*, thereby high engaging force can be easily obtained. Further, the four pawl portions 25 provided to enhance the engaging strength are formed in a smaller size with respect to the engaging head portion 22. Thereby, the pawl portions 25 can less affect to touch feeling of the molded surface fastener 4. Therefore, texture on the top surface (upper surface) of the molded surface fastener 4 can be improved.

In Embodiment 4, as mentioned above, it is also possible that the primary molded body 14 molded in the primary molding step and having a plurality of provisional elements 70*c* as shown in FIG. 39 and FIG. 40 is provided as it is as the molded surface fastener. In this case, the provisional elements 70*c*, the primary stem portion 71, the protruded portion (first protruded portion) 73, the rib portion 74 and the additional protruded portion (second protruded portion) 75 of the primary molded body 14 as shown in FIG. 39 and FIG. 40 are used as the engaging element, the stem portion, the pawl portion, the rib portion and the additional protruded portion of the molded surface fastener (that is, the engaging element 70c of the molded surface fastener has the stem portion 71, the pawl portion 73, the rib portion 74 and the additional pawl 75). In this case, the engaging head portion is not provided on the engaging element.

Further in this case, it is preferable to horizontally convey the molded surface fastener molded with the molding apparatus 40a while being heated or blowing hot air from above to the conveyed molded surface fastener, for example. Thereby, the pawl portion and the additional pawl portion of each engaging element can be stably protruded from the outer peripheral side surface of the upper end part of the stem portion or the rib portion in a frustum shape in a horizontal direction parallel to the upper surface of the base portion 10, or to hang downward toward the base portion 10 rather than the horizontal direction.

In Embodiment 4 as above, the two first pawl portions 25a in C direction and the two second pawl portions 25b in M direction provided on the engaging element 20c have different sizes from each other as mentioned above, and the first pawl portions 25a are formed to be slightly smaller than the second pawl portions 25b. However, in Embodiment 4, the relation between the sizes of the first pawl portions 25a and the second pawl portions 25b is not limited in particular.

For example, the size of the concave groove portion 51 concaved on the inner peripheral surface of the first cylindrical body 42 and the size of the auxiliary concave groove portion 57 concaved on the outer peripheral surface of the second cylindrical body 43 may be changed. As a result, it is possible to form the first pawl portions 25a in C direction provided on the engaging element 20c larger than the second pawl portions 25b in M direction, or to form the first pawl portion 25a in C direction and the second pawl portions 25b in M direction at the same size.

In the present invention, the forming pattern of the concave groove portions or concave portions concaved on the inner peripheral surface of the outer side first cylindrical body 42 and the forming pattern of the auxiliary concave groove portions or the auxiliary concave portions concaved on the outer peripheral surface of the inner side second cylindrical body 43 in the molding apparatus 40a can be changed appropriately depending on the number, disposition and a size of the pawl portions provided on the engaging element.

In Embodiment 4 as above, for example, the concave groove portions 51 along C direction are concaved on the inner peripheral surface of the first cylindrical body 42, and the auxiliary concave groove portions 57 along M direction are concaved on the outer peripheral surface of the second cylindrical body 43. In the invention, however, it is also possible that the concave groove portions along M direction are concaved on the inner peripheral surface of the first cylindrical body 42 and the auxiliary concave groove portions along C direction are concaved on the outer peripheral surface of the second cylindrical body 43.

Figure 41:
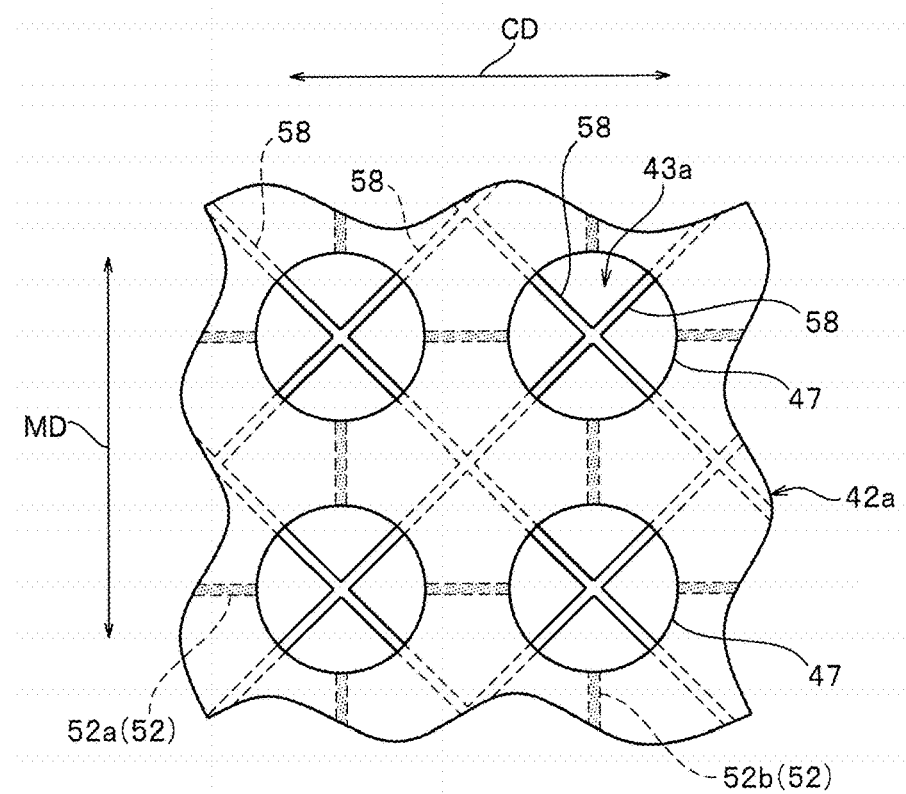
FIG. 41 is a main part schematic view illustrating a position relation between a penetration hole, a concave groove portion formed on the cylindrical body and the concave groove portion formed on the auxiliary cylindrical body according to a modification example.

Further, in a case that eight pawl portions are provided to one engaging element, for example, as an example of forming patterns of the concave groove portions 52 of the first cylindrical body 42a and the auxiliary concave groove portions 58 of the second cylindrical body 43a is shown in FIG. 41, the first concave groove portions 52a along C direction and the second concave groove portions 52b along M direction are concaved on the inner peripheral surface of the outer side first cylindrical body 42a. In the inner peripheral surface of the inner side second cylindrical body 43a, auxiliary concave groove portions 58 disposed to have an inclination angle at 45° with respect to C direction and M direction are concaved. The molding apparatus 40a having the first cylindrical body 42 and the second cylindrical body 43 as above is used, thereby the molded surface fastener having the engaging elements on which eight pawl portions are protruded on the outer peripheral edge part of the engaging head portion at regular intervals can be stably manufactured.

Further, as the forming pattern of the concave groove portions or concave portions concaved on the inner peripheral surface of the first cylindrical body and the forming pattern of the auxiliary concave groove portions or auxiliary concave portions concaved on the outer peripheral surface of the inner side second cylindrical body, it is also possible to use the patterns explained in the modification example 1 to the modification example 8 as mentioned above (see FIG. 26 to FIG. 33).

Further, in the above-mentioned Embodiment 1 to Embodiment 3 and the modification example 1 to the modification example 8, explained is a case conducting the primary molding step of the molded surface fastener using the molding apparatus 40 having the die wheel 41 shown in FIG. 7. In Embodiment 4, explained is a case conducting the primary molding step of the molded surface fastener using the molding apparatus 40a having the die wheel 41a shown in FIG. 36. However, in the present invention, a molding apparatus having the other forms can be used in the primary molding step in manufacturing the molded surface fastener.

Figure 42:
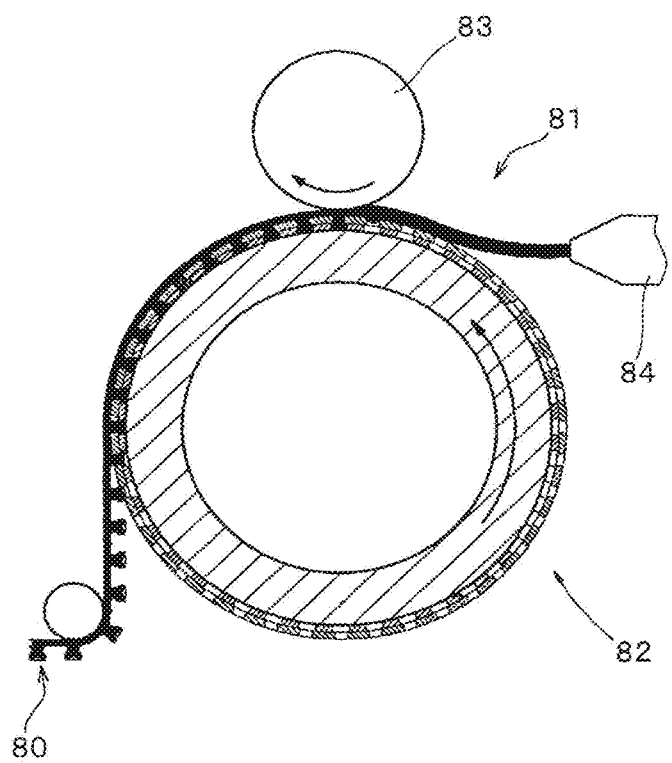
FIG. 42 is a schematic view schematically illustrating a conventional molding apparatus.
Figure 43:
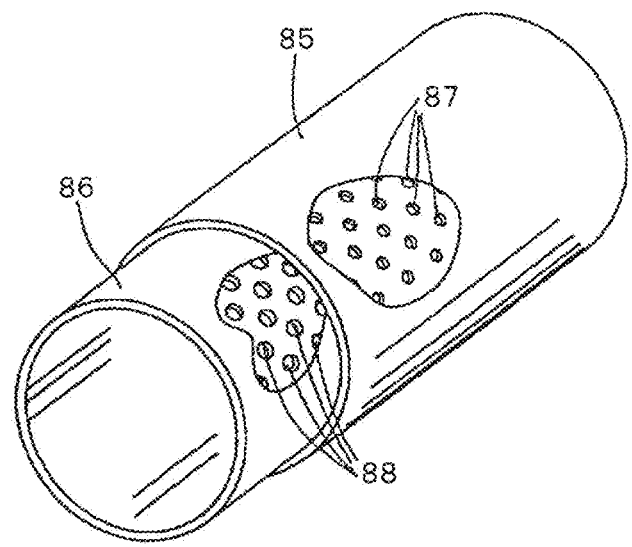
FIG. 43 is a perspective view illustrating a conventional outer side screen and an inner side screen.
Figure 44:
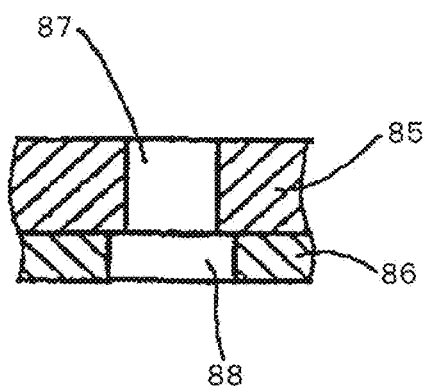
FIG. 44 is a cross-sectional view illustrating an enlarged main part of the conventional outer side screen and the inner side screen.

As an example of the molding apparatus having another form to mold the primary molded body, an apparatus having a die wheel drive rotating in one direction, a press wheel disposed apart from the die wheel at a predetermined interval and drive rotating in the opposite direction to the direction of the die wheel and an extrusion nozzle extruding molten synthetic resin material toward between the die wheel and the press wheel can be used, as same as the Patent Document 3 as above (see FIGS. 42 and 43).

In this case, the die wheel of the molding apparatus in another form has the same structure as the die wheel 41 explained in Embodiment 1 as above or the die wheel 41a explained in Embodiment 4.

That is, the die wheel in this form has a cylindrical body 42 on which a plurality of penetration holes and a plurality of concave groove portions are formed, and a rotation driving roller 44 rotating the cylindrical body 42, as explained in Embodiment 1 as above. Otherwise, it has a first cylindrical body 42 on which a plurality of penetration holes and a plurality of concave groove portions are formed, a second cylindrical body (auxiliary cylindrical body) 43 on which auxiliary concave groove portions are concaved on the outer peripheral surface and a rotation driving roller 44 rotating the first cylindrical body 42 and the second cylindrical body 43, as explained in Embodiment 4 as above.

Further in the present invention, as one more example of molding apparatus in another form, it is possible to use an apparatus having a molding side belt mechanism rotating to travel in one direction, a press side belt mechanism disposed apart from the molding side belt mechanism at a predetermined interval and rotating to travel in the opposite direction to the direction of the molding side belt mechanism and an extrusion nozzle disposed facing to the outer peripheral surface of the belt of the molding side belt mechanism and continuously extruding molten resin material.

The molding side belt mechanism has an endless belt to become a mold member and a pair of rotation roller which the endless belt is wound around and rotating to travel the endless belt in one direction. In this case, in the endless belt, a plurality of penetration holes and a plurality of concave groove portions similar to the penetration holes and the concave groove portions provided on the cylindrical body of Embodiment 1 as above are provided to mold the stem portions of the primary molded body. Further, the press side belt mechanism has an endless belt for press and a pair of rotation rollers which the endless belt for press is wound around and rotating to travel the endless belt for press.

Otherwise, as a form of the molding side belt mechanism, the one having an outer side first endless belt to become a mold member, a second endless belt (auxiliary endless belt) disposed closely contacting with the inside of the outer side first endless belt, and a pair of rotation rollers which the first endless belt and the second endless belt are wound around and rotating to travel the belts in one direction simultaneously.

In this case, in the first endless belt, a plurality of penetration holes and a plurality of concave groove portions similar to the penetration holes and the concave groove portions provided on the first cylindrical body of Embodiment 4 as mentioned above are provided. In the second endless belt, a plurality of auxiliary concave groove portions similar to the auxiliary concave groove portions provided on the outer peripheral surface of the second cylindrical body of Embodiment 4 as mentioned above are provided.

Also by conducting the primary molding step to mold the primary molded body by using molding apparatuses in yet another form having the die wheel and the press wheel as above or using molding apparatuses in yet another form having the molding side belt mechanism and the press side belt mechanism, the molded surface fastener 1 to the molded surface fastener 4 as explained in Embodiment 1 to Embodiment 4 can be stably manufactured.

REFERENCE SIGNS 1, 2, 3, 4: molded surface fastener
10: base portion
11, 12, 13: primary molded body
14: primary molded body
20: engaging element
20a, 20b: engaging element
20c: engaging element
21: stem portion
22: engaging head portion
22a: head portion top end surface
22b: head portion back surface
22c: outer peripheral side surface
23: pawl portion
24: boundary
25: pawl portion
25a: first pawl portion
25b: second pawl portion
30, 30a: manufacturing apparatus
40, 40a: molding apparatus
41, 41a: die wheel
42: cylindrical body (sleeve or first cylindrical body)
42a to 42j: cylindrical body
43, 43a: auxiliary cylindrical body (second cylindrical body)
44: rotation driving roller
45: extrusion nozzle
46: pickup roller
46a: upper side holding roller
46b: lower side holding roller
47: penetration hole
51, 51a: concave portion (concave groove portion)
52: concave portion (concave groove portion)
52a: first concave groove portion
52b: second concave groove portion
53: concave portion (concave groove portion)
53a: first concave groove portion
53b: second concave groove portion
53c: third concave groove portion
53d: fourth concave groove portion
54a, 54b: concave portion (concave groove portion)
54c, 54d: concave portion (concave groove portion)
55a, 55b: concave portion (concave groove portion)
55c, 55d: concave portion (concave groove portion)
57: auxiliary concave groove portion
58: auxiliary concave groove portion
60: heat press apparatus
61: upper side press roller (calender roller)
62: lower side press roller (calender roller)
70, 70a: provisional element
70b, 70c: provisional element
71: primary stem portion
73: protruded portion (first protruded portion)
74: rib portion
75: additional protruded portion (second protruded portion)
A: height dimension of engaging element
B: diameter of engaging head portion
C: height dimension of engaging head portion
D: diameter of engaging element at boundary
E: bulging dimension of engaging head portion
F: pawl width dimension
Θ: bulging angle of engaging head portion
MD: machine direction
CD: crossing direction

The invention claimed is:

1. A molding apparatus used for manufacturing a molded surface fastener made of synthetic resin in which a plurality of engaging elements stand on an upper surface of a base portion, the molding apparatus including a mold member, a driving part rotating the mold member at a predetermined speed, and an extrusion nozzle extruding molten synthetic resin material toward the mold member, wherein:

the mold member is provided with a plurality of penetration holes drilled to penetrate from an outer peripheral surface of the mold member to an inner peripheral surface of the mold member for forming stem portions of the engaging elements, and with a plurality of concave portions concaved on the inner peripheral surface for forming pawl portions of the engaging elements, each of the concave portions is a linear concave groove portion or a concave groove portion curved in a wavy shape, each of the concave portions has a size in which the molten synthetic resin material can flow, each of the penetration holes of the mold member communicates to at least one of the concave groove portions, and an outer peripheral edge of each of the penetration holes formed on the inner peripheral surface of the mold member includes a portion with which the at least one concave groove portion intersects and a portion with which no concave groove portion intersects.

2. The molding apparatus according to claim 1, wherein:
the mold member has a cylindrical shape, and a die wheel is formed using the mold member and the driving part.

3. The molding apparatus according to claim 1 including an auxiliary mold member disposed closely contacting with the inner peripheral surface of the mold member on an inside of the mold member and in which auxiliary concave portions communicating to the penetration holes of the mold member are concaved on an outer peripheral surface thereof, wherein
the auxiliary mold member is rotated synchronously with the mold member.

4. The molding apparatus according to claim 1, wherein:
a groove width of each of the concave groove portions is set at 0.005 mm or more and 0.1 mm or less, and
a groove depth of each of the concave groove portions is set at 0.005 mm or more and 0.05 mm or less.

\* \* \* \* \*

UNITED STATES PATENT AND TRADEMARK OFFICE
CERTIFICATE OF CORRECTION

| | | |
|---|---|---|
| PATENT NO. | : 12,023,837 B2 | Page 1 of 1 |
| APPLICATION NO. | : 17/465044 | |
| DATED | : July 2, 2024 | |
| INVENTOR(S) | : Yoshiyuki Fukuhara et al. | |

It is certified that error appears in the above-identified patent and that said Letters Patent is hereby corrected as shown below:

On the Title Page

In item (30), in Column 1, under "Foreign Application Priority Data", Line 2, delete "Apr. 15, 2016" and insert -- Apr. 18, 2016 --.

Signed and Sealed this
Twenty-seventh Day of August, 2024

Katherine Kelly Vidal
*Director of the United States Patent and Trademark Office*